United States Patent
Dutta et al.

(10) Patent No.: US 11,402,376 B2
(45) Date of Patent: **\*Aug. 2, 2022**

(54) METHODS AND DEVICES FOR DETECTION OF BIOLOGICAL MATERIALS USING ELECTRIC FIELD ASSISTED RAPID ANALYTE CAPTURE

(71) Applicant: University of Wyoming, Laramie, WY (US)

(72) Inventors: Debashis Dutta, Laramie, WY (US); Michael Taylor, Laramie, WY (US); Ravichander Rao Peesara, Laramie, WY (US)

(73) Assignee: UNIVERSITY OF WYOMING, Laramie, WY (US)

( * ) Notice: Subject to any disclaimer, the term of this patent is extended or adjusted under 35 U.S.C. 154(b) by 259 days.

This patent is subject to a terminal disclaimer.

(21) Appl. No.: 16/360,611

(22) Filed: Mar. 21, 2019

(65) Prior Publication Data

US 2019/0317088 A1 Oct. 17, 2019

Related U.S. Application Data

(60) Provisional application No. 62/647,330, filed on Mar. 23, 2018.

(51) Int. Cl.
| | | |
|---|---|---|
| G01N 33/543 | (2006.01) | |
| B01L 3/00 | (2006.01) | |
| G01N 21/76 | (2006.01) | |

(52) U.S. Cl.
CPC .. *G01N 33/54366* (2013.01); *B01L 3/502776* (2013.01); *G01N 21/76* (2013.01); *G01N 33/54306* (2013.01)

(58) Field of Classification Search
None
See application file for complete search history.

(56) References Cited

U.S. PATENT DOCUMENTS

| | | | |
|---|---|---|---|
| 5,945,344 A * | 8/1999 | Hayes | G01N 21/76 436/172 |
| 6,027,890 A | 2/2000 | Ness et al. | |
| 6,342,347 B1 | 1/2002 | Bauer | |
| 6,444,461 B1 | 9/2002 | Knapp et al. | |
| 6,815,212 B2 | 11/2004 | Ness et al. | |
| 7,312,060 B2 | 12/2007 | Rothschild et al. | |
| 7,749,445 B2 | 7/2010 | Masters | |
| 8,507,208 B2 | 8/2013 | Corcoran et al. | |
| 2003/0094369 A1 | 5/2003 | Tolley et al. | |
| 2003/0153024 A1 | 8/2003 | Sullivan et al. | |
| 2004/0115709 A1 | 6/2004 | Morozov et al. | |
| 2004/0115838 A1 | 6/2004 | Quake et al. | |
| 2004/0202994 A1 | 10/2004 | Timperman | |
| 2005/0000811 A1 | 1/2005 | Luka | |
| 2005/0221385 A1 | 10/2005 | Nikiforov et al. | |
| 2006/0105449 A1 | 5/2006 | Larmer et al. | |
| 2006/0207877 A1 | 9/2006 | Schmidt et al. | |
| 2006/0219557 A1 | 10/2006 | Nikiforov et al. | |
| 2006/0252143 A1 | 11/2006 | Lo | |
| 2007/0074972 A1 | 4/2007 | Nassef et al. | |
| 2007/0111353 A1 | 5/2007 | McCaskill et al. | |
| 2008/0012007 A1 | 1/2008 | Li et al. | |
| 2008/0108095 A1 | 5/2008 | Li | |
| 2008/0274493 A1 | 11/2008 | Quake et al. | |
| 2009/0123336 A1 | 5/2009 | Yang et al. | |
| 2009/0242429 A1 | 10/2009 | Sitdikov et al. | |
| 2010/0075340 A1 | 3/2010 | Javanmard et al. | |

(Continued)

FOREIGN PATENT DOCUMENTS

| | | |
|---|---|---|
| CN | 101201350 | 6/2008 |
| EP | 0962464 | 12/1999 |
| EP | 1199558 | 4/2002 |

(Continued)

OTHER PUBLICATIONS

Surdhar et al. (1987) "Reduction potentials and exchange reactions of thiyl radicals and disulfide anion radicals," J. Phys. Chem. 91: 6532-6537.

Taylor et al. (Oct. 2018) "A protein functionalization platform based on selective reactions at methionine residues," Nature 562, 563-568.

Zangar et al. (2005) "Studying cellular processes and detecting disease with protein microarrays," Drug Metabolism Reviews 37:3, 473-487.

Adler et al. (2009) "Novel strategies and tools for enhanced sensitivity in routine biomolecule analytics," Curr. Pharm. Anal. 5: 390-407.

(Continued)

*Primary Examiner* — Ann Montgomery
(74) *Attorney, Agent, or Firm* — Leydig, Voit & Mayer, Ltd.

(57) ABSTRACT

In one embodiment, the present invention includes a system for detecting a target analyte which includes a microfluidic device having least one microfluidic channel with a binding surface positioned in the microfluidic channel with further include a first electrode and a second electrode. The system may further include a detector and a voltage supply. Also included is a method to detect a target analyte using a described microfluidics device, introducing solution with a target analyte to a binding surface, and binding the target analyte to the binding surface by applying an electrical potential between the first and second electrodes during at least a portion of the binding step, which enhances the rate of binding of the target analyte molecules to the binding molecules. The method then includes the steps of detecting a reporter molecule which corresponds to the amount of the bound target analyte molecules, which correlates with the amount of target analyte in the original sample. The method may also include multiple applications of sample to the binding surface prior to the detection step.

18 Claims, 19 Drawing Sheets

(56) References Cited

U.S. PATENT DOCUMENTS

| | | | | |
|---|---|---|---|---|
| 2011/0177530 A1* | 7/2011 | Corcoran | ......... | G01N 33/54366 435/7.92 |
| 2019/0097257 A1 | 3/2019 | Dutta | | |

FOREIGN PATENT DOCUMENTS

| | | |
|---|---|---|
| JP | 2004219103 | 8/2004 |
| WO | WO 2008/072153 | 6/2008 |
| WO | WO 2011/011669 | 1/2011 |
| WO | WO 2017/106253 | 6/2017 |

OTHER PUBLICATIONS

Agarwal et al. (2015) "Site-specific antibody-drug conjugates: The nexus of bioorthogonal chemistry, protein engineering, and drug development," Bioconjugate. Chem. 26: 176-192.

Albers (2003) "Electrical biochip technology—a tool for microarrays and continuous monitoring" Analytical and Bioanalytical Chemistry 377(3):521-527.

Alley et al. (2008) "Contribution of Linker Stability to the Activities of Anticancer Immunoconjugates," Bioconjugate Chem. 19(3): 759-765.

Arguello et al. (2004) "Voltammetric oxidation of hantzsch 1,4-dihydropyridines in protic media: substituent effect on positions 3,4,5 of the heterocyclic ring," Electrochmica Acta. 49: 4849-4856.

Badescu et al. (2014) "Bridging disulfides for stable and defined antibody drug conjugates," Bioconjugate. Chem. 25: 1124-1136.

Ball (2013) "Designing enzyme-like catalysts: A rhodium(II) metallopeptide case study," Acc. Chem. Res. 46: 560-570.

Beier et al. (1999) "Versatile derivatisation of solid support media for covalent bonding on DNA-microchips," Nucleic Acids Res. 27(9): 1970-1977.

Bien et al. (2003) "Characterization of masking materials for deep glass micromachining," J. Micromech. Microeng. 13: S34-S40.

Bothara et al. (2008) "Nanomonitors: electrical immunoassays for protein biomarker profiling" Nanomedicine 3(4):423-436.

Chen et al. (2016) "Visible light photoredox-controlled reactions n-radicals and radical ions," Chem. Soc. Rev. 45: 2044-2056.

Cheow et al. (2010) "Increasing the Sensitivity of Enzyme-Linked Immunosorbent Assay Using Multiplexed Electrokinetic Concentrator," Anal. Chem. 82(8):3383-3388.

Chikkaveeraiah et al. (2012) "Electrochemical Immunosensors for Detection of Cancer Protein Biomarkers," ACS Nano 6: 6546-6561.

Choi et al. (2002) "An integrated microfluidic biomedical detection system for protein analysis with magnetic bead-based sampling capabilities," Lab Chip 2: 27-30.

Deangelis et al. (2009) "Unusually Reactive and Selective Carbonyl Ylides for Three Component Cycloaddition Reactions," Journal of the American Chemical Society 131: 1101-1105.

Dedeian et al. (1991) "A new synthetic route to the preparation of a series of strong photoreducing agents: fac-tris-ortho-metalated complexes of iridium(III) with substituted 2-phenylpyridines," Inorganic Chem. 30: 1687-1688.

Deiss et al. (2009) "Multiplexed sandwich immunoassays using electrochemiluminescence imaging resolved at the single bead level," J. Am. Chem. Soc. 131: 6088-6089.

Deshpande (1996) "Enzymes and Signal Amplification Systems," In; Enzyme Immunoassays: From Concept to Product Development, Chapman and Hall eds, New York, pp. 155-359.

Devaraj et al. (2008) "Tetrazine-based cycloadditions: Application to pretargeted live cell imaging," Bioconjugate Chem. 19: 2297-2299.

Doeven et al. (2013) "A potential-controlled switch on/off mechanism for selective excitation in mixed electrochemiluminescent systems," Chem. Sci. 4: 977-982.

Dujols et al. (1997) "A Long-Wavelength Fluorescent Chemodosimeter Selective for Cu(II) Ion in Water," J. Am. Chem. Soc. 119(31):7386-7387.

Dutta et al. (2011) "Microfluidic Devices for Enhancing the Sensitivity of ELISA Methods," Proceedings of the ASME 9th International Conference on Nanochannels, Microchannels, and Minichannels (ICNMM), Keynote Lecture, Jun. 12-22, 2011, Edmonton, Canada, vol. 2, p. 517-526.

Erickson et al. (2003) "Joule heating and heat transfer in poly(dimethylsiloxane) microfluidic systems," Lab Chip 3: 141-149.

Foote et al. (2005) "Preconcentration of proteins on microfluidic devices using porous silica membranes" Analyt. Chem. 77(1):57-63.

Giri et al. (2014) "Improvement in the sensitivity of microfluidic ELISA through field amplified sample stacking of the enzyme reaction product," Anal. Chim. Acta 810: 32-38.

Giri et al. (2015) "Undergraduate laboratory module for implementing ELISA on the high performance microfluidic platform," J. Chem. Educ. 92: 728-732.

Golnabi et al. (2007) "Oxygen sensing based on the oxidation process in resorufin dye" Sensors and Actuators B 122:109-117.

Gorman et al. (2006) "Tris(2,2'-bipyridyl)ruthenium(II) chemiluminescence," Analyst. 131:616-639.

Greulich et al. (2015) "N-Aminopyridinium salts as precursors for N-centered radicals—Direct amidation of arenes and heteroarenes," Org. Lett. 17: 254-257.

Han et al. (2009) "Surface-enhanced Raman scattering for protein detection," Anal. Bioanal. Chem. 394: 1719-1727.

Han et al. (2014) "Potential-resolved electrochemiluminescence for determination of two antigens at the cell surface," Anal. Chem. 86: 6896-6902.

He et al. (2009) "Design and testing of a microfluidic biochip for cytokine enzyme-linked immunosorbent assay" Biomicrofluidics 3(2):022401-1-022401-17.

Herr et al. (2007) "Microfluidic immunoassays as rapid saliva-based clinical diagnostics" PNAS 104(13):5268-5273.

Heyries et al. (2008) "Microfluidic biochip for chemiluminescent detection of allergen-specific antibodies" Biosensors and Bioelectronics 23(12):1812-1818.

Hofbeck et al. (2010) "The triplet state of fac-Ir(ppy)$_3$," Inorg. Chem. 49: 9290-9299.

International Search Report and Written Opinion Corresponding to International Patent Application No. PCT/US2010/043030 dated Nov. 23, 2010, 9 pp.

Invitrogen (2006) "Amplex Red Hydrogen Peroxide/Peroxidase Assay Kit Revised: 2006." http://probes.invitrogen.com/media/pis/mp22189.pdf 1-7.

Kakoti et al. (2013) "Heart type fatty acid binding protein: Structure, function and biosensing applications for early detection of myocardial infarction," Biosens. Bioelectron. 43: 400-411.

Kanda et al. (2004) "Label-free reading of microarraybased immunoassays with surface plasmon resonance imaging," Anal. Chem. 76: 7257-7262.

Kapturkiewicz (2016) "Cyclometalated iridium(III) chelates—a new exceptional class of the electrochemiluminescent luminophores," Anal. Bioanal. Chem. 408: 7013-7033.

Kapturkiewicz et al. (2005) "Electrochemiluminescence of the cyclometalated iridium(III) L$_2$Ir(acetyl acetonate) complexes," Electrochimica Acta. 50: 3395-3400.

Kemeny et al. (1989) "Ultrasensitive enzyme-linked immunosorbant assay (ELISA) for the detection of picogram of IgE.," J. Immunol. Methods 120: 251-258.

Khandurina et al. (1999) "Microfabricated porous membrane structure for sample concentration and electrophoretic analysis" Analyt. Chem. 71 (9):1815-1819.

Kim et al. (1999) "Photoinduced protein cross-linking mediated by palladium porphyrins," J. Am. Chem. Soc. 121: 11896-11897.

Kinde et al. (2013) "A microfluidic SPLITT device for fractionating low molecular weight samples," Anal. Chem. 85: 7167-7172.

Kinde et al. (2015) "Electrophoretic extraction of low molecular weight cationic analytes from sodium dodecyl sulfate containing sample matrices for their direct electrospray ionization mass spectrometry," Anal. Chem. 87: 2702-2709.

Knight et al. (1996) "Relationship between structural attributes and observed electrogenerated chemiluminescence (ECL) activity of

(56) References Cited

OTHER PUBLICATIONS tertiary amines as potential analytes for the tris(2,2-bipyridine)ruthenium(II) ECL reaction, A review," Analyst, 121: 101R-106R.
Koniev et al. (2015) "Developments of arecent advancements in the field of endogenous amino acid selective bond forming reactions for bioconjugation," Chem. Soc. Rev. 44: 5495-5551.
Koshi et al. (2008) "Target-specific chemical acylation of lectins by ligand-tethered DMAP catalysts," J. Am. Chem. Soc. 130: 245-251.
Kovarik et al. (2008) "Integrated nanopore/microchannel devices for ac electrokinetic trapping of particles" Analytical Chemistry 80(3):657-664.
Kraus et al. (2011) "Quantitative measurement of human anti-HCV Core immunoglobulins on an electrical biochip platform" Biosens. Bioelectron. 26(5):1895-1901.
Kricka et al. (2005) "The Immunoassay Handbook," in Chapter 11: Signal Generation and Detection Systems (Excluding Homogeneous Assays) 192-211.
Krishnan et al. (2014) "Design of reversible, cysteine-targeted Michael acceptors guided by kinetic and computational analysis," J. Am. Chem. Soc. 136: 12624-12630.
Kwee (1976) "The electrochemical reduction of disulfide bonds in proteins II," Bioelectrochemistry and Bioenergetics 3: 264-271.
Lee et al. (2008) "Increase of reaction rate and sensitivity of low-abundance enzyme assay using micro/nanofluidic preconcentration chip" Analyt. Chem. 80(9):3198-3204.
Leland et al. (1990) "Electrogenerated chemiluminescence: An oxidative-reduction type ECL reaction sequence using tripropyl amine," J. Electrochem. Soc. 137: 3127-3131.
Liu et al. (2009) "Microchip-based ELISA strategy for the detection of low-level disease biomarker in serum" Anal. Chim. Acta. 650(1):77-82.
Liu et al. (2012) "Diels-Alder Cycloaddition for Fluorophore Targeting to Specific Proteins Inside Living Cells," Journal of the American Chemical Society 134: 792-795.
Maruani et al. (2015) "A plug-and-play approach to antibody-based therapeutics via a chemoselective dual click strategy," Nature Commun. 6: 1-9.
Miao et al. (2002) "Electrogenerated chemiluminescence 69: The tris(2,2'-bipyridine)ruthenium(II), $(Ru(bpy)_3^{2+})$/Tri-n-propylamine (TPrA) system revisited—A new route involving TPrA$^{\cdot+}$ cation radicals," J. Am. Chem. Soc. 124: 14478-14485.
Miyaguchi et al. (2009) "Rapid analysis of methamphetamine in hair by micropulverized extraction and microchip-based competitive ELISA" Forensic Sci. Int. 184(1-3): 1-5.
Muzyka (2014) "Current trends in the development of the electrochemiluminescent immunosensors," Biosens. Bioelectron. 54: 393-407.
Nemzek et al. (2001) "Development and optimization of cytokine ELISAs using commercial antibody pairs," J. Immunol. Methods 255: 149-157.
O'donnell et al. (1967) "Controlled-potential oxidation of aliphatic amides," J. Electroanal. Chem. 13: 157-162.
Ohata et al. (Aug. 2017) "A hexa-rhodium metallopeptide catalyst for site-specific functionalization of natural antibodies," J. Am. Chem. Soc. 139: 12617-12622.
Palkar et al. (1997) "Mechanistic study of electrical field flow fractionation. 1. Nature of the internal field," Anal. Chem. 69: 3223-3230.
Palkar et al. (1997) "Mechanistic study of electrical field flow fractionation. 2. Effect of sample conductivity on retention," Anal. Chem. 69: 3230-3238.
Panish et al. (2013) "Enantioselective Synthesis of Cyclobutanes via Sequential Rh-catalyzed Bicyclobutanation/Cu-catalyzed Homoconjugate Addition," Journal of the American Chemical Society 135: 9283-9286.
Peek et al. (1991) "Synthesis of redox derivatives of lysine and related peptides containing phenothioazine or tris(2,2'-bypyiridine)ruthenium(II)," Int. J. Peptide Protein Res. 38: 114-123.
Pena et al. (2014) "A glass microchip device for conducting serological survey of West Nile viral antibodies," Biomed. Microdevices 16: 737-743.
Perich et al. (1987) "A New Convenient and Efficient General Procedure for the Conversion of Alcohols into Their Dibenxyl Phosphorotriesters Using N, N-Diethyl Dibenzyl Phosphoboramidite," Tetrahedron Lett. 28(1):101-102.
Prier et al. (2013) "Visible light photoredox catalysis with transition metal complexes: Applications in organic synthesis," J. Am. Chem. Soc. 113: 5322-5363.
Reichmuth et al. (2008) "Rapid microchip-based electrophoretic immunoassays for the detection of swine influenza virus" Lab on a Chip 8(8):1319-1324.
Reyes et al. (2002) "Micro Total Analysis Systems. 1. Introduction, Theory, and Technology," Anal. Chem. 74(12):2623-2636.
Richter (2004) "Electrochemiluminescence (ECL)," Chem. Rev. 104: 3003-3036.
Roggenbuck et al. (2012) "Antiphospholipid antibody profiling—Time for a new technical approach?" Autoimmun. Rev. 11: 821-826.
Romero et al. (2016) "Organic photoredox catalysis," Chem. Rev. 116: 10075-10166.
Ross et al. (1995) "Use of Bis[2-(trialkyllsiyl)ethyl] N, N-Dialkylphosphoramidites for the Synthesis of Phosphate Monoester," J. Chem. Soc. Perkin Trans. I 421-426.
Ross et al. (2001) "Temperature measurement in microfluidic systems using a temperature-dependent fluorescent dye," Anal. Chem. 73: 4117-4123.
Royzen et al. (2011) "Total Synthesis of Hyacinthacine A2: Stereocontrolled 5-azacyclooctene Photoisomerization and Transannular Hydroamination with Planar-to-Point Chirality Transfer," Chemical Science 2: 2162.
Rubinstein et al. (1981) "Electrogenerated chemiluminescence. 37. Aqueous Ecl systems based on $Ru(2,2'-bipyridine)_3^{2+}$ and oxalate or organic acids," J. Am. Chem. Soc. 103: 512-516.
Schlick et al. (2005) "Dual-surface modification of the tobacco mosaic virus," J. Am. Chem. Soc. 127: 3718-3723.
Schroeder et al. (1978) "Chemiluminescence Yields and Detection Limits of Some Isoluminol Derivatives in Various Oxidation Systems," Anal. Chem 50(8):1114-1120.
Seitchik et al. (2012) "Genetically Encoded Tetrazine Amino Acid Directs Rapid Site-Specfic In Vivo Biorthogonal Ligation," Journal of the American Chemical Society 134: 2898-2901.
Smith et al. (2016) "Analytically useful blue chemiluminescnce from a water-soluble iridium(III) complex containing a tetraethylene glycol functionalized triazolylpyridine ligand," Analyst. 141: 2140-2144.
Song et al. (2004) "Miniature biochip system for detection of *Escherichia coli* O157:H7 based on antibody-immobilized capillary reactors and enzyme-linked immunosorbent assay" Analytica Chimica Acta 507(1): 115-121.
Stratis-Cullum et al. (2008) "Intensified biochip system using chemiluminescence for the detection of Bacillus globigii spores" Analytical and Bioanalytical Chemistry 391(5): 1655-1660.
Sun et al. (2005) "Reduction-alkylation strategies for the modification of specific monoclonal antibody disulfides," Bioconjugate Chem. 16: 1282-1290.
Taylor et al. (2011) "Design and Synthesis of a Highly Reactive Dienophile for the Tetrazine-trans-Cyclooctene Ligation," Journal of the American Chemical Society 133: 9646-9649.
Taylor et al. (2015) "Biosynthesis of the C15-acetogenin laurepoxide may involve bromine-induced skeletal rearrangement of a Δ4-oxocene precursor," Tetrahedron Letters 56: 3560-3563.
Terry et al. (2005) "The application of biosensors to fresh produce and the wider food industry," J. Agric. Food Chem. 53: 1309-1316.
Thomas et al. (2004) "Bead-based electrochemical immunoassay for bacteriophage MS2" Anal. Chem. 76(10):2700-2707.
Toh et al. (2010) "A low molecular weight cut-off polymer-silicate membrane for microfluidic applications," Microfluid. Nanofluid. 9: 1135-1141.
Tokel et al. (1972) "Electrogenerated chemiluminescence. IX. Electrochemistry and emission from systems containing tris(2,2'-bipyridine)ruthenium(II) dichloride," J. Am. Chem. Soc. 94: 2862-2863.

(56) References Cited

OTHER PUBLICATIONS

Topol et al. (2001) "Experimental determination and calculations of redox potential descriptors of compounds directed against retrovial zinc fingers: Implications for rational drug design," Protein Sci. 10: 1434-1445.

Treiber et al. (1997) "Chemical and Biological Oxidation of Thiophene: Preparation and Complete Characterization of Thiophene S-Oxide Dimers and Evidence for Thiophene S-Oxide as an Intermediate in Thiophene Metabolism in Vivo and in Vitro," J. Am. Chem. Soc. 119(7):1565-1571.

Tucker et al. (2012) "Shining light on photoredox catalysis: Theory and synthetic applications," J. Org. Chem. 77: 1617-1622.

USPTO "Non-Final Office Action," dated Sep. 17, 2012, corresponding to U.S. Appl. No. 12/842,526, 7 pp.

USPTO "Notice of Allowability," dated Mar. 26, 2013, corresponding to U.S. Appl. No. 12/842,526, 6 pp.

USPTO "Requirement for Restriction/Election," dated Feb. 10, 2012, corresponding to U.S. Appl. No. 12/842,526, 8 pp.

Wang et al. (1997) "Low Temperature Bonding for Microfabrication of Chemical Analysis Devices," Sens. Actuators B 45: 199-207.

Wang et al. (2005) "Million-Fold Preconcentration of Proteins and Peptides by Nanofluidic Filter" Analytical Chemistry 77(14):4293-4299.

Wang et al. (2010) "Study on the kinetics of homogeneous enzyme reactions in a micro/nanofluidics device" Lab on a Chip 10(5):639-646.

Wang et al. (2011) "Chemical cell-surface receptor engineering using affinity-guided multivalent organocatalysts," J. Am. Chem. Soc. 133: 12220-12228.

Wang et al. (2012) "Battery-triggered microfluidic paper-based multiplex electrochemiluminescence immunodevice based on potential-resolution strategy," Lab Chip. 12: 4489-4498.

Wu et al. (2009) "High speed nanofluidic protein accumulator" Lab on a Chip 9(13): 1890-1896.

Xuan et al. (2004) "Electroosmotic flow with Joule heating effects," Lab Chip 4: 230-236.

Yanagisawa et al. (2011) "Kinetic ELISA in microfluidic channel," Biosensors 1: 58-69.

Yanagisawa et al. (2011) "Multiplex ELISA in a single microfluidic channel," Analytical and Bioanalytical Chemistry 401(4): 1173-1181.

Yanagisawa et al. (2012) "Enhancement in the sensitivity of microfluidic enzyme-linked immunosorbent assays through analyte pre-concentration", Analytical Chemistry 84(16): 7029-7036.

Yanagisawa et al. (2014) "Microfluidic enzyme-linked immunosorbent assay in a region of finite length" Analytica Chimica Acta 817: 28-32.

Yang et al. (2010) "Lab-on-a-chip for carbon nanotubes based immunoassay detection of Staphylococcal Enterotoxin B (SEB)" Lab on a Chip 10:1011-1017.

Yu et al. (2008) "A simple, disposable microfluidic device for rapid protein concentration and purification via direct-printing" Lab on a Chip 8(9):1496-1501.

Yu et al. (2012) "Photophysics, electrochemistry and electrochemiluminescence of water-soluble biscyclometalated iridium(III) complexes," J. Organometallic Chem. 718: 14-21.

Zhang et al. (2014) "Cu-Catalyzed Cascades to Carbocycles: Union of Diaryliodonium Salts with Alkenes or Alkynes Exploiting Remote Carbocations," Journal of the American Chemical Society 136: 8851-8854.

Zhou et al. (2003) "Multilabeling biomolecules at single site. 1. Synthesis and characterization of a dendritic label for electrochemiluminescence assays," Anal. Chem. 75: 6708-6717.

Zhou et al. (2014) "Synthesis, labeling and bioanalytical applictions of a tris(2,2'-bipyridyl0ruthenium(II)-based electrochemiluminescence probe," Nature Protocols 9: 1146-1159.

Zuo et al. (2014) "Decarboxylateive arylation of α-amino acids via photoredox catalysis: A one-step conversion of biomass to drug pharmacaphore," J. Am. Chem. Soc. 136: 5257-5260.

\* cited by examiner glass chip with no electrodes electrode on the bottom channel wall glass chip with gold electrodes (a) Canonical ECL conditions (b) Current art: Reporter Antibodies via non-specific lysine modification:

(c) Specific Aim 2:

Figure 10. Voltage mediated multiplexing-ECL.

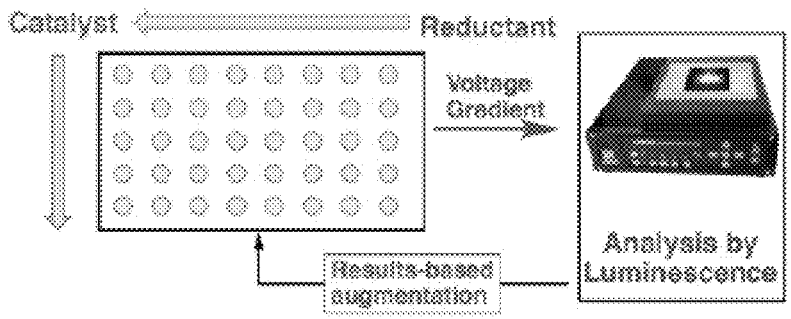
Figure 11A
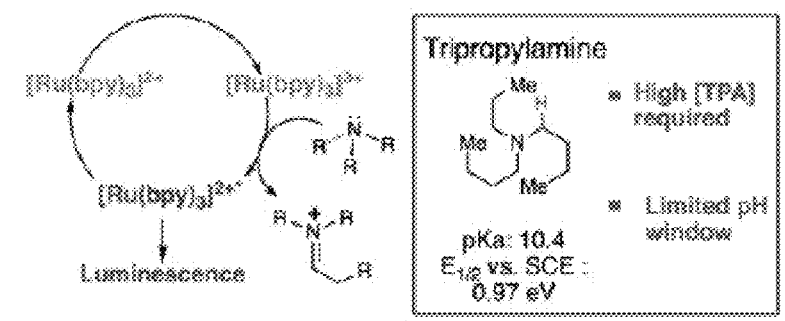
Figure 11B
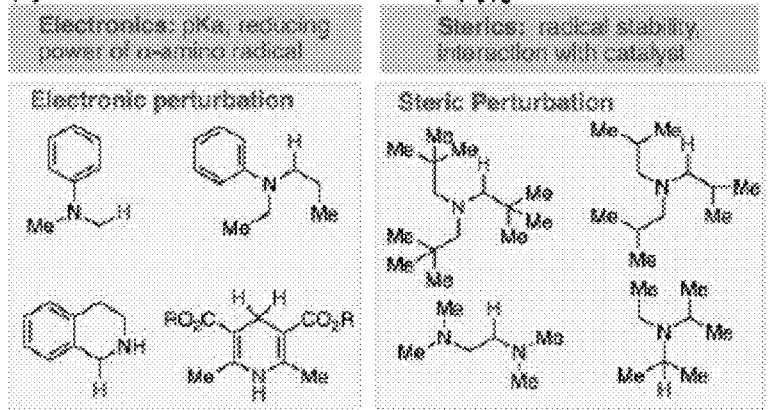
Figure 11C
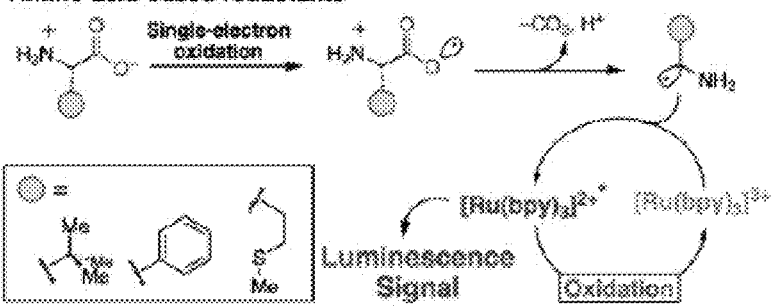

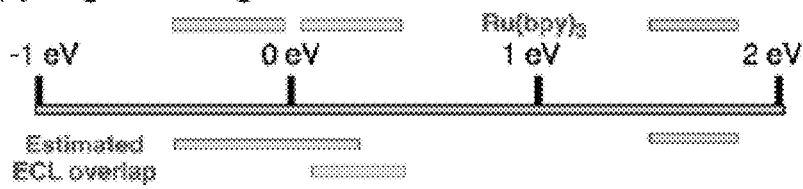
Figure 12A
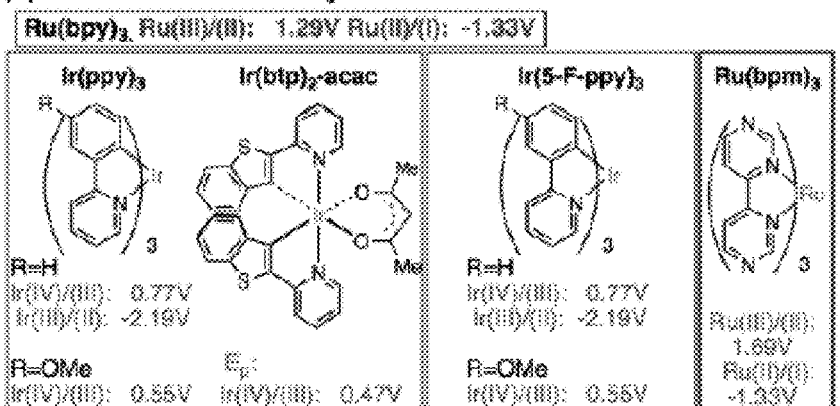
Figure 12B
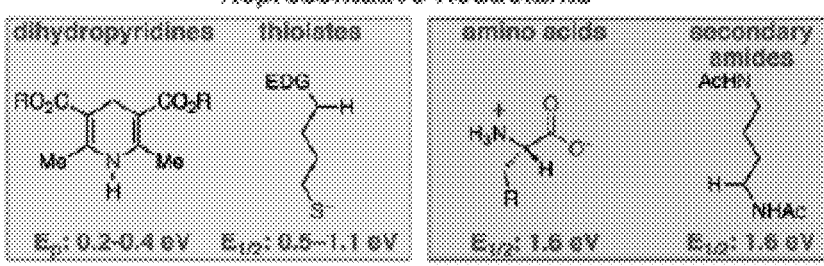
Figure 12C
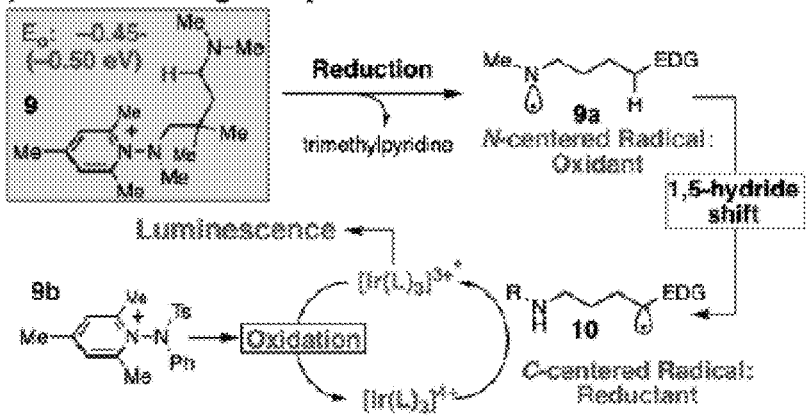

| | | | |
|---|---|---|---|
| A | "Elisa" Region | F | waste channel |
| B | microfluidic side channel | G | electrode |
| C | semipermeable membrane | H | multipurpose reservoir |
| D | electrode | J | downstream channel (optional) |
| E | detection device | K | auxiliary channel (optional) |

METHODS AND DEVICES FOR DETECTION OF BIOLOGICAL MATERIALS USING ELECTRIC FIELD ASSISTED RAPID ANALYTE CAPTURE

CROSS-REFERENCE TO RELATED APPLICATIONS

This application claims the benefit of U.S. Provisional Application Ser. No. 62/647,330, filed Mar. 23, 2018, which is hereby incorporated by reference in its entirety, to the extend not inconsistent herewith.

STATEMENT REGARDING FEDERALLY SPONSORED RESEARCH OR DEVELOPMENT

This invention was made with government support under DBI 0964211 awarded by the National Science Foundation and 1R15AG045755-01A1 awarded by the National Institutes of Health. The government has certain rights in the invention.

BACKGROUND

Immunoassays offer a powerful approach to quantitating a variety of biological substances such as proteins, peptides, antibodies, hormones, etc., in complex matrices. Proteins can serve as valuable biomarkers in view of their high specificity, involvement in many biological processes, and information they can provide about alternative splicing and posttranslational modifications. Physiological changes such as signal transduction, cell differentiation, and malignant transformation are not necessarily detectable at the nucleic acid level. However, there are challenges for microfluidics-based protein detection. First, proteins are much more diverse than DNAs and RNAs in both numbers (~300,000 to several millions) and sizes (tens to ~36,000 amino acids). Second, proteins of clinical interest are usually in low abundance compared to those on the background in biological samples, while there is no amplification process equivalent to PCR for nucleic acids. To address these challenges, immunoaffinity-based techniques ("immunoassays") have been miniaturized onto microfluidic devices for detection and quantification of target proteins by exploiting the high sensitivity and specificity of antibody-antigen interactions.

The utility of this technique in bioanalytical applications comes from its high specificity based on the antigen-antibody reaction and low analyte detection limit arising from the highly sensitive reporter systems integrated to the assay. In the case of Enzyme-Linked ImmunoSorbent Assays (ELISA), for example, actual signal amplification is realized through an enzyme reaction allowing for a continuous generation of the reporting species for every binding event between an antigen and the antibodies. Similarly, multiple excitation cycles are employed in electrochemiluminescent immunoassays to realize comparable, if not better, signal-to-noise ratios. Besides their high sensitivity and specificity, immunoassays also tend to be relatively simple to implement and involve only a series of washing and incubation steps prior to their final quantitation, usually by an optical or electrochemical detection method. For these reasons, immunoassays, and in particular, ELISAs are widely accepted as gold standards for analyzing samples relevant to fundamental biological research, biomedical testing, environmental monitoring and food assessment applications among others.

In spite of these merits, the capabilities of modern immunoassays have proven insufficient for some particularly demanding sample analysis in terms of sensitivity, assay time and/or sample size. As a result, there is a need to miniaturize these bioanalytical methods cutting down their sample volume requirement, shorten their sample incubation periods to reduce the assay time and further improve their analyte detectability, possibly without compromising the simplicity or the lower cost of the assay. Microfluidics ELISA systems have been developed which address some of the issues pointed out above. Microfluidics provide for smaller sample volumes, lower reagent volumes, and faster analysis. However, there is still a need in the art to provide further improvements in speed and sensitivity of microfluidics ELISAs.

SUMMARY

In one embodiment, the present invention includes a system for detecting a target analyte. The system includes a system for detecting a target analyte, comprising a microfluidic device which includes: (a) at least one microfluidic channel; and (b) a binding surface positioned in the microfluidic channel wherein at least a portion of the binding surface has channel walls comprising electrodes comprising a first electrode and a second electrode. In embodiments, the system further comprises (c), a detector positioned to detect a signal generated by the presence of the target analyte. In embodiments the system further includes a voltage supply in electrical communication with the first and second electrodes in the at least one microfluidic channel.

The system of the invention may further comprise a solution in the microfluidic device comprising a target analyte and a reporter molecule. In embodiments, reporter molecule is a reporter antibody-catalyst conjugate capable of catalyzing electrochemiluminescence reactions.

In embodiments, the system further comprises a system comprising a microfluidics trapping system as disclosed in U.S. Pat. No. 8,507,208, which is incorporated herein by reference for all that is taught and disclosed. The system of the invention may therefore further include (d) at least two microfluidic side channels positioned in fluid communication with the at least one microfluidic channel; (e) a semipermeable membrane positioned in a first of the at least two of microfluidic side channels, the semipermeable membrane having a surface oriented towards the microfluidic channel; (f) a third electrode positioned in the first of the at least two of microfluidic side channels, and positioned such that the semipermeable membrane is positioned between the third electrode and the microfluidic channel; and (g) a fourth electrode positioned in the microfluidic channel or in a second of the at least one of microfluidic side channels; wherein (d), (e), (f) and (g) are positioned upstream of a detector. The semipermeable membrane may comprise a silicate and a polymer.

In embodiments, the present invention also comprises a method to detect a target analyte in a sample. The method includes the following steps. Step (a) includes providing a microfluidic device comprising a binding surface in at least one microfluidic channel, wherein at least a portion of the binding surface has channel walls comprising electrodes comprising a first electrode and a second electrode, wherein the binding surface comprises binding molecules capable of selectively binding to the target analyte; and step (b) includes introducing to the binding surface a first solution comprising the target analyte molecules, wherein at least a portion of the target analyte molecules can selectively bind to the binding molecules of the binding surface to provide a binding surface having bound target analyte molecules. The method further includes step (c) which includes binding the target analyte to the binding surface by applying an electrical potential between the first and second electrodes during at least a portion of the binding step, thereby enhancing the rate of binding of the target analyte molecules to the binding molecules. The method also includes (d) providing to the binding surface having the bound target analyte molecules a second solution comprising second binding molecules optionally including at least one reporter molecule, or third binding molecules optionally including at least one reporter molecule, wherein at least a portion of the second or third binding molecules further bind directly or indirectly to the target analyte molecules bound to the binding surface; wherein the reporter molecules can directly or indirectly generate a detectable signal. The method then further comprises a step (e) which includes detecting the signal indicating an amount of the originally present target analyte molecules in the sample.

In embodiments, steps (b) and (c) are performed with additional aliquots of solutions (or aliquots) comprising the target analyte solution at least two times prior to performing step (d). Steps (b) and (c) can be performed at least five times, at least ten times, at least twenty times, at least thirty times, at least forty times, at least fifty times, at least sixty times or more prior to performing step (d) of the method.

In embodiments, the method of performing steps (b) and (c) of the method at least two times or more results in at least 10 times more, 100 times more, 500 times more, or more, target analyte molecule is bound to the binding surface compared with binding the target analyte molecule in the absence of an applied electric field between the first and second electrodes.

In embodiments, the amount of time required to bind a specified amount of target analyte molecule applied to the binding surface is reduced by approximately ten fold, twenty fold, or sixty fold, compared with binding the target analyte molecule in the absence of an applied electric field between the first and second electrodes.

In specific embodiments, the binding surface may be a derivatized glass, for example, derivatized with a silane compound and/or an aldehyde compound, such as 3-aminopropyltriethoxysilane and the aldehyde compound is glutaraldehyde. The binding molecule capable of selectively binding to the target analyte may be an antibody with specificity for binding the target analyte. In embodiments, after binding the binding molecule to the binding surface, the method further comprises blocking nonspecific binding sites on the binding surface by applying a solution comprising a peptide, a polypeptide, or a combination thereof following step (a). The method can also include steps of removing nonspecifically bound and/or unbound target analyte following step (c).

In embodiments, the first, second and/or third binding molecule are the same or different, and can be an antibody, an aptamer, antigens of antibodies, biotin, streptavidin, nucleic acids, peptide nucleic acids; conjugates between antigens of antibodies, streptavidin, or any combination of these. The reporter molecules may be conjugated to the first, second, or third binding molecule by any means known in the art. Reporter molecules, for example, include a catalytically active group, such as, for example, alkaline phosphatase, acid phosphatase, horseradish peroxidase, beta-galactosidase, glucose oxidase, carboxypeptidase B, porcine liver esterase, rabbit esterase, lipase, butyryl cholinesterase, arginase, a catalyst for a bond cleavage reaction, a catalyst for a bond forming reaction, a catalyst for an oxidation reaction, a catalyst for a reduction reaction or any combination of these.

In one embodiment, the reporter molecule is a catalyst capable of electrochemiluminescence reactions. In this embodiment, the catalyst molecule is tris(bipyridine) ruthenium (II) chloride, or $Ru(bpy)_3$. Where the method encompasses a catalyst capable of electrochemiluminescence reactions, the method can include applying an electrical potential between the first and second electrodes after the reporter molecule binding step (d) in an amount capable of eliciting a electrochemiluminescence reaction, and wherein the detecting step (e) comprises detecting an electrochemiluminescence reaction.

In another embodiment, the reporter molecule is capable of creating a colored or fluorescent ionized product molecule from a precursor to a colored or fluorescent product molecule (e.g., a substrate).

In embodiments, the methods of the invention further include the following steps. In one step, step (e) includes providing to the binding surface having the bound target analyte molecules and/or the bound reporter molecules a solution comprising substrate molecules, wherein at least a portion of the substrate molecules undergo a catalytic chemical reaction initiated by a reporter molecule, thereby producing reaction product molecules having an ionic charge different from an ionic charge of the substrate molecules. The method may then further include the step (f) which includes transporting at least a number of the reaction product molecules into a microfluidic trapping region in fluid communication with the microfluidic binding region. The method may further include step (g), concentrating the reaction product molecules in the microfluidic trapping region in front of, at the surface of and/or within a semipermeable membrane; wherein the signal is measured from the reaction product molecules in front of, at the surface of and/or within a semipermeable membrane.

In embodiments, transporting step (f) may include applying an electric potential between a third electrode positioned in a first microfluidic side channel and a fourth electrode positioned in the microfluidic channel or in a second microfluidic side channel, wherein the semipermeable membrane is positioned in a first microfluidic side channel between the third electrode and the microfluidic channel and having a surface oriented towards the microfluidic channel. In this embodiment, the electrical potential provides a force attracting the reaction product molecules towards the microfluidic trapping region. In the methods, the step (g) of measuring the reaction product molecules is performed after one or more time intervals which are appropriate for the reaction, as determined by one of skill in the art.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

BRIEF DESCRIPTION OF THE DRAWINGS

FIG. 11A shows a high throughput strategy to rapidly assess catalyst/reductant pairs.

FIG. 11B shows current ECL prerequisites.

FIG. 11C shows a strategy for optimization of ECL.

FIG. 12A shows a rapid output screening for catalyst/reductant optimization.

FIG. 12B shows targeted voltage windows and potential representative reductants.

FIG. 12C shows a strategy for reduction/oxidation ECL.

DETAILED DESCRIPTION

Figure 1A:
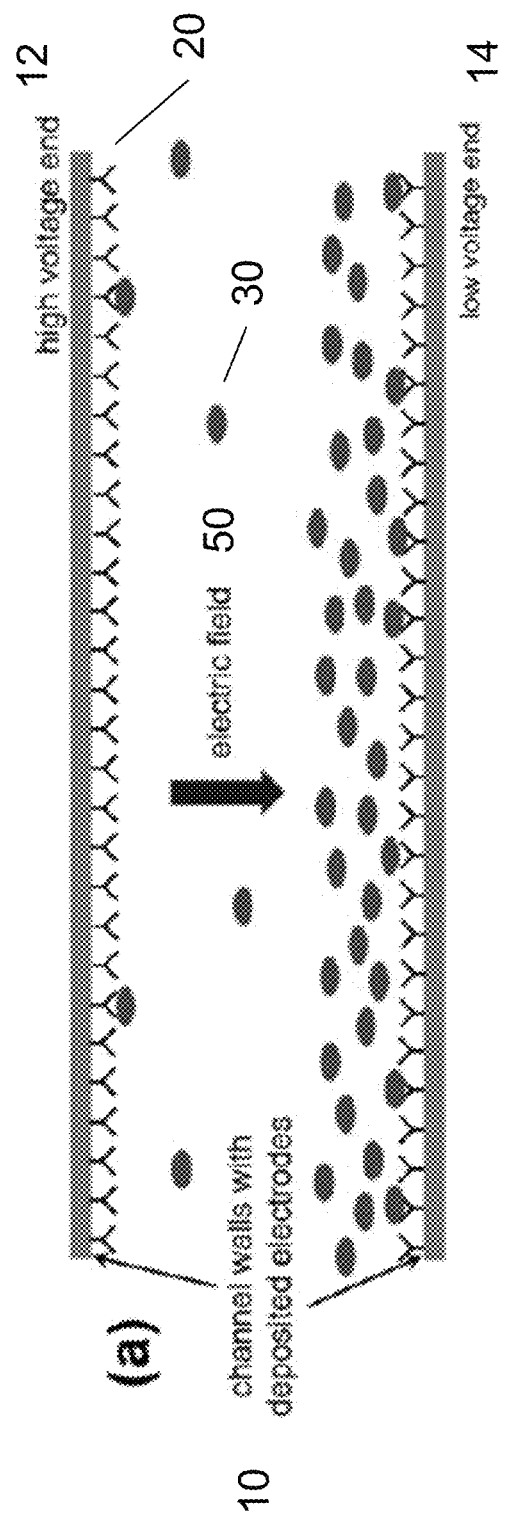
FIG. 1A provides a schematic illustration of the antigen capture process in the presence of a lateral electric field in a microfluidic channel.

In general the terms and phrases used herein have their art-recognized meaning, which can be found by reference to standard texts, journal references and contexts known to those skilled in the art.

In the present invention, in order to improve sensitivity, decrease assay time and/or decrease sample size, the present inventors have developed a novel microfluidic immunoassay platform with analyte detection limits that are over 3-4 orders of magnitude lower than that realizable using current ELISA or electrochemiluminescence immunoassay systems. These immunoassays, which are referred to herein as Electric Field Assisted Rapid Analyte Capture (EFARAC) immunoassays, are performed over an electrode surface embedded in the assay chamber, e.g., a glass microchannel, to allow for rapid capture of antigens using a lateral electric field (see FIG. 1($a$)). The results demonstrate that the inventive approach to performing immunoassays opens up several avenues to improving their sensitivity. Firstly, the analyte detectability was observed to improve by about 4-fold in the system even without application of any electric fields just due to optical reflection of the luminescent light (from the reporter species) by the metallic electrode surfaces. Next, the application of an optimum voltage drop across the microelectrodes during the sample incubation period further improved the assay sensitivity by an additional 4.5-fold likely due to a more efficient antigen capture on one of the electrode surfaces. For a human TNF-α sample as used in the preliminary work, the electrode with the negative electrical polarity was observed to capture most of the antigenic species in the experiments. But more importantly, it was discovered that this electric field assisted antigen capture process was mostly completed within a minute of sample incubation likely due to electrokinetic focusing of the antigen molecules over the negatively charged electrode. In this situation, the present inventors were able to incubate multiple sample aliquots against the assay surface enabling the capture of even more analyte molecules on it but without prolonging the overall assay time. In preliminary work, this strategy allowed the inventors to realize another 51-fold reduction in the analyte detection limit through incubation of 60 sample aliquots for a minute each over an hour long total incubation time. Overall, the present inventors were able to detect human TNF-α at a concentration about 918-fold (2.5 fg/mL versus 2.3 pg/mL) lower than that possible using a commercial TNF-α ELISA kit.

Building on these results, the EFARAC immunoassay method may be further developed to improve its sensitivity and dynamic range. In a particular embodiment, the electrodes employed for the analyte capture process in our device can be readily used for triggering electrochemiluminescence (ECL) reactions, thus the present invention also includes an embodiment wherein ECL detection methods are used to further broaden the present invention's capabilities for making analytical measurements.

In an additional embodiment, the present invention provides an embodiment wherein detection capabilities of ECL immunoassays is improved through the use of rational chemical design. Current ECL immunoassays utilize chemical techniques to generate reporter antibodies that are comparatively crude by modern standards. Moreover, while the number of chemically distinct ECL reactions is increasing, the number that are actually amenable to immunoassay conditions presents a bottleneck with respect to the throughput capabilities of ECL immunoassays. Therefore, as discussed in more detail hereinbelow the present invention also includes new chemical techniques that will allow for the generation of reporter antibodies with enhanced chemical homogeneity and ECL performance. The present invention may also be used together with ECL reaction systems that will allow for ECL multiplexing. Taken together, the methods taught by the present invention outperform current microfluidics ELISA and ECL systems in terms of sensitivity, and the resulting platform is more portable and yields broader multiplexing capabilities.

The invention provides improvements to ELISA-type assays. As known in the art, ELISAs are a robust platform for measuring analytes of interest. In general, the format used for an ELISA includes immobilization of the target analyte such as an antigen of interest, which can be accomplished by direct adsorption to the assay plate or indirectly via a binding molecule such as a capture antibody that has been attached to the plate. The target analyte such as an antigen is then detected either directly (e.g., through a second binding molecule-reporter molecule such as a labeled primary antibody) or indirectly (e.g., through a second binding molecule-reporter molecule such as labeled secondary antibody). An ELISA assay format is the sandwich assay. This type of capture assay is called a "sandwich" assay because the analyte to be measured is bound between two primary antibodies—the capture antibody and the detection antibody. The sandwich format is used because it is sensitive and robust. The direct detection method uses a labeled primary antibody that reacts directly with the antigen. Direct detection can be performed with an antigen that is directly immobilized on the assay plate or with the capture assay format. Direct detection while not widely used in ELISA is quite common for immunohistochemical staining of tissues and cells. The indirect detection method uses a labeled secondary antibody for detection and is the most popular format for ELISA. The secondary antibody has specificity for the primary antibody. In a sandwich ELISA, it is critical that the secondary antibody be specific for the detection primary antibody only (and not the capture antibody) or the assay will not be specific for the antigen. Generally, this is achieved by using capture and primary antibodies from different host species (e.g., mouse IgG and rabbit IgG, respectively). For sandwich assays, it is beneficial to use secondary antibodies that have been cross-adsorbed to remove any secondary antibodies that might have affinity for the capture antibody.

In one embodiment, the present invention provides a method to detect a target analyte in a sample, the method including the following steps.

In a first step, the method includes a step (a) of providing a microfluidic device comprising a binding surface in at least one microfluidic channel, wherein at least a portion of the binding surface has channel walls comprising electrodes comprising a first electrode and a second electrode, wherein the binding surface comprises binding molecules capable of selectively binding to the target analyte.

In one embodiment, the terms "analyte" and "target analyte" refer to a molecule, compound, or species of interest which is present in a sample. In certain embodiments, the presence and/or amount of an analyte or target analyte in a fluid is indicative of a condition in a system from which the fluid is obtained. As used herein, an analyte (or target analyte) may include one or more species of one or more of the following: a protein, a peptide, a polypeptide, an amino acid, a nucleic acid, an oligonucleotide, a therapeutic agent, a metabolite of a therapeutic agent, RNA, DNA, an antibody, an organism, a virus, bacteria, a carbohydrate, a polysaccharide, and glucose. An analyte may also include, for example, a lipid, a gas (e.g., oxygen, carbon dioxide), an electrolyte (e.g., sodium, potassium, chloride, bicarbonate, BUN, creatinine, glucose, magnesium, phosphate, calcium, ammonia, lactate), a lipoprotein, cholesterol, a fatty acid, a glycoprotein, a proteoglycan, and/or a lipopolysaccharide.

In one aspect, the method can be used to quantify the amount of analyte that was in the sample, generally a fluid or liquid sample. The sample can be derived from a biological fluid such as, for example, blood, a cell homogenate, a tissue homogenate, a cell extract, a tissue extract, a cell suspension, a tissue suspension, milk, urine, saliva, semen or spinal fluid. The sample may be a gaseous or solid material that is resuspended or dissolved in water, buffered saline and the like.

The phrase "quantifying an analyte" (and similar statements) is defined herein as calculating the amount of analyte present in a known volume of sample once the analyte has been treated by methods of the invention. In one aspect, the analyte is quantified by detecting and counting the reporter molecules and/or reaction product molecules created therefrom and correlating the amount to a corresponding concentration of target analyte based on the known volume of the sample and a standard curve prepared by using controls having known amounts of target analyte. The ratio of detected signal when a target analyte is present in the interrogation volume to the detected signal in the absence of a target analyte is defined as the signal-to-noise ratio (SNR). The detected signal can be based simply on intensity at a certain wavelength, or a complex parameter involving intensity, multiple wavelengths, phase, timing, etc. The required SNR is a function of instrumentation design and assay requirements.

The methods described herein for quantifying analytes permit the rapid analysis of the analyte. In one aspect, the analysis of the analyte can be performed in less than 30 minutes. In another aspect, the analysis of the analytes do not require target molecular amplification or multiplication (e.g., polymerase chain reaction (PCR)) for high sensitivity, which provides improved precision and accuracy. Numerous other advantages are described below.

"Microfluidic device" refers to a system containing liquid constrained in at least one physical dimension generally of the order of nanometers to millimeters. In some embodiments, the liquid is constrained to a lateral dimension selected between 1 nm and 1 cm, such as a narrower lateral dimension (e.g., depth) selected over the range of 1 nm to 5 mm, 100 nm to 100 µm or 500 nm to 50 µm, and a wider lateral dimension (e.g., width) selected over the range of 1 nn to 1 cm, 10 µm to 2 mm or 1 µm to 10 mm. In embodiments, an axial (e.g., flow) direction in a microfluidic device can be long, for example on the order of meters, but will more commonly be 0.1 cm to 10 cm or 1 cm to 5 cm. Microfluidics are distinguished herein from macrofluidics.

A "channel" of the device, such as a "microfluidic channel" or "main microfluidic channel" refers to a specific portion of a microfluidic device. In one embodiment, a microfluidic channel is generally observed to contain the majority of fluid in a flowing system. In embodiments, a microfluidic channel has a flow axis with optionally one or more microfluidic side channels each having a flow axis which is non-parallel (e.g., perpendicular) to the flow axis of the microfluidic channel. "Microfluidic side channel" refers to a specific portion of a microfluidic device. In one embodiment, a microfluidic side channel is generally observed to contain only a small amount of the total flow of fluid in a flowing system. In one embodiment, a microfluidic side channel in a flowing system does not exhibit flow as found in other parts of the corresponding flowing system, but may be characterized as having atoms, molecules or ions which move via diffusion or electrophoresis.

"Microfluidic trapping region" or "binding surface" refers to a specific portion of a microfluidic device occurring in a microfluidic channel. In embodiments, a microfluidic trapping region is a portion of a microfluidic device which is used to collect or otherwise contain a specific molecule, ion or atom of interest. "Binding surface" refers to a portion of an object to which molecules or atoms bind. In some embodiments a binding surface is that part of an object which is functionalized or otherwise preferentially utilized to bind molecules or atoms. The binding surface can include glass, such as a borosilicate glass, and is optionally derivatized. For example, silanol groups on $SiO_2$ surfaces react with alkoxysilanes forming a stable covalent bond which is then capable of binding to carboxyl-groups for protein or antibody attachment as is known in the art. In one embodiment, the alkoxysilane is a trialkoxysilane with an amine functional group, such as 3-aminopropyltriethyoxysilane. The functionalized glass may be further treated with a bi-functional linker, such as glutaraldehyde, to immobilize the binding proteins on to the surface of the channels, using conditions known in the art.

The binding surface preferably forms a rigid support on which a reactant can be immobilized. The reaction site surface is also chosen to provide appropriate characteristics with respect to interactions with light. For instance, the reaction site may be functionalized glass, Si, Ge, GaAs, GaP, SiO2, $SiN_4$, modified silicon, or any one of a wide variety of gels or polymers such as (poly)tetrafluoroethylene, (poly) vinylidenedifluoride, polystyrene, polycarbonate, polypropylene, or combinations thereof. Other appropriate materials may be used in accordance with the present invention. A transparent reaction site may be advantageous. In addition, in the case where there is an optically transmissive 'window" permitting light to reach an optical detector, the surface may be advantageously opaque and preferentially light scattering.

One skilled in the art will appreciate that there are many ways of immobilizing various reactants onto a support where reaction can take place. The immobilization may be covalent or non-covalent, via a linker moiety, or tethering them to an immobilized moiety. These methods are well known in the field of solid phase synthesis and micro-arrays (Beier et al., Nucleic Acids Res. 27:1970-1-977 (1999). Non-limiting exemplary binding moieties for attaching either nucleic acids or proteinaceous molecules such as antibodies to a solid support include streptavidin or avidin/biotin linkages, carbamate linkages, ester linkages, amide, thiolester, (N)-functionalized thiourea, functionalized maleimide, amino, disulfide, amide, hydrazone linkages, and among others. In addition, a silyl moiety can be attached to a nucleic acid directly to a substrate such as glass using methods known in the art. Surface immobilization can also be achieved via a Poly-L Lysine tether, which provides a charge-charge coupling to the surface. Regarding proteins in particular, proteins naturally contain amine, sulfhydryl, and carboxylic acid functional groups.

The aminosilanization of the glass surface by treatment with 3-(aminopropyl) trimethoxysilane (APTMS) affords a positively charged surface with available amino groups. Fixe et al. reported the aldehyde modification using glutaraldehyde. As shown in Scheme 1, the amine-modified surface can then be treated with glutaraldehyde (for example, 5% v/v in 0.1 M PBS for 2 h at room temperature. Glutaraldehyde covalently immobilized to the support is bi-functional linker which can also react with proteins to immobilize them on to the surface.

"Bind" refers to a process in which an ion, atom or molecule is attached to a surface or otherwise held in the vicinity of a surface. "Selectively bind" refers to a process in which only a specific atom or molecule is induced to bind to a surface. Direct binding refers to a situation where a molecule, atom or ion binds to a surface with no intervening moiety; indirect binding refer to the binding of a molecule, atom or ion to other moieties attached to or otherwise bound to a surface.

"Binding molecules" and "second (or third) binding molecules" includes, in embodiments, molecules, materials or structures capable of nonselectively or preferably, selectively binding with the target analyte molecules and/or molecules bound or indirectly bound to target analyte molecules. In exemplary embodiments, the binding molecules comprise antigens of antibodies, antibodies, biotin, streptavidin, aptamers, nucleic acids, peptide nucleic acids; conjugates between antigens of antibodies, antibodies, biotin, streptavidin, aptamers, nucleic acids, peptide nucleic acids; or any combination of these. A first binding molecule and a second (or third) binding molecule may be the same or different.

As noted herein, the binding surface will comprise a first and second electrode in fluid and electrostatic communication with the microfluidic channel capable of creating a lateral electric field within the channel comprising the binding surface. The electrodes will comprise an anode and/or a cathode. Each electrode may become either the anode or the cathode depending on the direction of current through the cell. An electrode useful in the present invention can include an thin-film layer electrode formed by methods known in the art, of, for example, an inert electrode material such as gold or platinum. In embodiments, a chromium layer is deposited first and then covered with a layer of gold.

"Electrode" refers to an electrical conductor that is used to make contact with a nonmetallic part of a circuit, e.g., a semiconductor, an electrolyte, vacuum, or air. An electrode in an electrochemical cell is referred to as either an anode or a cathode. The anode is now defined as the electrode at which electrons leave the cell and oxidation occurs (indicated by a minus symbol, "−"), and the cathode as the electrode at which electrons enter the cell and reduction occurs (indicated by a plus symbol, "+"). Each electrode may become either the anode or the cathode depending on the direction of current through the cell. An electrode useful in the present invention include an thin-film layer formed by methods known in the art, of an inert electrode material such as gold or platinum. In embodiments, a chromium layer is deposited first and then covered with a layer of gold. The term "electrophoresis", as used herein, refers to the motion of particles or ions in a liquid by an electric field. The electrodes as disclosed herein are preferably in fluid communication and electrostatic communication with the components of the devices of the invention. "Fluid communication" refers to the relative orientation of two or more components such that an uninterrupted fluid path exists between the components. "Electrostatic communication" refers to the relative orientation of two or more components such that an electric field is provided between the components, such as a uniform electric field. "Electrical contact" and "electrical communication" refers to the arrangement of one or more objects such that an electric current (e.g., a flow of electrons or ions) flows from one object to another.

A binding molecule immobilized at a binding site can be anything useful for detecting an analyte of interest in a sample of bodily fluid. For instance, as disclosed above, such binding molecules include without limitation nucleic acid probes, antibodies, cell membrane receptors, monoclonal antibodies and antisera reactive with a specific analyte. Various commercially available reactants such as a host of polyclonal and monoclonal antibodies specifically developed for specific analytes can be used.

The term "antibody" as used herein is intended to be consistent with use of the term in the fields of biology, immunology, biochemistry, etc. The term antibody generally refers to a protein which selectively binds to an antigen, which optionally includes the target analyte. "Antigen" refers to a chemical species or target analyte which binds to an antibody. The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof. The antibodies can be tested for their desired activity using the in vitro assays described herein, or by analogous methods, after which their in vivo therapeutic and/or prophylactic activities are tested according to known clinical testing methods.

In another step, the methods of the present invention include a step (b) of providing to the binding surface a first solution comprising the target analyte molecules, wherein at least a portion of the target analyte molecules selectively bind to the binding molecules of the binding surface to provide a binding surface having bound target analyte molecules.

In another step, the methods of the present invention include a step (c) of applying an electrical potential between the first and second electrodes during at least a portion of the binding step, thereby enhancing the rate of binding of the target analyte molecules to the binding molecules.

In general, the binding capacity of microplate wells is typically higher than the amount of protein coated in channel. The remaining binding sites that remain after step (b) and (c) are optionally blocked to prevent antibodies or other proteins from nonspecifically binding or adsorbing to the plate during subsequent steps. Appropriate blocking reagents are known in the art and appropriate reagents, concentrations, additional excipients and the like may be determined by one of skill in the art. An appropriate reagent, such as a blocking buffer can include solution of irrelevant protein, mixture of proteins, or other compound that passively adsorbs to all remaining binding surfaces of the plate. The blocking buffer is effective if it improves the sensitivity of an assay by reducing background signal and improving the signal-to-noise ratio. The ideal blocking buffer will bind to all potential sites of nonspecific interaction, eliminating background altogether, without altering or obscuring the epitope for antibody binding. Different blockers can be tested for the highest signal: noise ratio in the assay. Many factors can influence nonspecific binding, including various protein: protein interactions unique to the samples and antibodies involved. The most important parameter when selecting a blocker is the signal: noise ratio, which is measured as the signal obtained with a sample containing the target analyte as compared to that obtained with a sample without the target analyte. Using inadequate amounts of blocker will result in excessive background and a reduced signal: noise ratio. Using excessive concentrations of blocker may mask antibody-antigen interactions or inhibit the enzyme, again causing a reduction of the signal: noise ratio. Typical blockers can include BSA, fetal calf serum, nonfat milk and/or peptide solutions such as 1% BSA and 0.1 M lysine in a buffer, such as a carbonate buffer at an appropriate pH.

In addition to blocking, it is preferred to perform washes between each step of the methods, as known in the art. Washing steps can remove nonbound reagents and decrease background, thereby increasing the signal: noise ratio. Washing can be performed in a physiologic buffer such as Tris-buffered saline (TBS) or phosphate-buffered saline (PBS) without any additives. In some embodiments, a detergent such as 0.05% Tween-20 is added to the buffer to help remove nonspecifically bound material.

The method further includes a step (d) of providing to the binding surface having the bound target analyte molecules a second solution comprising a second binding molecule, wherein at least a portion of the second binding molecules further bind directly or indirectly to the target analyte molecules bound to the binding surface. The binding molecules may be optionally conjugated to a reporter molecule (also called herein a catalyst molecule). In embodiments, the second binding molecule-reporter molecule is an "enzyme-antibody conjugate" which refers to a molecule or chemical species comprising both an enzyme and an antibody, where both components retain at least a portion of their individual properties. In embodiments, for example, an enzyme-antibody conjugate binds to a specific antigen while also catalyzing a chemical reaction.

"Catalyst" or "reporter molecule" refers to a moiety which increases the rate of a chemical reaction. In some embodiments, a catalyst increases the rate of a single specific chemical reaction; in other embodiments, a catalyst increases the rate of multiple chemical reactions, for example a class of chemical reactions. "Enzyme" as used herein is intended to be consistent with use of the term in the fields of molecular biology and biochemistry. In general, an enzyme is a protein which increases the rate of a chemical reaction. In general, an enzyme is a catalyst. In some embodiments, a catalyst is an enzyme. "Catalytically active group" refers to a moiety which comprises a catalyst and can optionally comprise other components which do not impart catalytic activity.

A "catalytic chemical reaction" refers to a chemical reaction which takes place in the presence of a catalyst, thereby increasing the rate of reaction relative to that in which a catalyst is absent. "Bond cleavage reaction" and "bond breaking reaction" refer to a chemical reaction in which a bond between two atoms in a molecule is eliminated, for example resulting in a different chemical species where the two atoms have reduced interaction with or increased average distance from one another. A "bond forming reaction" refers to a chemical reaction in which a bond is added between two atoms, for example resulting in a different chemical species where the two atoms have increased interaction with or reduced average distance from one another. An "oxidation reaction" refers to a reaction in which the oxidation state of a specific molecular or atomic species is increased, for example by loss of electrons from the specific molecular or atomic species. A "reduction reaction" refers to a reaction in which the oxidation state of a specific molecular or atomic species is decreased, for example by addition of electrons to the specific molecular or atomic species.

Reporter molecules, also called antibody labels or antibody tags, typically include enzymes such as horseradish peroxidase (HRP), alkaline phosphatase (ALP), glucose oxidase (GO) and beta galactosidase (BGAL or βgal); in addition to biotin, digoxigenin and assorted haptens. secondary antibodies conjugated to AP or HRP. In these methods, when the enzyme substrate is added, either a colored precipitate is deposited on the blot (colorimetric detection) or a chemiluminescent or fluorescent product is formed and the light signal is captured on film or with a digital imaging system.

Useful catalyst molecules include enzyme-antibody, enzyme-antigen, enzyme-biotin, enzyme-streptavidin, enzyme-avidin, enzyme-protein, enzyme-nucleic acid, enzyme-protein nucleic acid, enzyme-pharmaceutical, enzyme-hormone, enzyme-illicit drug, enzyme-lipid, or enzyme-metabolite conjugates; or any combination of these. In specific embodiments, the catalyst molecules comprise a catalytically active group and antigens of antibodies, antibodies, biotin, streptavidin, aptamers, nucleic acids, peptide nucleic acids or any combination of these. Specifically useful catalyst molecules include those comprising alkaline phosphatase, acid phosphatase, horseradish peroxidase, beta-galactosidase, glucose oxidase, carboxypeptidase B, porcine liver esterase, rabbit esterase, lipase, butyryl cholinesterase, arginase, a catalyst for a bond cleavage reaction, a catalyst for a bond forming reaction, a catalyst for an oxidation reaction, a catalyst for a reduction reaction or any combination or derivative of these. In specific embodiments, the reaction of the substrate molecules at the catalyst is a bond forming reaction, a bond breaking reaction, an oxidation reaction or a reduction reaction.

In some embodiments, unbound signal-generating conjugates may need to be washed from a reaction site to prevent unbound conjugates from activating the substrate and producing and inaccurate signal. It may be difficult to remove conjugates sticking to the edges of the reaction sites in such a fluidic device if, for example, there is not an excess of a wash solution. To decrease the signal contributed from unbound conjugates stuck to the edge of a reaction site, it may be advantageous to expand the reaction site edge or wall radius in order to distance non-specifically bound conjugate from the desired actual detection area, represented by bound reactant.

When using a wash buffer in an assay, the device can store buffer in vials in fluid communication with the reaction site. In an embodiment, the wash reagent is able to remove reagent from the reaction sites by about 99.9% by washing. In general, a high washing efficiency resulting in a high degree of reduction of undesired background signals is preferred. Washing efficiency is typically defined by the ratio of signal from a given assay to the total amount of signal generated by an assay with no wash step and can be readily determined by routine experimentation. It is generally preferred to increase the volume of washing solution and time of incubation but without sacrificing the signals from a given assay. In some embodiments, washing is performed with about 200 ul to about 5000 ul of washing buffer, preferably between about 250 ul to about 1000 ul washing buffer, for about 10 to about 300 seconds. To facilitate this efficiency, the sides of the reaction sites are adapted for smooth flow of the reagents and for minimal boundary layer effects.

Additionally, it can be advantageous to use several cycles of small volumes of wash solution which are separated by periods of time where no wash solution is used. This sequence allows for diffusive washing, where labeled antibodies diffuse over time into the bulk wash solution from protected parts of the assay such as the well edges or surfaces where it is loosely bound and can then be removed when the wash solution is moved from the reaction site.

Where desired, the subject systems and fluidic devices can be configured to contain any reagents necessary to perform an assay on a fluidic device according to the present invention on-board, or housed within the fluidic device before, during, and after the assay. In this way the only inlet or outlet from the fluidic device is preferably the bodily fluid sample initially provided by the fluidic device. This design also helps create an easily disposable fluidic device where all fluids or liquids remain in the device. The on-board design also prevents leakage from the fluidic device into the reader assembly which should remain free from contamination from the fluidic device.

In embodiments of the invention the fluidic device includes at least one waste chamber to trap or capture all liquids after they have been used in the assay. In an embodiment, there is more than one waste chamber, at least one of which is to be used with a calibration assembly described herein below. On-board waste chambers also allow the device to be easily disposable. The waste chamber is preferably in fluidic communication with at least one reaction site.

In certain embodiments, the step of detecting an amount of concentrated reaction product molecules comprises exposing the reaction product molecules to electromagnetic radiation and detecting the scattering, absorption or emission of radiation. Typical techniques for this type of detection include, but are not limited to ultraviolet-visible spectrometry, fluorescence spectrometry, Raman spectrometry (SERS), infrared spectrometry or detection of radioactive decay from radiolabeled materials. In embodiments, the step of detecting an amount of concentrated reaction product molecules comprises exposing the reaction product molecules to a reagent that induces chemiluminescence and detecting emitted electromagnetic radiation. In embodiments, the step of detecting an amount of concentrated reaction product molecules comprises measuring a voltage or current required to change the oxidation state (e.g., oxidize or reduce) of the reaction product molecules. Typical techniques for this type of detection include, but are not limited to amperometry and voltametry. In some embodiments where the amount of concentrated reaction product molecules is detected in front of a semi-permeable membrane, the detection device is optionally positioned at the anticipated signal maximum, such as to observe reaction product molecules positioned from between 0 and 1 mm of the surface of the semi-permeable membrane, for example positioned between 50 μm and 500 μm or between 100 μm and 300 μm of the surface of the semi-permeable membrane.

In specific embodiments, the amount of concentrated reaction product molecules is determined as a function of time or at or after one or more time intervals. In an exemplary embodiment, a method of this aspect further comprises the step of determining an amount of the catalyst molecules bound to the binding surface from the detected amount of the concentrated reaction product molecules after one or more time intervals. Optionally, an embodiment further comprises the step of determining an amount of the target analyte in the first solution from the determined amount of the catalyst molecules bound to the binding surface after one or more time intervals. An exemplary embodiment further comprises the step of measuring the rate at which the reaction product molecules are concentrated in the microfluidic trapping region. Optionally, the concentrating step comprises allowing time to pass, whereby unreacted substrate molecules continue to catalytically react with the catalyst molecules bound directly or indirectly to target analyte molecules bound to the binding surface to directly or indirectly produce reaction product molecules which concentrate in the microfluidic trapping region.

In one specific embodiment, the binding surface comprises a surface bound antibody, the target analyte molecules comprise an antigen for the surface bound antibody and the catalyst molecules comprise an enzyme-antibody conjugate. In various embodiments, the reporter molecules are covalently or non-covalently bound to the target analyte molecules bound to the binding surface. For example, in certain embodiments, the reporter molecules covalently or non-covalently binds to binding molecules, and the binding molecules covalently or non-covalently bind to the target analyte molecules bound to the binding surface, thereby binding the catalyst molecules covalently or non-covalently to the target analyte molecules bound to the binding surface.

In exemplary embodiments, the reaction product molecules comprise a detectable moiety, such as a chromophore or a moiety capable of undergoing a chemiluminescent reaction or a moiety capable of being reversibly oxidized/reduced between two oxidation states or any combination of these. Optionally, the substrate molecules comprise a chromophore and the reaction product molecules comprise the same chromophore or a substantially unaltered variant of the same chromophore. Useful chromophores include, but are not limited to an azo dye, a xanthene dye, an anthraquinone dye, an acridine dye, an oxazine dye, a thiazene dye, a triarylmethane dye, a diarylmethane dye, a quinoline styryl dye, a phthalocyanine dye, a squarene dye, a polyalkene dye and any combination of these.

In a specific embodiment, the substrate molecules exhibit a first absorption spectrum and the reaction product molecules exhibit a second absorption spectrum at least partially overlapping the first absorption spectrum. In a specific embodiment, the substrate molecules exhibit a first emission spectrum and the reaction product molecules exhibit a second emission spectrum at least partially overlapping the first emission spectrum. In a specific embodiment, the substrate molecules exhibit a first fluorescence spectrum and the reaction product molecules exhibit a second fluorescence spectrum at least partially overlapping the first fluorescence spectrum. Optionally, the first and second absorption spectra are substantially identical; the first and second emission spectra are substantially identical; the first and second fluorescence spectra are substantially identical; or any combination of these.

For certain embodiments, the substrate molecules exhibit a first absorption spectrum and the reaction product molecules exhibit a second absorption spectrum non-overlapping the first absorption spectrum. For certain embodiments, the substrate molecules exhibit a first emission spectrum and the reaction product molecules exhibit a second emission spectrum non-overlapping the first emission spectrum. For certain embodiments, the substrate molecules exhibit a first fluorescence spectrum and the reaction product molecules exhibit a second fluorescence spectrum non-overlapping the first fluorescence spectrum.

Substrate molecules useful with the methods of this aspect include substrate molecules which are directly or indirectly converted into colored, fluorescent, and/or ionic product molecules upon and/or after reaction at the catalyst. For various embodiments, the substrate molecules are non-ionic; for other embodiments, the substrate molecules are ionic. In an exemplary embodiment, the substrate molecules and the reaction product molecules are ions having charges of opposite sign.

The most common substrates for colorimetric HRP are 4-Chloro-1-naphthol (4CN) and 3,3'-diaminobenzidine (DAB). Some limitations of HRP colorimetric detection systems are decreased sensitivity when compared to AP colorimetric detection systems, fading of blots upon exposure to light, inhibition of HRP activity by azide, and nonspecific color precipitation. Colorimetric AP systems use soluble 5-bromo-4-chloro-3-indolyl phosphate (BCIP) and nitroblue tetrazolium (NBT) as substrates to produce a stable reaction product that will not fade (see Figure below). AP can easily be inactivated by exposure to acidic solutions.

Reagents useful for methods of these aspects include reagents which react with the reaction product molecules to establish an ionic charge of the reaction product molecules or to provide the reaction product molecules with an ionic charge different from that of the substrate molecules. Exemplary reagents include, but are not limited to acids, bases, oxidizing agents and reducing agents. For example, useful reagents include a proton, a carboxylic acid, a phosphoric acid or mono- or di-ester of a phosphoric acid, bisulfate, a sulfonic acid, an ammonium or substituted ammonium, phenol or substituted phenol, hydroxide, a carboxylate anion, phosphate or mono- or di-ester of a phosphate, an amine or substituted amine, a borate or borate ester anion- persulfate, hypochlorite, hydroperoxide and any combination of these.

In certain embodiments, the reaction product molecules undergo a second or subsequent reaction to establish an ionic charge. In general, the reaction product molecules can undergo a second or subsequent reaction covalently bonding the direct reaction product of the catalytic reaction to one or more ionic atoms or molecules to establish the ionic charge of the reaction product molecules which are subsequently detected. Specific examples include protonation or deprotonation reactions.

In a specific embodiment, a substrate molecule undergoes a bond breaking reaction at a catalyst. In a specific embodiment, a substrate molecule undergoes a bond forming reaction at a catalyst. Specifically useful substrate molecules include, but are not limited to Amplex Red®, o-nitrophenyl galactopyranoside (galactose-ONP), fluorescein phosphate,

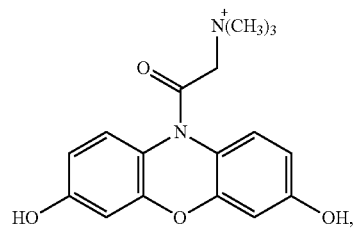

-continued
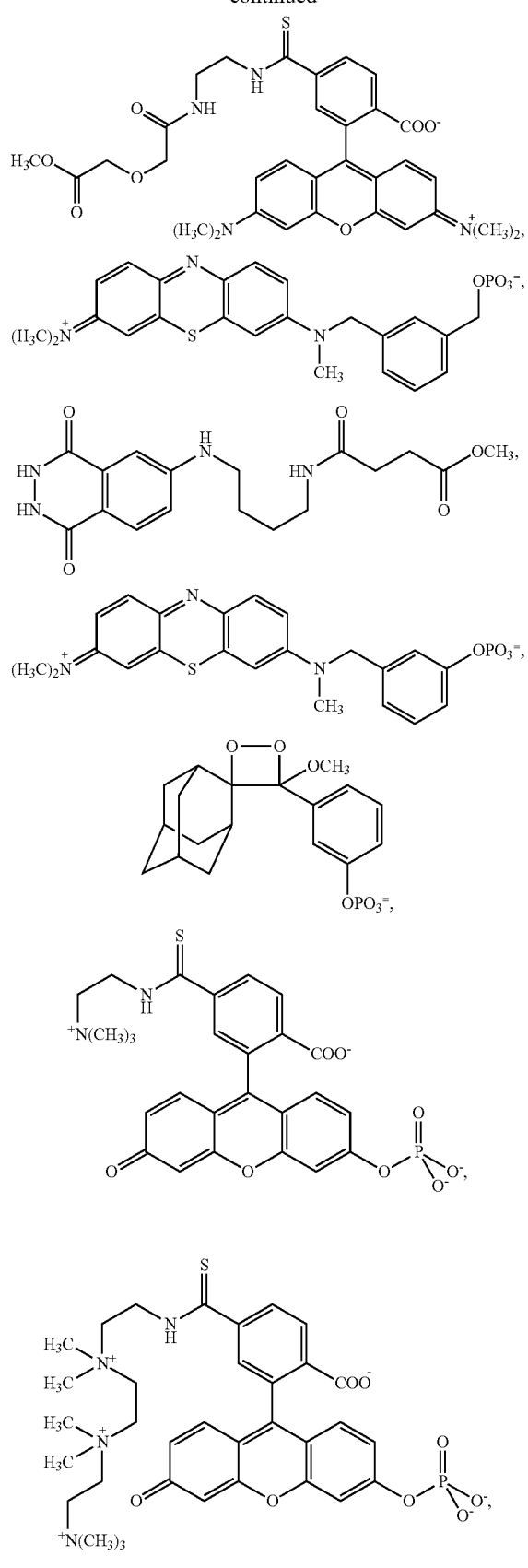
any variant of these or any combination of these.
In specific embodiments, the reaction product molecules are resorufin anion, o-nitrophenolate, fluorescine anion, substituted coumarin anion,
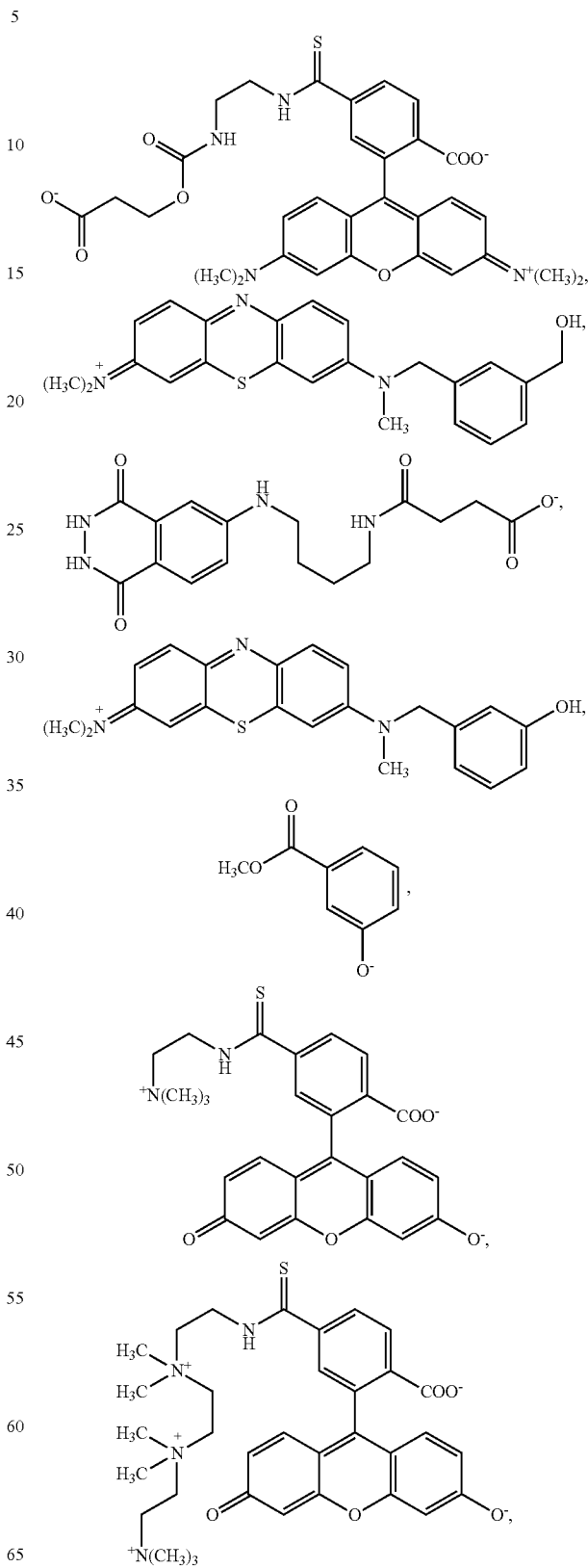

any variant of these or any combination of these. In embodiments, useful reaction product molecules include those which are detectable or include a detectable component, for example by optical detection or electrochemical detection.

In embodiments, the step of transporting comprises separating at least a portion of the reaction product molecules from unreacted substrate molecules. Electrical potentials useful with the methods described herein include, but are not limited to DC potentials, such as DC potentials selected over the range of 1 V to 5000 V, for example in the range of 50 V to 2000 V or in the range of 100 V to 1000 V. Optionally, the microfluidic device comprises three or more electrodes positioned in the microfluidic device, for example in fluid and/or electrostatic communication with one another.

Chemiluminescence occurs when a chemical substrate is catalyzed by an enzyme, such as AP or HRP, and produces light as a by-product. The light signal can be captured on X-ray film or by a charge-coupled device (CCD) imager.

The term "substrate" as used herein is intended to be consistent with the use of the term in relation to enzyme catalyzed reactions. A substrate is a molecule which undergoes a chemical reaction in the presence of a catalyst to form a detectable product. "Chromophore" refers to a portion of a molecule which absorbs light or is otherwise responsible for the color of the molecule. "Chemiluminescent" refers to a chemical species which emits light as a product of a chemical reaction.

"Reagent" refers to an atomic or molecular species which takes part in a chemical reaction.

"Directly producing" refers to forming a specific product molecule by means of a single chemical reaction. "Indirectly producing" refers to forming a specific product molecule by means of additional chemical reactions. In certain embodiments, an ionic species is directly produced from a catalytic chemical reaction. In certain embodiments, an ionic species is indirectly produced from a catalytic chemical reaction followed by another chemical reaction, such as a protonation or deprotonation reaction. In yet further embodiments, an ionic species may be indirectly produced from a catalytic chemical reaction followed by another chemical reaction such as oxidation, reduction, or covalent bond formation with a moiety possessing ionic charge (e.g., chemical derivatization).

The term "establishing an ionic charge" refers to a process in which an atomic or molecular species is provided with an ionic charge. In embodiments, a chemical reaction can establish an ionic charge of a reaction product.

"Reaction product" refers to an atomic or molecular species which is the result of a chemical reaction or a series of chemical reactions. In a specific embodiment, a "detectable reaction product" is a reaction product which has components which allow for the observation of the presence and/or number of reaction products. In embodiments, a detectable reaction product is observable by absorption of light, emission of light (e.g., fluorescence spectroscopy or chemiluminescence detection), electrochemical detection, and/or detection by surface enhanced Raman spectroscopy.

In one embodiment, the reporter or catalyst molecule is useful for electrochemiluminescence (ECL) detection. ECL-based assays, in embodiments, comprise, for example, ruthenium labels, such as tris(bipyridine) ruthenium (II) chloride ($Ru(bpy)_3$), which emit light when electrochemically reduced wherein tripropylamine is oxidized at the surface of electrodes, which in turn reduces the ruthenium, which then emits light which can be detected. The reaction is controlled and localized by the electrode. ECL detection methods are generally known in the art, as seen in U.S. Pat. No. 5,945,344, "Electrochemiluminescence Method," which is incorporated herein by reference for all that is taught and disclosed.

The methods of the invention also include the step (e) of detecting a signal indicating an amount of the originally present target analyte molecules in the sample.

"Detection sensitivity" refers to the minimum signal that a detector or device is capable of distinguishing from noise. In embodiments, the detection sensitivity for a target analyte is the minimum concentration of target analyte in a solution which a system or device is capable of determining the presence of.

"Detector" refers to a device capable of registering a signal, such as absorbance, fluorescence, or luminescence. Absorbance detection is commonly used in ELISA assays, in quantifying protein or nucleic acid concentrations, or in measuring enzymatic activity. A detector includes a microplate reader well known in the art of ELISA.

Figure 4A:
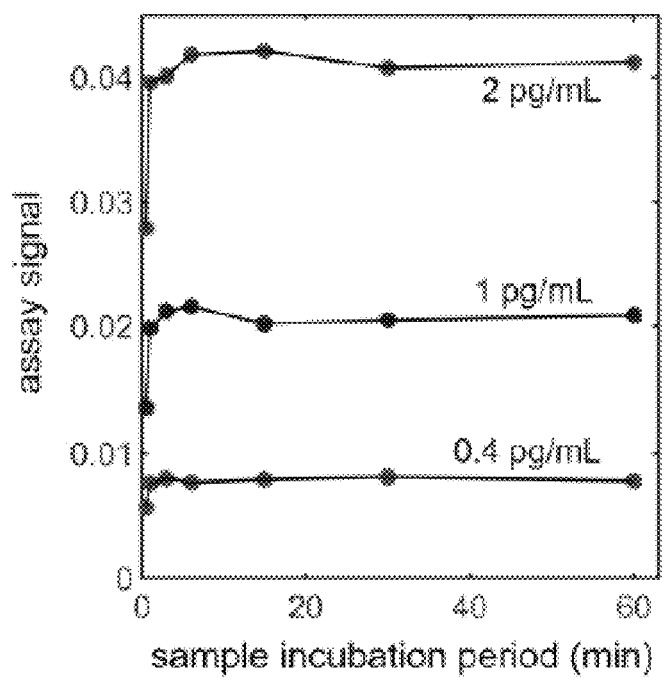
FIG. 4A provides a graphical representation of variation in assay signal with sample incubation time upon application of steady +1V voltage drop across the gold electrodes for 0.4 pg/ml, 1 pg/ml, and 2 pg/ml.

The methods disclosed herein include the step of applying an electrical potential between the first and second electrodes during at least a portion of the binding step, thereby enhancing the rate of binding of the target analyte molecules to the binding molecules. In typical ELISA assays, the step of binding the target analyte molecules to the binding molecules is a step which, in many protocols, requires incubation of the sample with the binding molecules for a period of time, for example, one hour at room temperature. Even in microfluidics assays, target analyte molecules are provided for periods of time such as twenty minutes. The long incubation times are attributed to inefficient mass transport for the analyte molecules to move from a solution to the surface. In the present invention, due to the efficiency of the electric field for transporting the target analyte to the binding molecules, the binding reaction goes to completion quickly. For example, in the present invention the binding reaction is maximized or substantially completed at about 10 seconds, 20 seconds, 30 seconds, 40 seconds, 50 seconds, 1 minute, about 2 minutes, about 3 minutes, about 4 minutes, about 5 minutes, about 6 minutes, about 8 minutes, or about 10 minutes. Maximized or substantially complete is understood as the maximal amount of binding that can occur in the system, see, e.g., FIG. 4A. Therefore, in embodiments, the incubation can be performed for about 10 seconds, 20 seconds, 30 seconds, 40 seconds, 50 seconds, 1 minute, about 2 minutes, about 3 minutes, about 4 minutes, about 5 minutes, about 6 minutes, about 8 minutes, or about 10 minutes. In embodiments, the incubation/binding step can be performed for about 1 minute and the binding reaction is maximized or substantially complete after the incubation step.

In one embodiment, the sensitivity of the assay may be increased by performing the binding step with multiple aliquots of the sample containing the target analyte. Therefore, in one embodiment the steps (b) and (c) can be performed at least two times with additional aliquots of sample comprising the target analyte solution prior to performing step (d) of the method. In embodiments the steps (b) and (c) are performed with additional aliquots comprising the target analyte solution at least three times, at least four times, at least five times, at least seven times, at least ten times, at least fifteen times, at least twenty times, at least twenty five times, at least thirty times, at least forty times, at least fifty times, at least sixty times or more. In embodiments, each incubation/binding step is performed for about 1 minute and the binding reaction is maximized or substantially complete after the incubation step.

In embodiments, wherein at least two times more target analyte molecule is bound to the binding surface compared with binding the target analyte molecule in the absence of an applied electric field between the first and second electrodes, as measured by an assay signal. In other embodiments, at least three times more, at least five times more, at least ten times more, at least twenty times more, at least thirty times more, at least forty times more, at least fifty times more, at least sixty times more, at least seventy times more, at least eighty times more, at least ninety times more, at least one hundred times more, at least two hundred, three hundred, five hundred times or more target analyte is bound to the binding surface after performing the method steps of the invention as described hereinabove.

In embodiments, the amount of time required to bind a specified amount of target analyte molecule applied to the binding surface is reduced by at least or approximately ten fold, at least or approximately twenty fold, at least or approximately fifty fold, at least or approximately one hundred fold, or at least or approximately five hundred fold, compared with binding the target analyte molecule in the absence of an applied electric field between the first and second electrodes.

In an exemplary assay, the sample containing analyte first flows over a reaction site containing antibodies and treated by methods of the invention, e.g., electric field assisted rapid capture of antigens (analyte). The antibodies bind the analyte present in the sample. After the sample passes over the surface, a solution with a second binding molecule with a reporter molecule conjugated thereto is passed over the surface. The amount of reporter bound to the surface is then measured by the appropriate technique, and the detected reporter is proportional to the amount of analyte present in the sample.

A representative procedure for the methods of the invention can be seen as follows. Modifications to the procedure in accordance with whether the ELISA is a direct or indirect ELISA can be made by those of skill in the art. The entire assay can be performed in room temperature. An absorbent pad or holder may be used for waste materials. A device of the invention comprising glass channels comprising first and second electrodes to create a lateral electric field as described herein may be pretreated to optimize binding of the binding molecule, by a number of techniques known in the art as described herein. For example, the glass channels comprising electrodes may be cleaned after fabrication by successive treatments with sodium hydroxide, de-ionized water and methanol, as known in the art. The electrodes may be pretreated with a reagent such as thiourea to assist adsorption of proteins onto the electrode layer. The glass may be treated with a functionalized alkoxysilane, such as 3-aminopropyltriethoxysilane, to facilitate the binding of the binding molecules and a bi-functional linker, such as glutaraldehyde, to immobilize the binding proteins on to the surface of the channels, using conditions known in the art.

Next, the binding molecule, in an embodiment, a polyclonal or monoclonal capture antibody, is introduced to the binding surface under conditions known in the art, such as incubation for one hour at 0.1-100 ug/mL. After that incubation, the unreacted surfaces on the channel surface can be "capped off" or reacted by methods known in the art, such as for example treating with a 1% BSA solution and/or 0.1 M lysine solution. This step minimizes non-specific binding of undesired proteins.

The sample or samples comprising the target analyte may be introduced to the channel binding surfaces using methods known in the art. As discussed herein, during the incubation, which can be for times as given, such as for one minute, an electrical voltage difference of 1V was applied during the sample incubation step. After the incubation, an additional sample of target analyte can be introduced and the sample incubation step repeated, for as many times as appropriate or desired.

An appropriate second binding molecule conjugated with a reporter molecule, or combination of the same, such as a detection antibody as known in the art conjugated to biotin followed by a streptavidin-horseradish peroxidase enzyme may be added to the binding surface by methods known in the art, followed by measuring the signal generated upon introduction of a substrate (here, Amplex red and hydrogen peroxide), with measurement of fluorescence signal as known in the art.

In another embodiment of the present invention, methods provided for detecting a target analyte further include the steps of: providing a microfluidic device comprising a binding surface in a microfluidic channel in fluid communication with a microfluidic trapping region and at least two electrodes; providing to the binding surface a first solution comprising target analyte molecules, wherein at least a portion of the target analyte molecules selectively bind to the binding surface; providing to the binding surface having bound target analyte molecules a second solution comprising reporter molecules, wherein at least a portion of the reporter molecules further bind directly or indirectly to target analyte molecules bound to the binding surface; providing to the binding surface having bound target analyte molecules and reporter molecules a third solution comprising substrate molecules, wherein at least a portion of the substrate molecules undergo a catalytic chemical reaction with reporter molecules bound directly or indirectly to target analyte molecules bound to the binding surface, thereby directly or indirectly producing reaction product molecules having an ionic charge different from an ionic charge of the substrate molecules; transporting at least a portion of the reaction product molecules into the microfluidic trapping region by applying an electrical potential between the at least two electrodes, wherein at least one electrode is positioned in the microfluidic trapping region and wherein the electrical potential provides a force attracting the reaction product molecules toward the microfluidic trapping region; concentrating reaction product molecules in the microfluidic trapping region; and detecting an amount of concentrated reaction product molecules in the microfluidic trapping region, for example at one or more time intervals. This embodiment is described in more detail in U.S. Pat. No. 8,507,208 which is incorporated by reference herein for all that is taught and disclosed.

A specific method of this aspect comprises the steps of providing a microfluidic device comprising a binding surface in fluid communication with a microfluidic trapping region and at least two electrodes, wherein the microfluidic trapping region includes a semi-permeable membrane; providing to the binding surface a first solution comprising target analyte molecules, wherein at least a portion of the target analyte molecules selectively bind to the binding surface, thereby creating an analyte activated binding surface; providing to the analyte activated binding surface a second solution comprising reporter molecules, wherein at least a portion of the reporter molecules further binds directly or indirectly to the analyte activated binding surface, thereby creating a catalytic binding surface; providing to the catalytic binding surface a third solution comprising substrate molecules, the substrate molecules comprising a chromophore, wherein at least a portion of the substrate molecules undergo a catalytic chemical reaction at the catalytic binding surface, thereby producing reaction product molecules, the reaction product molecules comprising the chromophore in the same or a substantially unaltered form as in the substrate molecules and wherein an ionic charge of the reaction product molecules is different from an ionic charge of the substrate molecules; transporting at least a portion of the reaction product molecules into the trapping region by applying an electrical potential between the at least two electrodes, wherein at least one electrode is positioned in the microfluidic trapping region and wherein the electrical potential provides a force attracting the reaction product molecules toward the microfluidic trapping region; concentrating reaction product molecules in the microfluidic trapping region in front of, at a surface of and/or within the semi-permeable membrane; and detecting an amount of concentrated reaction product molecules in front of, at a surface of and/or within the semi-permeable membrane. In a specific embodiment, the step of detecting an amount of concentrated reaction product molecules in front of, at a surface of and/or within the semi-permeable membrane comprises detecting an amount of concentrated reaction product molecules as a function of time or after one or more time intervals.

"Semi-permeable membrane" refers to a membrane which selectively permits specific chemical species to pass through while preventing or reducing the rate at which other chemical species pass through. In some embodiments, a semi-permeable membrane is size selective; that is, it permits chemical species having a size below a threshold size to pass through while preventing chemical species having a size above the threshold from passing through. In some embodiments, a semi-permeable membrane is molecular weight dependent; that is, it permits chemical species having a molecular weight below a threshold to pass through while preventing chemical species having a molecular weight above the threshold from passing through. In some embodiments, a semi-permeable membrane is chemically selective; that is, it permits only certain chemical species to pass through while preventing other chemical species from passing through or it prevents only certain chemical species from passing through while permitting other chemical species to pass through. In a specific embodiment, an electrically conductive semi-permeable membrane refers to a membrane which allows for electrical communication between electrodes positioned on opposite sides of the semi-permeable membrane, for example by passage of ions through the membrane. In certain embodiments, an electrically conductive semi-permeable membrane is itself composed of insulating (i.e., non-conducting) material, but has a structure allowing for the passage of ions and electrical communication through the membrane, for example by providing pores or passages capable of transmission of ions or solutions containing ions. In general, for most embodiments, semi-permeable membranes will always allow the passage of the small, charged molecules comprising a buffer (e.g., a molecular weight cutoff of >100 Daltons).

Systems and methods are described herein for detecting the catalytic reaction of an enzyme with a substrate, for example by directly detecting the catalytic reaction product. The detected reaction product can be used to infer the presence of the catalyst and if time dependent amounts of the reaction product are available, the amount of catalyst present in a system can also be inferred. Additionally, in systems where the catalyst binds to target analyte molecules, the presence and amount of target analyte in a system can also be inferred from the corresponding observation and amounts of catalyst.

Also provided herein are microfluidic devices useful for sensitive detection of analytes. The devices described herein are also useful for detecting direct or indirect binding of enzymes or catalysts to a surface, for example a surface having analytes bound thereon.

Microfluidic ELISA assay formats are well known in the art and certain common features are not shown herein. A schematic of a close up of the channel walls of a representative microfluidics device are shown in FIG. 1A. Microfluidics channel wall(s) 10 have a high voltage end, electrode 12 and a low voltage end, electrode 14, from which a lateral electric field 50 may be generated. Binding molecules (here, antibodies) 20 are shown immobilized onto the channel walls with target analyte molecules 30 shown in the process of binding to the binding molecules 20.

Figure 1B:
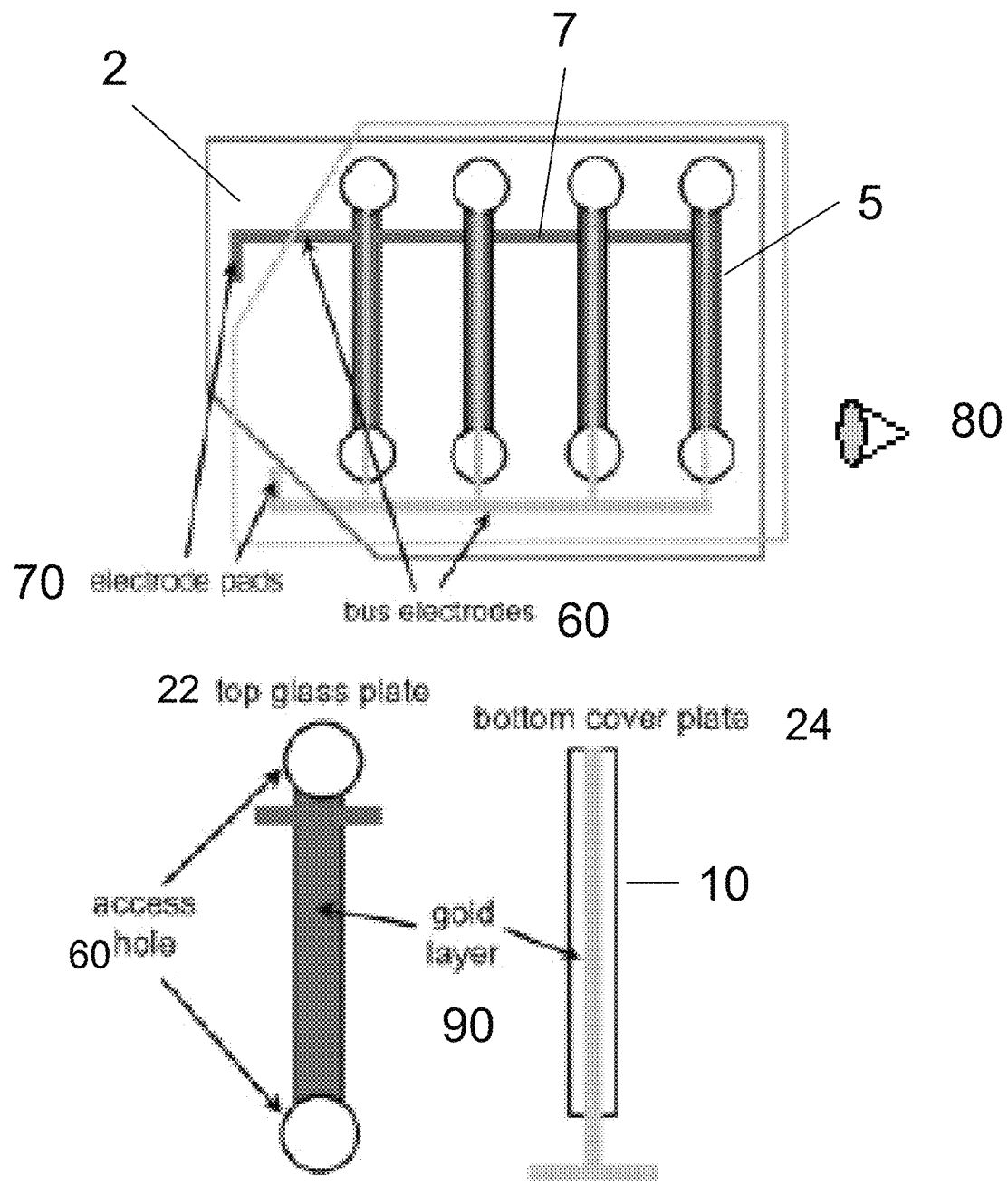
FIG. 1B provides a schematic of the microfluidic device used for enabling the EFARAC process. While only 4 assay channels are shown in the schematic drawing, the actual device had 8 assay channels. The electrodes on the top and bottom channel walls have been depicted with different colors in the drawing for making them distinguishable in the drawing, they were both fabricated with chromium and gold layers following an identical process.
Figure 1C:
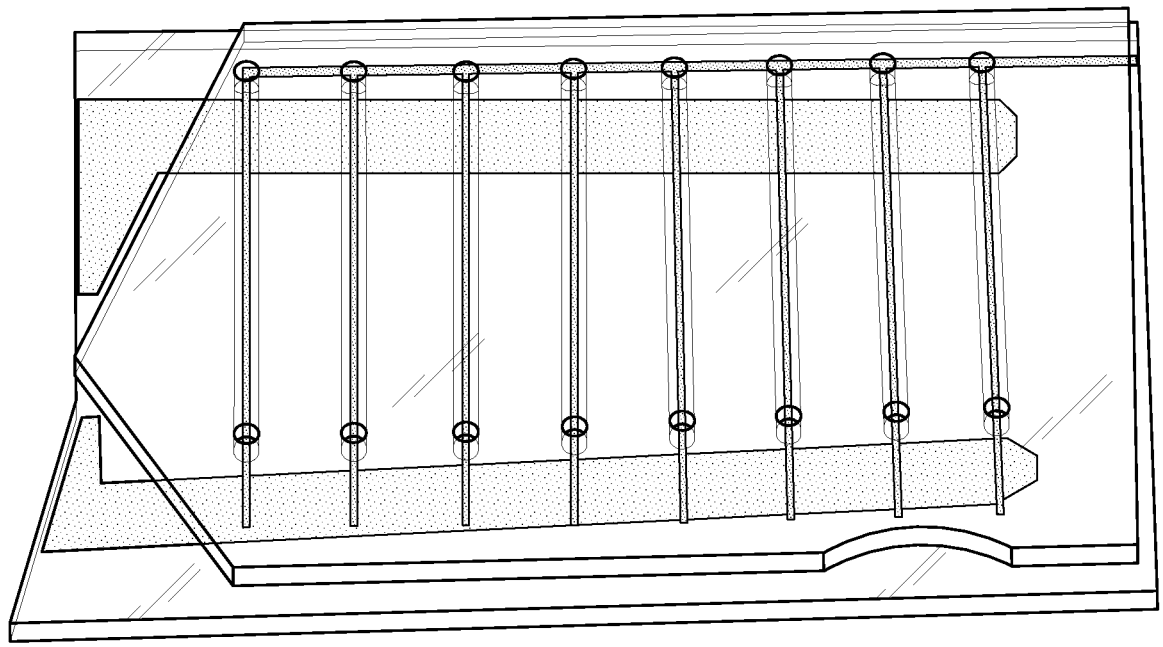
FIG. 1C provides a photograph of an actual device in accordance with the schematics provided in FIG. 1B.

A schematic of a representative microfluidics device is shown in FIG. 1B. Base 2 (any appropriate material) is capable of holding microfluidics channel(s) 5. Microfluidics channel(s) 5 comprise a top glass plate 22 and a bottom glass plate 24. There can be one more microfluidics channel(s) 5, commonly, 4 channels, 8 channels or an amount of channels adapted to be used together with conventional ELISA detection systems such as microwell plate readers. Microfluidics channel(s) 5 comprise channel wall(s) 10 comprising top glass plate 22 and a bottom glass plate 24 have deposited electrodes 90 where multiple microfluidics channels 2 are connected through bus electrodes 60 and 7 and electrode pads 70 to a voltage source (not shown). Access hole(s) 60 at either or both ends of microfluidics channel(s) 5 allow for entry of sample into the device at one end and removal of wastes at the other. Detection device 80 is positioned to read signal output from microfluidics channel(s) 5.

It is noted that a "mirror effect" in which analytes that are localized between gold (or silver) surfaces are subject to a signal enhancement due to reflection of signal output such as fluorescence or electrochemiluminescence. This further enhancement of signal (and decrease in detection limit).

In a specific method of this aspect, the microfluidic device further comprises a semi-permeable membrane positioned in a microfluidic trapping region, as disclosed in U.S. Pat. No. 8,507,208. See FIGS. 13 and 14. An embodiment of this aspect comprises the steps of providing a microfluidic device comprising a binding surface in fluid communication with a microfluidic trapping region and at least two electrodes, wherein the microfluidic trapping region comprises a semi-permeable membrane; providing to the binding surface a first solution comprising target analyte molecules, wherein at least a portion of the target analyte molecules selectively bind to the binding surface; providing to the binding surface having bound target analyte molecules a second solution comprising reporter molecules, wherein at least a portion of the reporter molecules further binds directly or indirectly to target analyte molecules bound to the binding surface; providing to the binding surface having bound target analyte molecules and reporter molecules a third solution comprising substrate molecules, wherein at least a portion of the substrate molecules undergo a catalytic chemical reaction with reporter molecules bound directly or indirectly to target analyte molecules bound to the binding surface, thereby directly or indirectly producing reaction product molecules having an ionic charge different from an ionic charge of the substrate molecules; transporting at least a portion of the reaction product molecules into the microfluidic trapping region by applying an electrical potential between the at least two electrodes, wherein at least one electrode is positioned in the microfluidic trapping region and wherein the electrical potential provides a force attracting the reaction product molecules toward the microfluidic trapping region; concentrating reaction product molecules in the microfluidic trapping region in front of, at a surface of and/or within the semi-permeable membrane; and detecting an amount of concentrated reaction product molecules in front of, at the surface of and/or within the semi-permeable membrane.

In some embodiments, the microfluidic device further comprises a microfluidic channel and a microfluidic side channel in fluid communication with the microfluidic channel; optionally, the binding surface is positioned in the microfluidic channel and the microfluidic trapping region is positioned in the microfluidic side channel. In some embodiments, the microfluidic device further comprises a microfluidic channel and a microfluidic side channel in fluid communication with the microfluidic channel, wherein the binding surface is positioned in the microfluidic channel; optionally, the microfluidic trapping region is positioned in the microfluidic side channel and at least one of the two or more electrodes and the semi-permeable membrane, if present, are positioned in the microfluidic side channel. In certain of these and other embodiments, the microfluidic device further comprises one or more additional microfluidic side channels positioned in fluid communication with the microfluidic channel. Optionally, a method of this aspect further comprises the step of providing one or more additional solutions to at least one of the one or more additional microfluidic side channels, at least one of the solutions comprising a reagent.

In another aspect, provided are microfluidic devices for detecting a target analyte. An embodiment of this aspect comprises a microfluidic channel including a binding surface comprising the target analyte and a catalyst bound directly or indirectly to the target analyte; a solution in the microfluidic device, the solution comprising substrate molecules and ionic reaction product molecules, wherein the ionic reaction product molecules are reaction products of a catalytic bond cleavage reaction or a catalytic bond forming reaction of the substrate molecules at the binding surface or a catalytic reaction in which the substrate is oxidized or a catalytic reaction in which the substrate is reduced; two electrodes in fluid communication with the microfluidic channel; a microfluidic trapping region in fluid communication with the microfluidic channel, wherein one of the two electrodes is positioned in the microfluidic trapping region, and wherein a potential is applied between the two electrodes to attract the ionic reaction product molecules into the microfluidic trapping region; and a detector positioned to detect the ionic reaction product molecules positioned in the microfluidic trapping region.

Another embodiment of this aspect comprises a microfluidic channel including a binding surface region comprising the target analyte and a catalyst bound directly or indirectly to the target analyte; a solution in the microfluidic device, the solution comprising substrate molecules and ionic reaction product molecules, wherein the ionic reaction product molecules are reaction products of a catalytic bond cleavage reaction or a catalytic bond forming reaction of the substrate molecules at the binding surface region or a catalytic reaction in which the substrate is oxidized or a catalytic reaction in which the substrate is reduced; two electrodes in fluid communication with the microfluidic channel; a microfluidic trapping region in fluid communication with the microfluidic channel, wherein one of the two electrodes is positioned in the microfluidic trapping region; and a detector positioned to detect the ionic reaction product molecules; characterized in that a first detection sensitivity for the ionic reaction product molecules in the microfluidic trapping region is less than or equal to a second detection sensitivity for the ionic reaction product molecules in the binding surface region when no potential is applied between the two electrodes; and a third detection sensitivity for the ionic reaction product molecules in the microfluidic trapping region is at least twenty times greater than a fourth detection sensitivity for the ionic reaction product molecules in the binding surface region when a potential is applied between the two electrodes to attract the ionic reaction product molecules into the microfluidic trapping region. Optionally, the third detection sensitivity is greater than the fourth detection sensitivity by a factor selected over the range of 20 to 50,000, such as a factor in the range of 100 to 5000.

Figure 13:
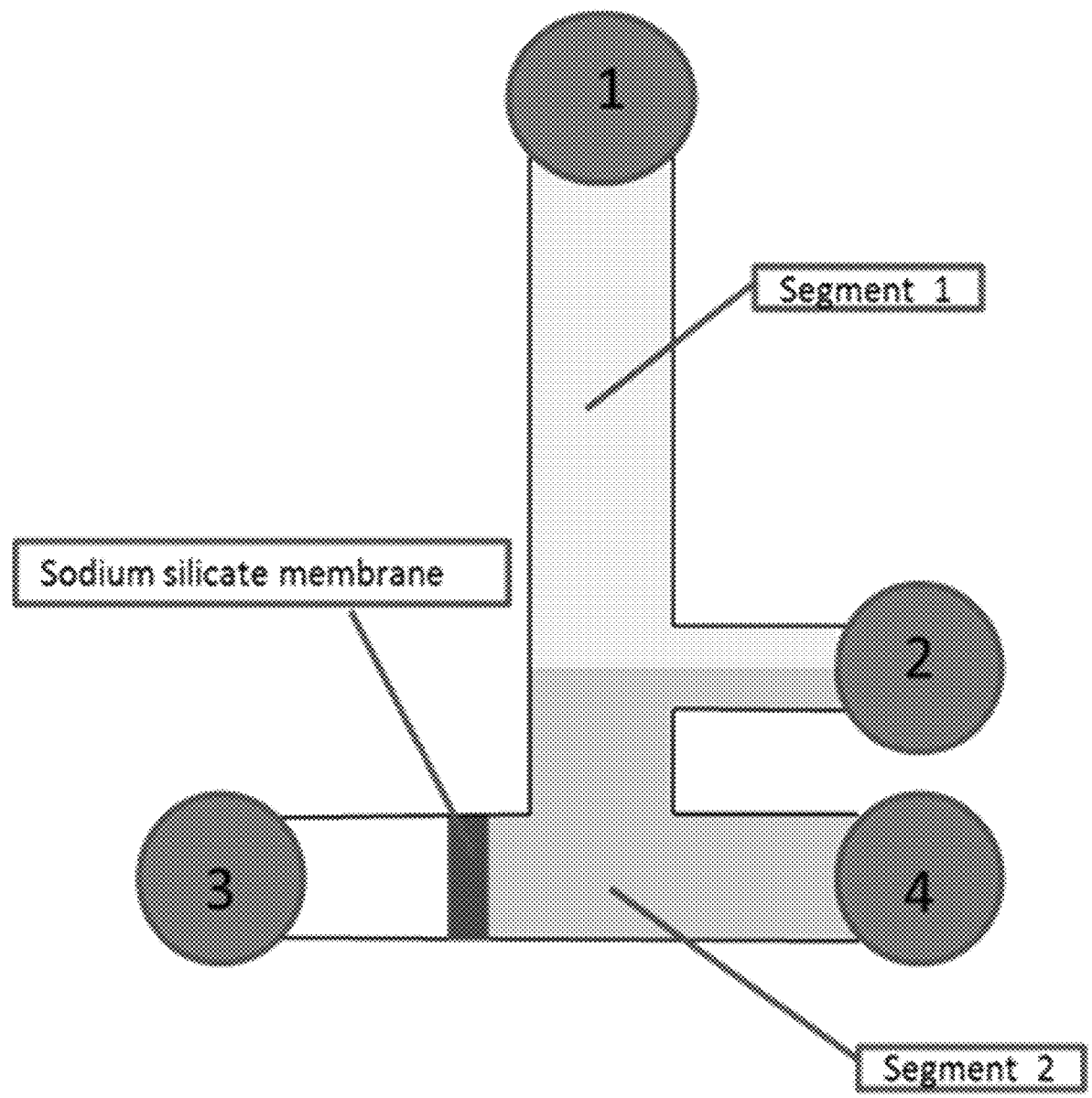
FIG. 13 shows a schematic illustration of an overview of an exemplary microfluidic design further embodiment.

Devices of this aspect as shown in FIG. 13 optionally further comprise a semi-permeable membrane positioned in the microfluidic trapping region to impede transport of the ionic reaction product molecules toward the electrode positioned in the microfluidic trapping region. Optionally, more than two electrodes can be utilized. Optionally, the substrate molecules comprise a chromophore and the ionic reaction product molecules comprise the same chromophore. For particular embodiments, the detector detects absorption of light by the ionic reaction product molecules, emission of light from the ionic reaction product molecules or both and/or the detector detects the ionic reaction product molecules in the microfluidic trapping region electrochemically. For certain of the embodiments where the ionic reaction product molecules are detected electrochemically, the electrical potential is an AC potential with a DC bias.

Also provided, in an aspect, are systems for detecting a target analyte. A specific embodiment of this aspect comprises: a microfluidic device comprising: a microfluidic channel and at least two microfluidic side channels positioned in fluid communication with the microfluidic channel; a binding surface positioned in the microfluidic channel; a semi-permeable membrane positioned in a first of the at least two microfluidic side channels, the semi-permeable membrane having a surface oriented toward the microfluidic channel; a first electrode positioned in the first of the at last two microfluidic side channels, the first electrode positioned such that the semi-permeable membrane is positioned between the first electrode and the microfluidic channel; a second electrode positioned in the microfluidic channel or in a second of the at least two microfluidic side channels; and a detector positioned to detect ionic molecules comprising a chromophore in front of, at the surface of, or within the semi-permeable membrane. A specific embodiment further comprises a voltage supply in electrical communication with the first and second electrodes, for example providing an electrical potential between the first and second electrodes, such that the ionic molecules comprising the chromophore are attracted toward the first electrode.

Figure 14:
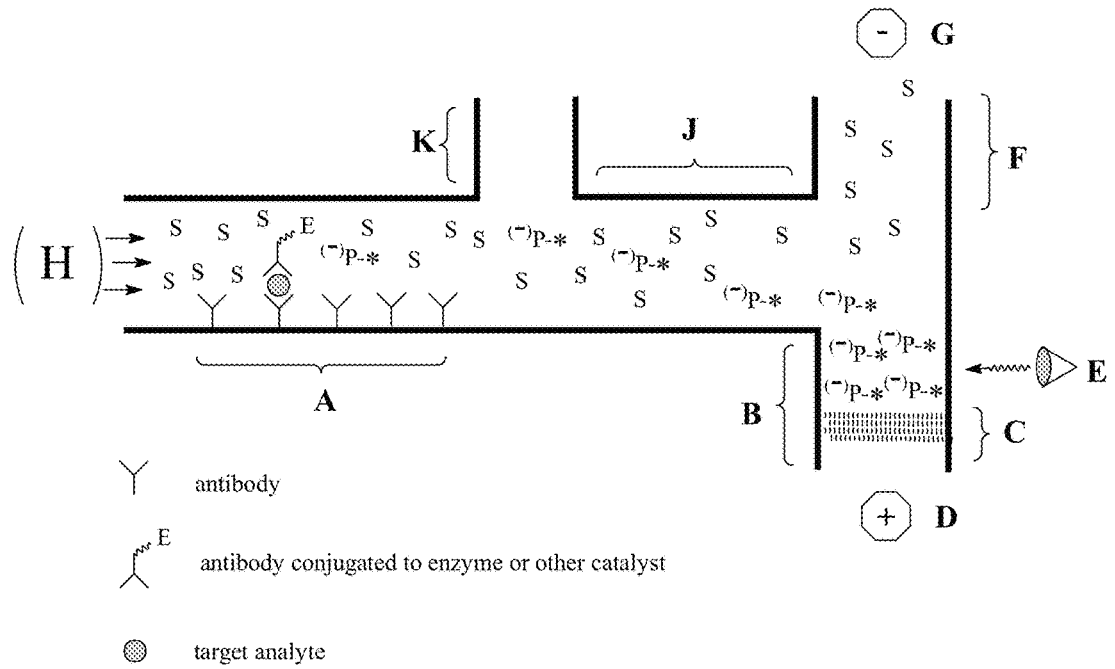
FIG. 14 shows a schematic illustration of an exemplary design further embodiment.

FIG. 14 shows structure of a device according to this embodiment. The device comprises at a minimum two microfluidics channels; one of the two channels (the channel) includes regions A, optional region J, and Region F, while the second of the two channels ("the trapping channel" also referred to herein as the "microfluidic trapping region") is labeled as B; as noted below, the two channels may be arranged in other geometries than that shown here. Region A may be described as the "ELISA" region, but may be more broadly defined as a binding region. IN an assay, this region is formed by using methods known in the art to attach antibodies to the surface of the channel in region A, followed by a wash and subsequent exposure to a sample containing the target analyte of interest (delivered from Reservoir H) wherein the analyte will bind to at least a portion of the antibodies on the binding surface. After a suitable incubation period, the channel is washed again to remove excess sample matrix, then a second antibody, conjugated to an enzyme or other catalyst, is introduced so as to form a sandwich complex between the first antibody, the antigen/target analyte, and the antibody-enzyme conjugate. A final wash to remove excess antibody conjugate will provide the ELISA region, A, in which there is bound analyte, and approximately one enzyme/catalyst for each analyte. A microfluidic side channel B (the trapping channel) comprises a semipermeable membrane, C, that allows the passage of small ions such as inorganic buffer components, but that traps larger molecules such as the detectable ELISA product in a detection zone that includes the face of the semipermeable membrane and extends out some small distance. On the side of this membrane opposite to the microfluidic channel in this embodiment (the rear) there is an electrode D the polarity of which is chosen to be opposite of the detectable ELISA reaction product. In the embodiment discussed, the detectable ELISA reaction product is given a negative charge and thus electrode D is set to a positive potential (high voltage). The potential at electrode D is sufficiently high that it can strongly attract the detectable ELISA reaction product even in opposite to a pressure driven flow passing from reservoir H through the waste channel F. Microfluidic channel B is also provided with a detection system E that is placed o as to detect species at or near the surface of semi-permeable membrane C. The electrode complementary to D is electrode G, shown in the Figure at the end of waste channel F. A general purpose reservoir/entry is provided at H, which is used to supply the various components of the assay. Components J and K (a downstream channel and an auxiliary microfluidic channel) are not essential to the operation of all embodiments.

In embodiments, systems of this aspect further comprise a solution in the microfluidic device comprising the ionic molecules comprising the chromophore, substrate molecules comprising the chromophore or both. For example, in one embodiment, the ionic molecules comprising the chromophore are reaction products of a reaction of the substrate molecules comprising the chromophore at the binding surface.

For certain of the above described embodiments, the substrate molecules are non-ionic; in other embodiments, the substrate molecules and reaction product molecules are ions having charges of opposite sign. In exemplary embodiments, the semi-permeable membrane impedes the movement of the reaction product molecules toward the at least one electrode positioned in the microfluidic trapping region.

Optionally, for the above embodiments including a semi-permeable membrane, the semi-permeable membrane comprises a silicate; a polymer selected from the group consisting of polyacrylamide, polyester, polyamide, polyacrylate, polysiloxane, polyethylene glycol, polypropylene glycol, polysuccinate, polyglycidyl, polystyryl, polypyridyl and any combination or copolymer of these; or any combination of these. For the above embodiments including a semi-permeable membrane, the semi-permeable membrane is optionally positioned between the binding surface or microfluidic channel and the electrode in the microfluidic trapping region. For the above embodiments including a semi-permeable membrane positioned in a microfluidic side channel, a surface of the semi-permeable membrane is positioned at a distance from the microfluidic channel selected over the range of 0 to 1 cm, for example over the range of 10 μm to 2 mm or over the range of 100 μm to 1 mm.

The invention may be further understood by the following non-limiting examples.

EXAMPLES

Example 1

Fabrication and Characterization of a Microfluidic Device using Electric field Assisted Rapid Analyte Capture Provided is data showing an enhancement in the sensitivity of microfluidic ELISAs upon rapid capture of antigens on an assay surface using a lateral electric field.

Section 2.1 Device Design: The microchip device used in our preliminary work comprised 8 straight glass channels each 30 μm deep, 0.5 mm wide and 1.5 cm long (see FIG. 1(b)). A pair of gold electrodes was deposited on the top and bottom walls of these channels to realize the desired lateral electric field. In this design, the top electrode (shaded brown in FIG. 1(b)) was fabricated by depositing a ~100 nm layer of chromium followed by a ~30 nm layer of gold on the surface of a wet-etched glass microchannel using a dual metal evaporator system. The bottom electrode on the other hand was patterned as a narrow strip (100 μm wide and 2 cm long) on the cover glass plate following the same process. The two electrodes were finally aligned prior to bonding the glass plates under ambient conditions. The details on the microchip and electrode fabrication procedures can be found in previous publications.

Figure 2A:
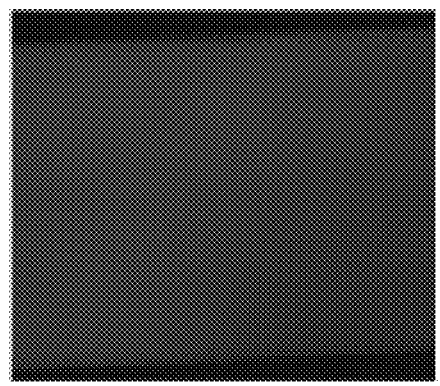
FIG. 2A provides data comparing fluorescence images of 30 μM rhodamine B solution, with the top image corresponds to measured fluorescence without the gold electrodes and the bottom image corresponds to fluorescence images with the gold electrodes.
Figure 2A:
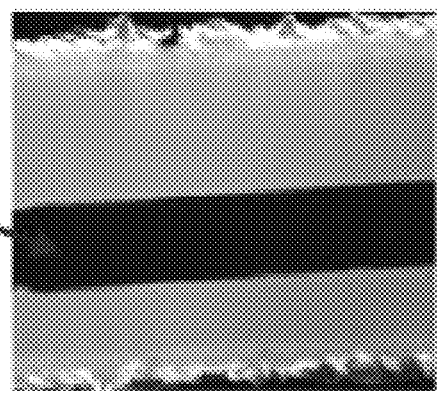
Figure 2B:
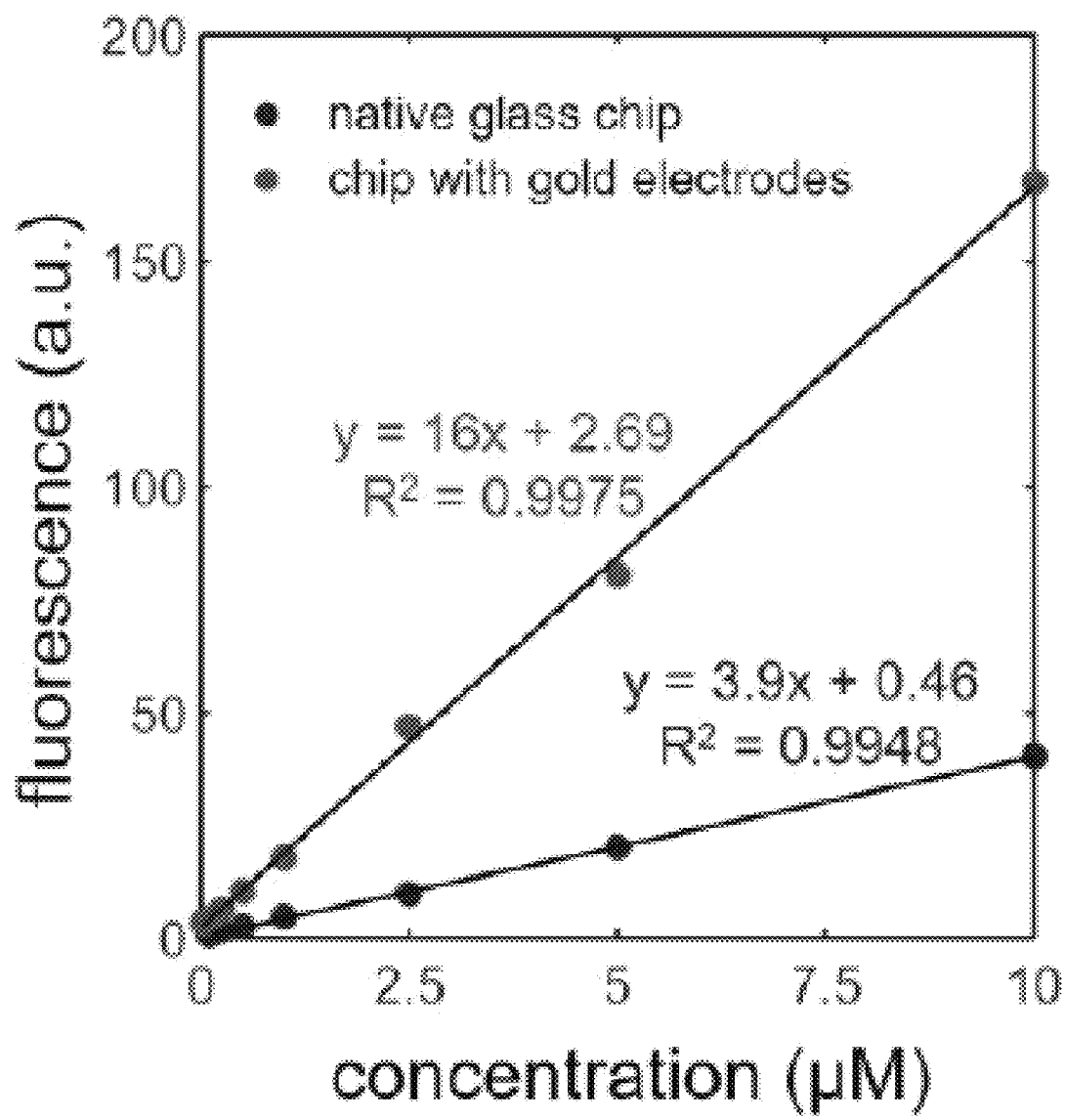
FIG. 2B provides a graphical representation of data shown in FIG. 2A, which is measured fluorescence for rhodamine B (dye) solutions in the channels with gold electrodes (top line) and without gold electrodes (bottom channel).

2.2 Enhanced fluorescence detection in microchannels with patterned electrodes: Interestingly, we observed an enhanced fluorescence from rhodamine B solutions (prepared in a 0.1 M sodium phosphate buffer, pH 7.4) upon their introduction into the microchannels with the patterned electrodes. In FIG. 2, a couple of representative fluorescence images have been included to illustrate this observation along with the fluorescence response curves for rhodamine B solutions of varying concentrations measured in a 30 μm deep glass channel with and without the gold electrodes. In general, the glass channels with the patterned electrodes were measured to yield a 4-fold higher signal compared to the ones without the metal layer. This likely occurred due to a greater fraction of the incident (excitation) radiation being absorbed by the dye molecules as a result of their reflection by the electrode surface on the top channel wall. Moreover, the same electrode also reflected much of the emitted luminescence by the rhodamine B species arriving at its surface towards the detection system (CCD camera) further brightening the channel images as seen in FIG. 2(a). Overall, the detection limit for the rhodamine B species was determined to reduce from 10 nM to 2.5 nM going from a channel without the electrodes to the one with the metal layers. Notice that the microchannels were always illuminated from the bottom end in our epi-fluorescence microscope system and the resulting luminescence also collected from this end using a 10× objective.

2.3 ELISA procedure: Following the measurements described above, the electrode surface and the native glass wall within the microchannels were chemically modified to perform ELISAs for quantitating standard samples of human TNF-α. To this end, the glass channels were prepared by sequentially rinsing with 0.1 M sodium hydroxide, deionized water and methanol for 15 min. each before modifying the gold electrodes with thiourea for an hour under ambient conditions. 3-aminopropyltriethoxysilane was later introduced into the channels and incubated again for an hour to derivatize the native glass surface. This step was followed by reacting the gold and glass surfaces with an aqueous solution of 5% (w/v) glutaraldehyde (1 hr) and then treating the microchannels for an hour with a 5 μg/mL solution of a monoclonal capture antibody to human TNF-α (MAb1 from BD Biosciences) prepared in a 0.1 M sodium carbonate buffer (pH 9.6). At this point, the unreacted sites on the channel surface were capped off by sequentially reacting them with a 1% BSA and 0.1 M lysine solution (each prepared in the 0.1 M sodium carbonate buffer) for an hour each to minimize non-specific binding of unwanted proteins. Subsequently, standard samples containing known amounts of human TNF-α prepared in a 10 mM sodium phosphate buffer (pH 7.4) were introduced into the microchannels followed by incubating them for an hour with a 0.1 μg/mL solution of a biotin conjugated detection antibody (MAb11 from BD Biosciences) to the analyte again prepared in the 0.1 M sodium phosphate buffer for an hour each. An electrical voltage difference of 1 V was applied between the electrodes only during the sample (human TNF-α) incubation step to enable rapid capture of the analyte molecules. Notice that a lower ionic strength sodium phosphate buffer, i.e., 10 mM, was used during this period as it did not lead to any noticeable electrolytic gas generation at the electrodes. The ELISA surface was finally completed by reacting it with a streptavidin-horseradish peroxidase (HRP) conjugate again for an hour under ambient conditions. The reported assay was quantitated by measuring the fluorescence signal generated upon introduction of an HRP substrate solution that contained 10 μM Amplex Red and 5 μM hydrogen peroxide in a 0.1 M sodium phosphate buffer. The enzyme reaction was carried out by maintaining an air-temperature of 37° around the microchip using a heating fan. The fluorescence signal in the assay compartment was measured using an epi-fluorescence microscope system (Nikon) employing band-pass excitation (528-553 nm) and emission (590-650 nm) optical filters. The microchannels were exposed to the excitation beam for ~1 s using a mechanical shutter to prevent any photo-bleaching of the enzyme reaction product. Fluorescence images obtained with a 10× objective were recorded using a CCD camera every 5 minutes over a 30-minute period to monitor the kinetics of the enzyme reaction. A camera exposure time of 100 ms was chosen in all our measurements which were quantitated by analyzing the fluorescence images using the Adobe Photoshop software. It was generally observed that the fluorescence intensity in the recorded images increased linearly with the enzyme reaction time and this temporal rate of increase in the fluorescence intensity was proportional to the TNF-α concentration in the sample. In this situation, the noted temporal rate for a TNF-α sample minus the corresponding quantity for a blank solution was used as a measure (referred to as the "assay signal" in this document) for quantitating the analyte concentration in our ELISAs.

Figure 3A:
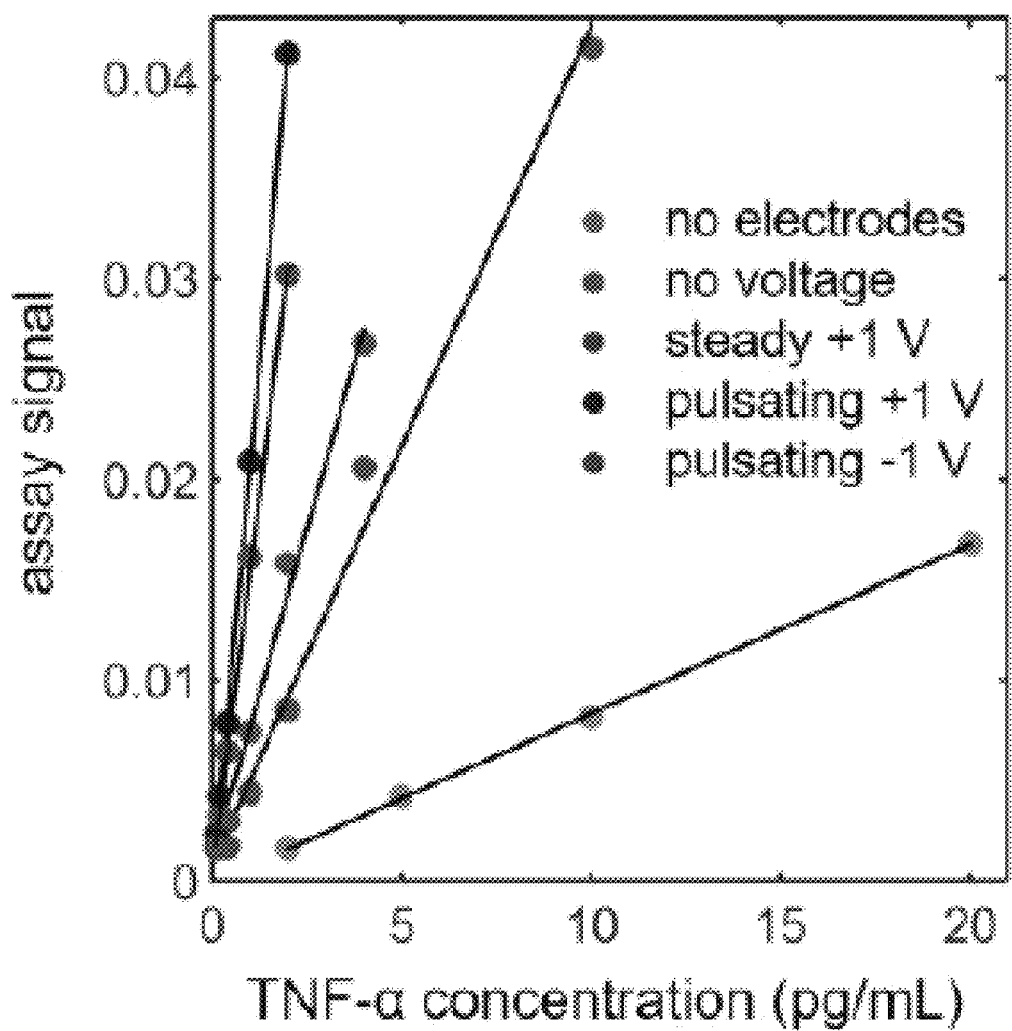
FIG. 3A provides a graphical representation of the enhancement of ELISA sensitivity upon application of a lateral electric field across the channel depth. +1 V corresponds to the situation when the electrode at the bottom channel wall was at an electric potential 1V higher than the electrode at the top channel wall. The −1 V case corresponds to the situation with the reverse electrical polarity. All data points were obtained in channels patterned with gold electrodes. The data set shown by the line to the farthest right of the graph was objected in glass channels without the patterned metal layers. From left, the results show that the highest sensitivity was the pulsating +1 V, the steady +1 V, the pulsating −1V, and the no voltage, with farthest to the right showing results for the no gold electrode.
Figure 3B:
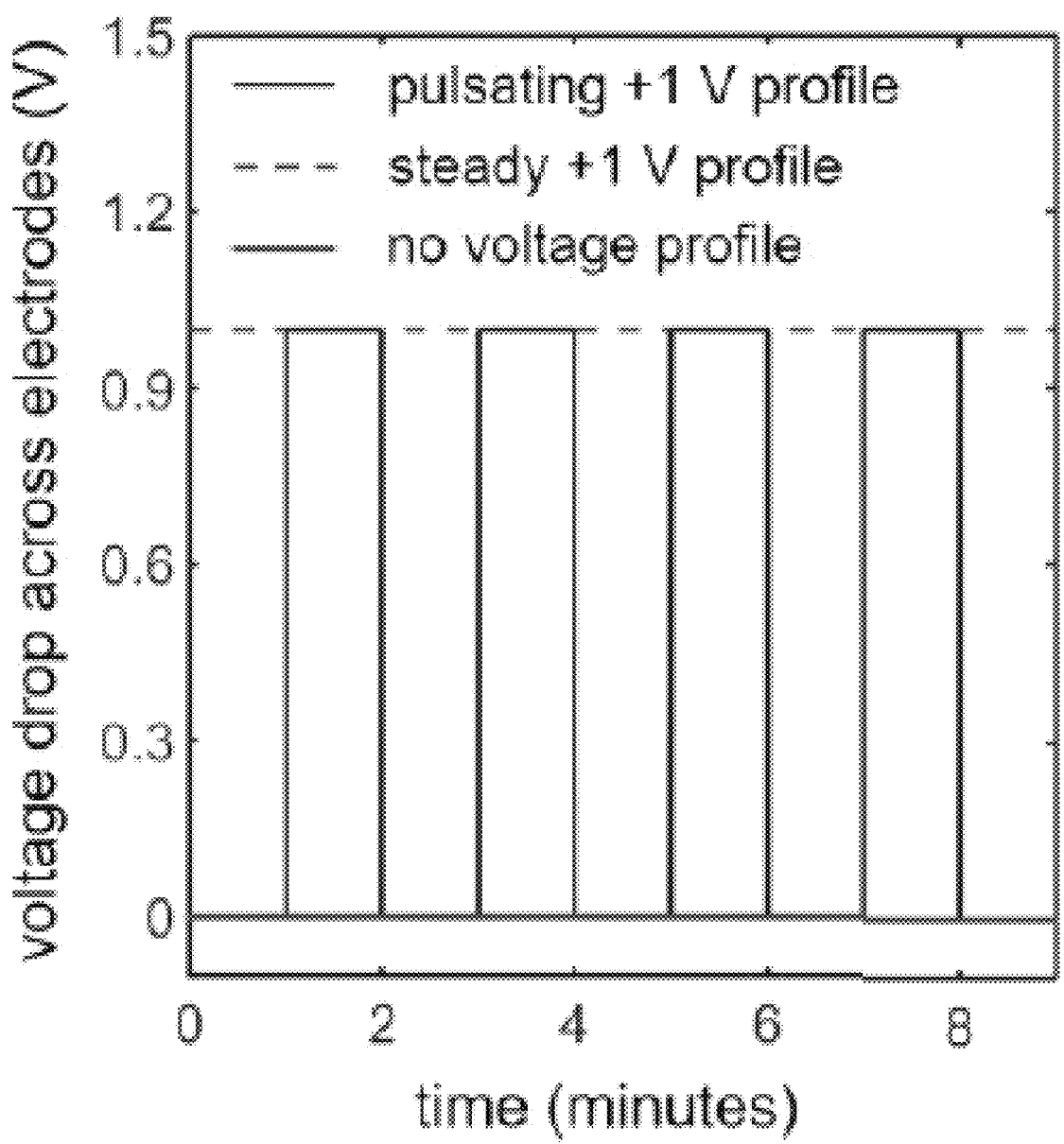
FIG. 3B provides a graphical representation of the applied voltage drop across the gold electrodes in the experiments shown in FIG. 3A.

2.4 Electric field assisted rapid capture of antigens: Initial experiments on the microchip device patterned with the gold electrodes were performed without application of any voltage drop during the sample incubation period. Unsurprisingly, these assays represented by the solid red circles in FIG. 3(a) were found to be about 4-fold more sensitive compared to the ELISAs performed in glass channels without the electrodes (grey solid circles in FIG. 3(a)) due to the enhanced fluorescence detection in our system as described in section 2.2. Proceeding further, ELISAs were performed by applying a lateral electric field during the sample incubation step to assess the effect of rapid analyte capture on the assay performance. Again, our experiments showed an improvement in the assay sensitivity by another 3.5-fold upon application of a steady 1 V across the channel depth during the hour long sample incubation period. In these experiments, the electrode at the bottom channel wall was set at a higher electric potential than the metal layer on the top wall. The noted improvement in ELISA sensitivity is hypothesized to have occurred due to electrokinetic focusing of the TNF-α molecules around the electrode surface (as shown in FIG. 1(a)) which led to a faster, and thereby capture of a greater fraction of the antigens, over the hour long sample incubation step. Interestingly, if this steady voltage profile was switched to a pulsating one comprising 1 min. long pulses each separated by a minute gap, the assay becomes even more sensitive, i.e., by about 4.5-fold relative to ELISAs performed in a glass channel with patterned electrodes but without any voltage application during the sample incubation period. Furthermore, if the electrical polarity at the electrodes is reversed during the sample incubation step, we still observe an improvement in the assay sensitivity compared to ELISAs performed without voltage application but now only by about 1.8-fold. These observations indicate a complex interplay between the electrophoretic, electroosmotic and diffusive transport of the antigen molecules with the binding process at the electrode surface in the presence of the lateral electric field, which needs to be comprehensively understood to tap the complete potential of our voltage-driven analyte capture strategy.

Figure 4B:
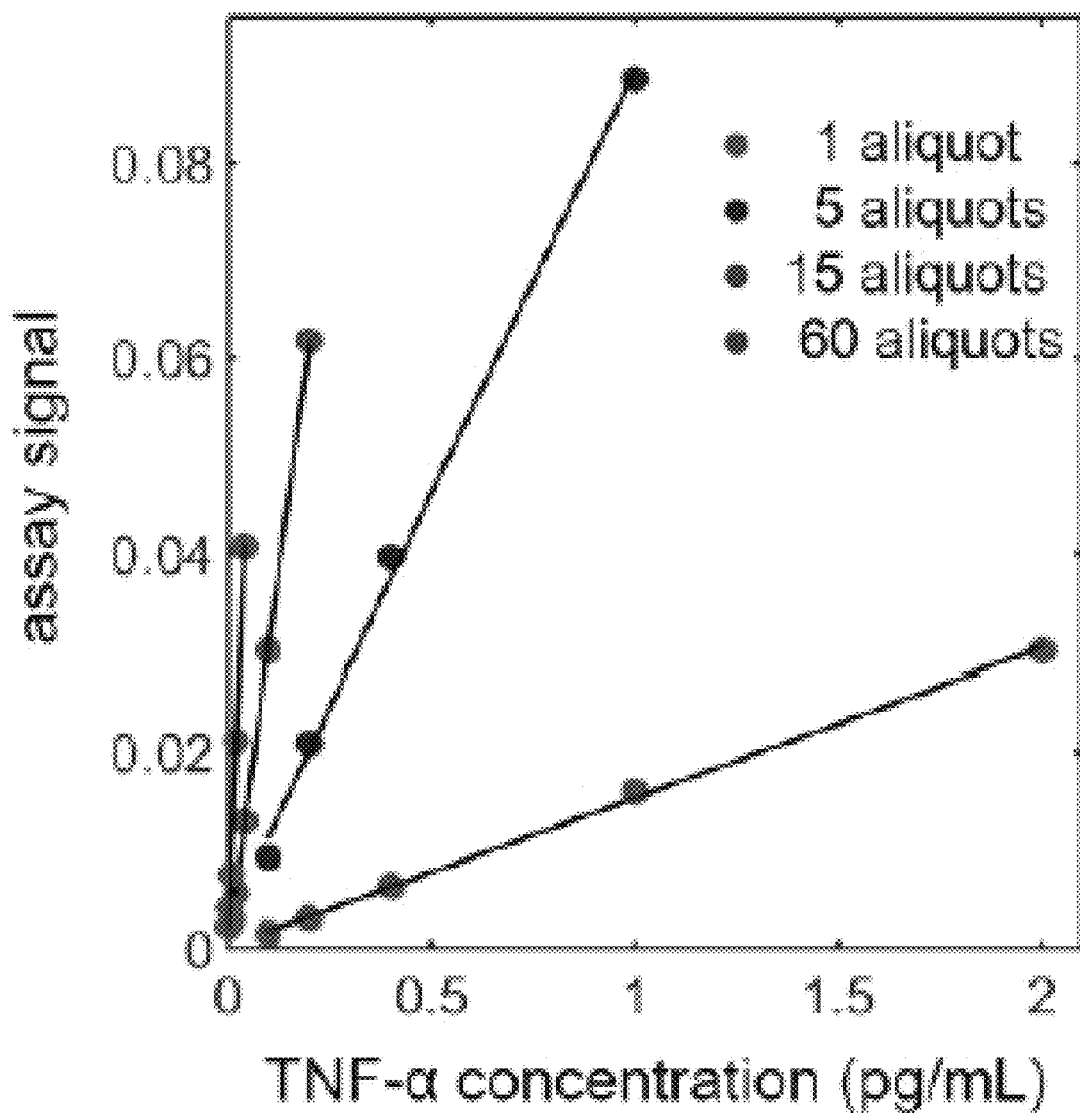
FIG. 4B shows a graphical representation of enhancement in assay sensitivity upon incubation of multiple sample aliquots, each for a minute, under the influence of a steady +1 V voltage drop applied across gold electrodes. Starting from the farthest right is shown 1 aliquot, 5 aliquots, 15 aliquots, and 60 aliquots.

2.5 Improvement in assay sensitivity through of incubation of multiple sample aliquots: The electrokinetic focusing of the analyte molecules around the electrode surface was not only expected to increase the capture of a greater fraction of this species but also significantly speed-up the noted antigen capture process due to reduced mass transport limitations. To assess the latter effect we measured the assay signal for TNF-α samples incubated for different periods under the influence of a steady 1 V voltage drop applied across the electrodes. Interestingly, the assay signal was observed to decrease in these experiments only when the sample incubation time was reduced below 1 min. for all of the chosen TNF-α concentrations (see FIG. 4(a)) suggesting the completion of the analyte capture process within the first minute of incubation. In order to translate this reduction in the antigen capture time to a higher assay sensitivity we then incubated multiple sample aliquots against the electrode surface thereby proportionally increasing the amount of antigens captured on it. The strategy of incubating multiple sample aliquots indeed reduced the detection limit for our ELISAs even further from 0.15 pg/mL to 2.5 fg/mL upon employing 60 aliquots versus 1. Notice that in the experiments reported in FIG. 4(b), each of these aliquots were incubated for 1 min. applying 1 V across the gold electrodes.

Using these devices and methods, we will work to obtain a detailed fundamental understanding of the EFARAC process and its application to designing highly sensitive and/or rapid immunoassays. While the rapid capture of antigens on an electrode surface under the influence of a lateral electric field as described above is undoubtedly promising, our preliminary experiments show that this process is likely complicated due to the generation of electroosmotically-driven liquid circulations in the assay chamber. In this situation, it is imperative to develop a comprehensive understanding of the noted process in order to maximize its potential for enhancing the sensitivity and/or tuning the dynamic range of fluorescence based heterogeneous immunoassays. One aim will therefore focus on developing such an understanding employing experimental means and theoretical simulations performed using the commercial COMSOL package. The knowledge acquired from this study will be subsequently utilized for arriving at the optimum geometry/dimensions for the assay chamber as well as the temporal profile and magnitude of the lateral electric field that most effectively enables antigen capture on an electrode surface. Alternatively, we will also assess the use of the proposed analyte capture strategy for minimizing the total assay time in quantitating an antigenic species. Because this time duration is often determined by the incubation period for the sample followed by that for the detection antibody, it should be possible to shorten each of these periods to less than a minute using a lateral electric field. We anticipate the total assay time to be reduced to less than 5 minutes in this situation which would be particularly attractive in applications such as rapid detection of biological warfare agents. In the final task, we will develop a microwell platform for our EFARAC immunoassays that can be directly quantitated using a commercial microplate reader to render our technology more accessible to biological researchers. Interestingly, the PI's research group has previously developed a similar platform for standard fluorescence based ELISAs performed in glass microchannels. Following the design strategy adopted in that work, we propose to accomplish the same goal for EFARAC immunoassays in this project simplifying assay quantitation and improving the throughput of our system.

Further Development of assays using Electric field Assisted Rapid Analyte Capture.

Figure 5:
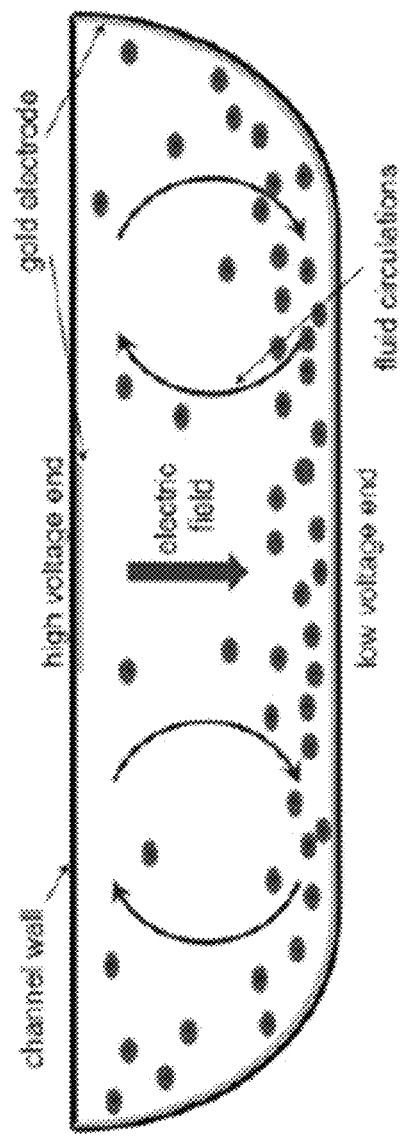
FIG. 5 provides a depiction of the hypothesized advective flow field and concentration distribution of a cationic solute across the channel cross-section.

Task 1: Experimental and theoretical characterization of the EFARAC process. These experiments will focus on determining the electric field distribution and the electrokinetic transport process occurring within the assay channel in the presence of a lateral electric field. For determining the electric field distribution in our conduit, the temporal profile for the electrical current will be monitored for a steady as well as a pulsating voltage waveform. A function/arbitrary waveform generator coupled to a voltage amplifier (TEGAM Inc.) will be used in these experiments to realize a steady as well as a pulsating voltage drop across the electrodes. A PicoAmmeter (Keithley Inc.) will be integrated to the circuitry to then measure the current variation with time for different channel depths (10-100 μm) and sodium phosphate buffer concentrations (1-100 mM). Of particular interest here will be to determine any phase shift and/or a reduction in the amplitude of the electrical current (relative to the voltage) over time due to accumulation of buffer ions around the electrode surface [27,28]. We anticipate applying voltage-drops <1.5 V (peak-to-peak) at frequencies 0.001-10 Hz in these measurements without electrolytically generating any noticeable amount of gas bubbles. In addition, we will monitor the Joule heating of the electrolyte between the electrodes using fluorescent-dye based thermometry techniques described in the literature [29-31]. While we do not anticipate any significant heat generation in our system, the objective of this study will be to ensure that the temperature variation across the channel depth in our assays is kept below 1° C. to prevent any undesirable effects of heat generation on antigen binding or their transport to the electrode surface. As part of this task, we will also determine the dominant electrochemical reaction occurring at the gold surface for a phosphate buffer solution using the cyclic voltammetry method. The liquid flow profile across the channel depth will be assessed in our study using the confocal microscopy and particle velocimetry techniques. A commercial software, e.g., through Dantec Dynamics, will be used to analyze the images obtained at different planar positions between the electrodes allowing the determination of the 2D advective velocity field in this region. In separate experiments, electrically charged as well as neutral fluorescent dye tracers and large proteins will be introduced into the phosphate buffer to perform confocal imaging of their steady state distribution across the channel depth in the presence of a lateral electric field. The noted experiments will be performed for various voltage drops (both steady and pulsating) and buffer ion concentrations (e.g., 1-100 mM) to create an understanding of mass transport in our system. The experiments described above will be complemented with numerical simulations performed with the commercial COMSOL package. A mathematical model for our system will be built from this effort that would satisfactorily describe the charge and mass transport in our system (see FIG. 5). This model will be later applied to arrive at the optimum geometry/dimensions for the assay chamber as well as the temporal profile/magnitude for the voltage drop that allows the most efficient capture of the antigenic species on the electrode surface. If our simulations indeed guide us to conditions under which the electrokinetic capture of antigens can be significantly improved, experiments will be performed to validate those predictions through redesign of the assay chamber and/or voltage profile. The extent of analyte capture on the electrode surface will be experimentally determined in our study through confocal imaging of the channel walls after incubating them with a dye labeled antigen in the presence and absence of a lateral electric field.

Application of the EFARAC Technique to Designing Rapid Immunoassays.

Task 2: These experiments focus on developing the fastest immunoassay possible employing a lateral electric field across the channel depth for a given assay sensitivity. The total assay period in most immunoassays is often dictated by the incubation time for the sample as well as that for the detection antibody. Based on our preliminary data, it should be then possible to reduce the duration for each of these steps down to a minute or less using a lateral electric field. We will work towards accomplishing this goal in the current task applying the optimum assay conditions arrived at from task 1. Immunoassays employing both dye and enzyme labels conjugated to the detection antibody will be developed as part of this effort. Notice that while the enzyme labeled version of this immunoassay (ELISA) may be more attractive in terms of sensitivity, it will likely have a longer assay time (~30 min.) which now will be dictated by the enzyme reaction period in the system. In this regard, our move to integrating ECL detection methods to the EFARAC immunoassays as proposed in Specific Aims 2 & 3, is an appropriate one for detecting antigenic species with sensitivities similar to or better than that realized using ELISA methods but with overall assay periods of about 5 min. Finally, the validity of the proposed approach to performing immunoassays of practical interest will be established by applying it to assessing the levels of a panel of cytokines, e.g., TNF-α, IFN-γ, IL-1, IL-4 and IL-10 in human serum samples. The performance of these assays will later be assessed by comparing their figures-of-merit, e.g., detection limit, dynamic range, calibration sensitivity, etc., to those for their standardized counterparts carried out on microwell plates and quantitated with a commercial microplate reader.

Development of an EFARAC Immunoassay Platform Compatible with a Commercial Microwell Plate Reader.

Figure 6:
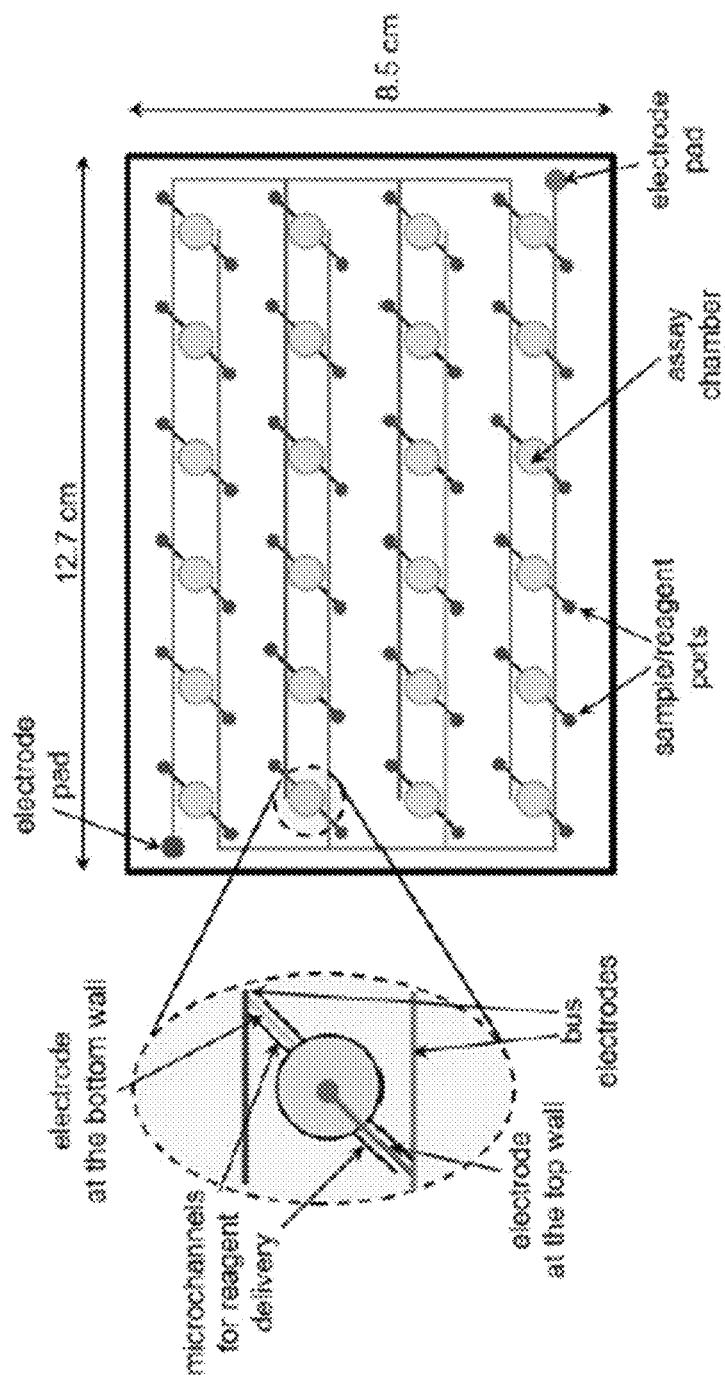
FIG. 6 provides a schematic of the proposed EFARAC immunoassay platform compatible with a commercial microwell plate reader.

While the implementation of EFARAC immunoassays in microchannels is relatively simple, their quantitation cannot be performed using standard commercial microwell plate readers. This shortcoming can render the proposed immunoassay method less accessible to biological researchers diminishing its overall impact. The final task of this specific aim will therefore focus on developing an EFARAC immunoassay platform that can be quantitated using a commercial microwell plate reader. We have included a preliminary design for this platform in FIG. 6 that essentially comprises 48 cylindrical assay chambers on a footprint size identical to that of a commercial 96 microwell plate. By choosing the locations of these chambers to overlap with some of the microwells on the commercially available assay plate, it should be possible to read the fluorescence within them using the detection system/software of the plate reader. The PI's group has previously published the development of a similar platform for quantitating ELISAs performed in glass microchannels with a commercial plate reader based on a similar approach [20]. For the current project however, we will need to modify that design to incorporate the planar electrodes on the top and bottom walls of the assay chamber. The actual dimensions of the chamber and electrodes will be arrived at in our design based on COMSOL simulations. Nevertheless, we anticipate the diameter of the chamber to be a few millimeters while its height to be in the range of 10-100 μm. The proposed immunoassay platform will be constructed using glass plates employing standard photolithographic and wet-etching methods [32,33]. The planar electrodes will be deposited using a dual metal evaporator system following processes similar to that employed in our preliminary work and previously published by the PI [23, 24]. As before, the EFARAC process will be realized on this platform by applying voltage drops in the range of 0.5-1.5 V across the electrodes on the top and bottom walls. The utility of this platform will be assessed by comparing the performance of immunoassays performed on it to those carried out on commercial microwell plates.

Example 2

Synthesis of new Reporter Antibody-Catalyst Conjugates (RACCs) for Sensitive ECL Detection and their Incorporation into the EFARAC Immunoassays Developed in Specific Aim 1

Figure 7A:
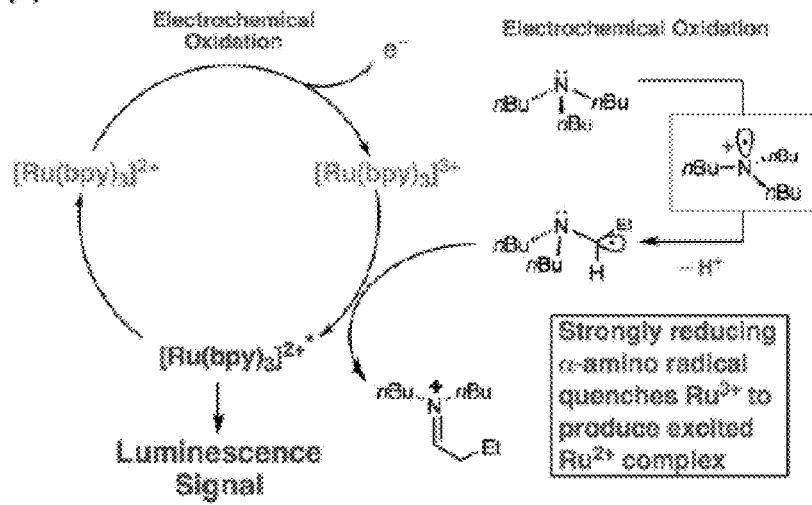
FIG. 7A shows the ECL redox cycle with the Ru(bpy)$_3$/TPA redox system.
Figure 7B:
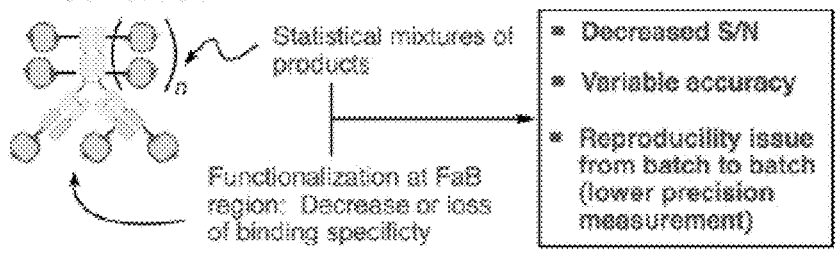
FIG. 7B shows the current art for RACC synthesis utilizing non-specific antibody labeling.
Figure 7C:
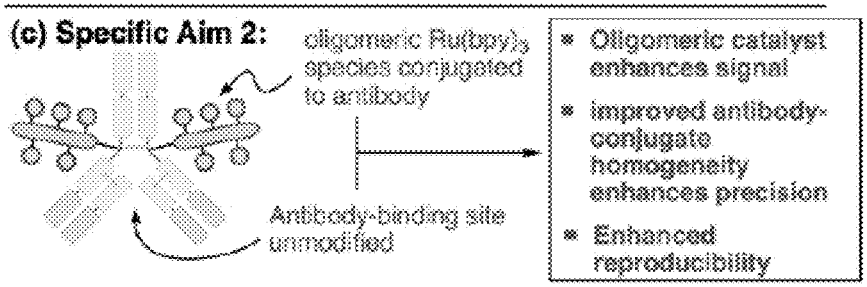
FIG. 7C shows the present invention's proposed synthesis of highly ordered RACCs containing redox catalyst oligomers.

The focus is to integrate ECL detection methods into our immunoassay by employing the electrodes used for analyte capture to also trigger ECL reactions. Interestingly, current ECL immunoassays have been claimed to have similar or lower detection limits compared to fluorescence based ELISA methods. In this situation, the proposed integration can only add to the sensitivity, dynamic range and simplicity of the EFARAC immunoassays developed in Example 1. Furthermore, the means by which ruthenium catalysts are incorporated into detection antibodies in current ECL immunoassays is comparatively crude relying on non-specific lysine functionalization with Ru(bpy)3-catalyst derivatives possessing activated esters. In this situation, given the high abundance of lysine residues in these systems (>40 reactive residues on IgG1), it is not surprising that such conjugates are well precedented for giving statistical mixtures of products. While this approach benefits from comparative simplicity, the heterogeneity of products inherent to this approach can lead to a number of undesirable properties including 1) loss of binding activity due to functionalization at the binding site and 2) statistical variability in the catalyst to antibody ratio from batch to batch, which can then significantly increase the measurement error (noise). We propose to address the aforementioned issues through the development of a rational design and synthesis strategy for RACCs relevant to ECL detection methods. In particular, we will pursue the synthesis of peptide based catalyst oligomers which will be chemically appended to well-defined locations on an antibody (preferably in the Fc/Fab bridging region that is not involved in antigen binding) using cysteine-based conjugation chemistry. As our design limits the sites of functionalization on the antibody, we will synthesize well defined oligomers that maximize the catalyst to antibody ratio, as the greater the number of catalysts, the greater the signal generated. Moreover, we anticipate that oligomeric catalyst structures will produce enhanced signal at lower oxidation potentials as the local proximity afforded by tethering opens up the possibility of ECL from alternative mechanisms such as mixed annihilation excitation. Example 2 details a new design and synthetic strategy for assembling ECL reporter antibodies that will deliver enhanced sensitivity under assay conditions (see FIG. 7). Current state-of-the-art commercial technologies utilize the venerable Ru(bpy)3/tripropylamine (TPA) redox system depicted in FIG. 7(a). Whilst the ECL aspect of this system is well established, the means by which the ruthenium catalyst is incorporated into the antibodies is comparatively crude; relying on non-specific lysine functionalization with Ru(bpy)3-catalyst derivatives possessing activated esters. Given the high abundance of lysine residues in these systems (>40 reactive residues on IgG1), lysine acylation results in statistical mixture of products (see FIG. 7(b)). A more ideal approach to synthesizing RACCs in this situation is to attach oligomers of catalysts to a few, well defined spots on an antibody, preferably on the Fc region that is not involved in antigen binding. Lending credence to this strategy is a singular report from Zhou, who synthesized a small dendrimer containing three catalysts, and then appended this to BSA. Our proposed design involves the synthesis of peptide-based catalyst oligomers, which are then appended to the antibody site-specifically. The precious and bespoke nature of reporter antibodies renders the use of genetic modifications impractical, thereby requiring effective chemical tools for modification of the native antibodies. Therefore, our design features the development of novel strategies for the site-specific functionalization of native antibodies using cysteine-based conjugation chemistry. As our design limits the sites of functionalization on the antibody, we will synthesize well defined oligomers that maximize the catalyst to antibody ratio as greater the number of catalyst per antibody, greater the signal generated. Moreover, we anticipate that oligomeric catalyst structures will produce enhanced signal at lower oxidation potentials as the local proximity afforded by tethering opens up the possibility of ECL from alternative mechanisms such as mixed annihilation excitation [38].

Figure 8:
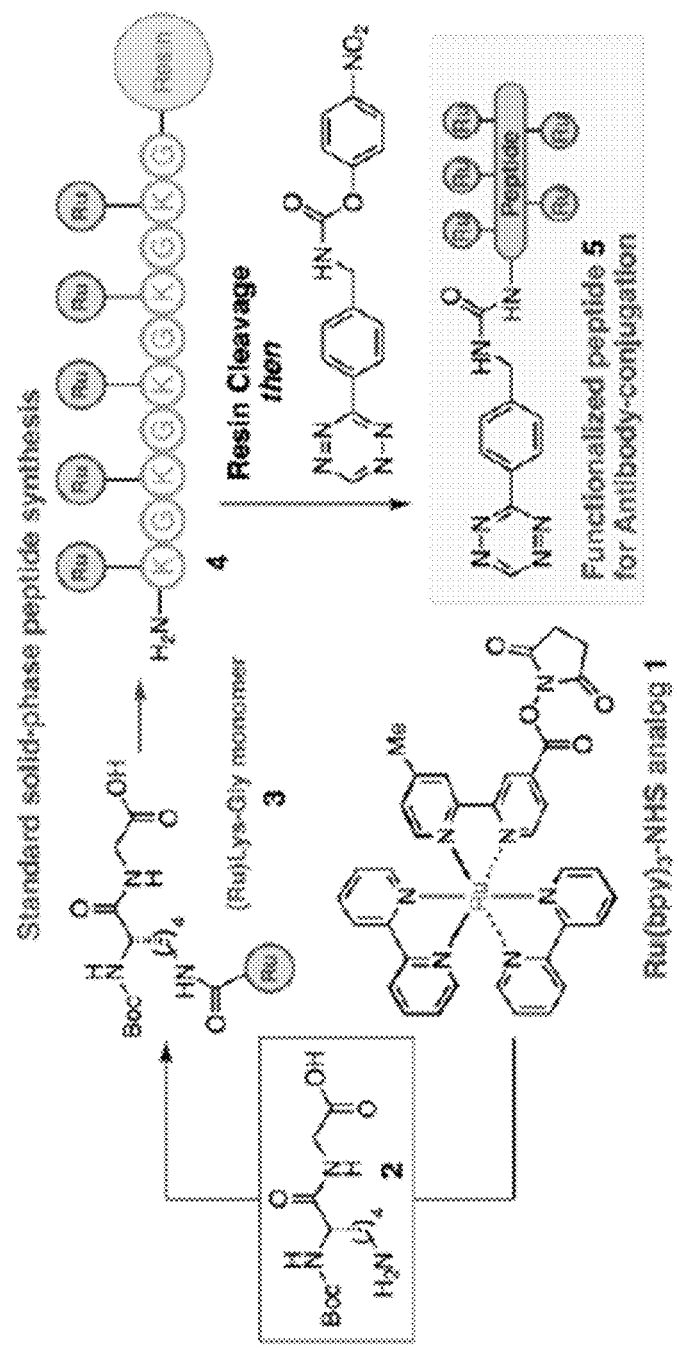
FIG. 8 shows synthesis of product 5 using standard peptide-coupling conditions.

Task 1: Synthesis of modular, peptide-Ru(bpy)3-based catalyst oligomers. Our oligomer-catalyst design is peptide-based, allowing for the use of the iterative coupling/deprotection strategy of standard peptide synthesis chemistry to rapidly assemble well defined oligomeric systems. Specifically, we will synthesize catalyst-5-mer 4 shown in FIG. 8, using the dipeptide precursor 3. 2 in turn can be easily prepared from established Ru(bpy)3 derivative 1. An advantage to this strategy over polymerization strategies stems from both the highly defined nature of the oligomer and the modularity of the process: we can easily vary linker-lengths (our initial design uses glycine) and chemical properties by simply exchanging the linker without having to modify synthetic conditions. Synthesized oligomers can be readily characterized by mass-spectrometry, UV-Vis absorbance measurements, and analyzed in solution-phase for ECL activity. At the end of the solid phase peptide synthesis sequence, we will incorporate a biorthogonal handle, such as a tetrazine derivative (available in 1 step from commercial materials), to yield 5, which can then be conjugated to an antibody.

Figure 9A:
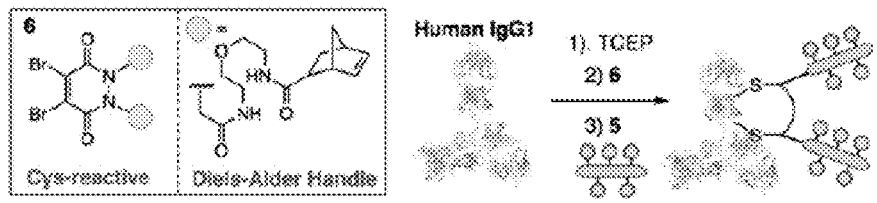
FIG. 9A shows a cysteine-rebridging reagent 6 for synthesizing RACCS.

Task 2: Development of an improved conjugation strategy for attaching 5 to a model antibody. As many reporter antibodies are precious, we will develop/adapt a cysteine-based strategy for antibody conjugation using human IgG1 as a model substrate. Cysteine has much lower abundance and superior nucleophilic properties than lysine, and can therefore be targeted with much greater precision. To quickly access material, we will exploit the "reduce and re-bridge" approach reported by Caddick by designing bifunctional probe 6 (available in 4 steps). 6 possesses an established cysteine-reactive handle for antibody conjugation, and a norbornene group which will be used to append oligocatalyst 5 to the antibody (see FIG. 9(a)) [43]. An advantage to this strategy is the "re-bridging" of reduced disulfides retaining the stability characteristics of the native antibody [42,44]. Having accessed probe 6, we will then partially reduce the disulfides in IgG [45] followed by conjugation of bifunctional probe 6, then installation of 5. While cysteine-based antibody conjugation strategies represent an advancement in technology for constructing ECL reporter antibodies, these strategies for native antibody bioconjugation still fail to produce chemically homogenous conjugates, as exemplified by Alley's report detailing both chemo- and regio-isomers of antibody conjugates formed by cysteine ligation [46]. The as-yet unsolved challenge in functionalizing a molecule as complex as an antibody stems from the sheer number of functionalizable residues (including even rare residues such as cysteine) that are present and solvent accessible to an exogenous reagent: how is one residue selected out of many? If we could find a way to "localize" a reactive agent to a specific section of a target antibody, then the reagent would be inherently limited to reacting with immediately neighboring groups by virtue of proximity induced reactivity. We posit that a more general approach than the current art [47-50] in proximity-induced reactivity can be achieved by exploiting the unique reactive properties of more "targetable" amino acids to selectively deliver a second reactive group to a protein. We will demonstrate this concept by designing a reagent that uses cysteine as a "directing group" for site-specific carboxylate activation. Specifically, we have designed bifunctional reagent 7, which consists of a cysteine-reactive, reversible Michael receptor [51], a linking group, and a carboxylate-reactive EDC.HCl equivalent [52]. The labeling process will proceed in the following sequence: 1) inter-chain disulfide reduction 2) ligation to cysteine 3) proximity-induced —COOH activation/amidation with 8, 4) trapping with oligocatalyst 5 and 5) reverse-ligation at cysteine/oxidative disulfide re-bridging. The diagnostic absorbance of Ru(bpy)3 (abs 450 nm) [53] provides a convenient method for estimating the overall level of catalyst incorporation by measuring UV intensity. Further information on modification efficiency will be collected via standard techniques such as enzymatic digestion/MS-MS.

Figure 9B:
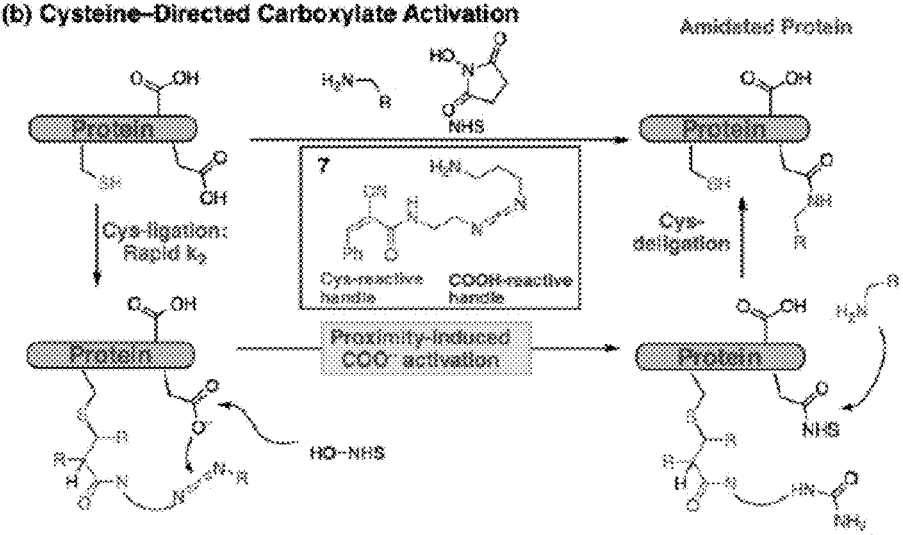
FIG. 9B shows cysteine as a directing group for antibody amidation using reagent 7.
Figure 9C:
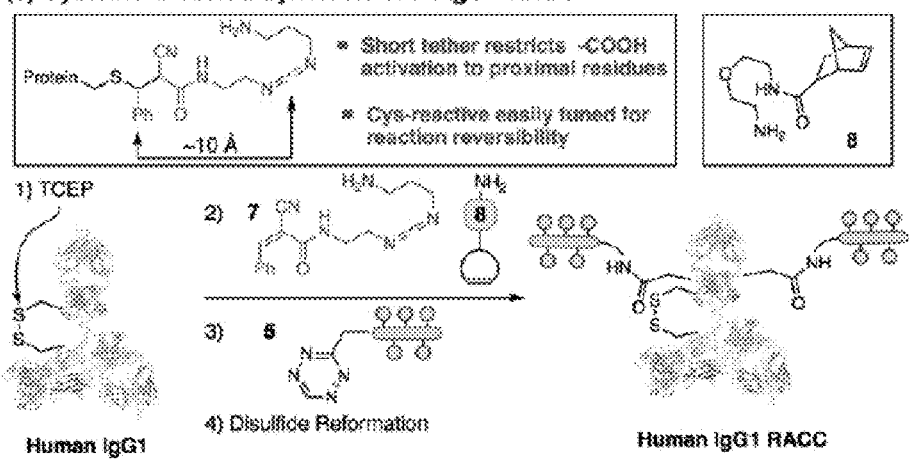
FIG. 9C shows use of reagent 7 in the synthesis of an IgG1-RACC.
Figure 10:
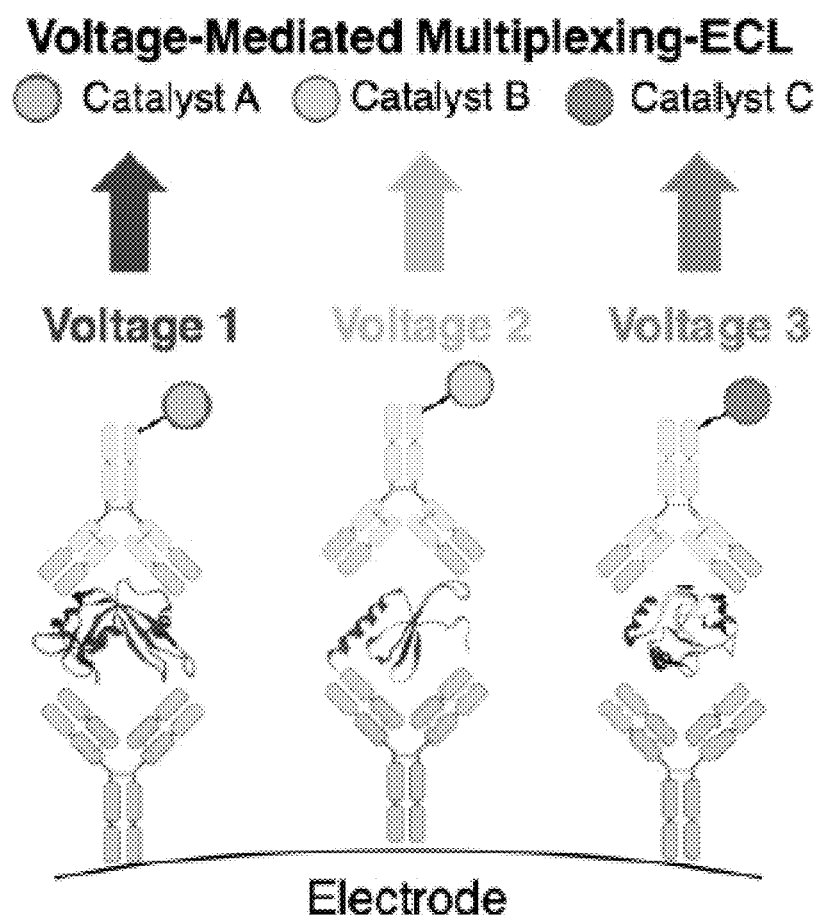
FIG. 10 shows a carton of voltage mediated multiplexing ECL, with different voltages resulting in different outputs.

Task 3: Evaluation in an ECL immunoassay. Once the approach to synthesizing the proposed RACCs is optimized, it will be applied to developing a human IgG immunoassay. To this end, commercially available antibodies will be purchased and modified with the proposed catalyst following procedures described in FIG. 9. These conjugates will be then employed as the detection antibody in a human IgG immunoassay performed on the platform developed in task 3 of Specific Aim 1. For the immunoassay, we will adapt the standard conditions reported by Xing: 100 mM PBS/100 mM TPA buffer at pH 8 doped with 0.1% Tween 20 applying a potential of +1.2 eV [18]. Once optimized we will also apply the conjugation strategy described above to performing a human TNF-α immunoassay and compare its figures-of-merit to those for a human TNF-α ELISA performed on a commercial microwell plate.

Potential challenges and alternative approaches: Whilst the Ru(bpy)3 complex has proven to be a very stable substance over a wide pH range, a potential pitfall with the synthesis of 5 stems from the potential decomplexation of the ruthenium over repeated exposure to peptide synthesis conditions. If this is found to be the case, then the synthesis can easily be altered to incorporate the redox catalyst post-peptide synthesis via lysine-NHS ester coupling. A second potential complication stems from the dicationic nature of Ru(bpy)3, wherein charge-charge repulsion could serve to hinder the efficiency of the peptide synthesis. To circumvent this issue, the peptide structure can be simply modified to lengthen the linking amino-acids in between catalysts.

Example 3

Development of Alternative Catalyst/Reductant Pairs to Expand the Multiplexing Capabilities of ECL Immunoassays Based on Voltage-Dependent ECL Activation One of the inherent challenges to fluorescence/luminescence-based multiplexing assays stems from the need for selecting appropriately orthogonal fluorophores/luminophores with respect to both emission and absorption bands. Voltage-dependent ECL circumvents this challenge by tying observed signals to the required redox potential of a given chemiluminescent process. While a partial proof-of-concept for this approach has been reported by Wang et al. by coupling the Ru(bpy)$_3$/tripropylamine and carbon nanodots/$S_2O_8^{2-}$ reporter systems, the voltage-dependent ECL multiplexing strategy has not been explored in detail. In several key respects, metallophotoredox catalysts of the given generic formula M(L)$_3$ are particularly suitable for developing voltage-dependent multiplexed ECL immunoassays as the ligand scaffolds are modular in nature and can be easily tuned to change the electronics of the complex, and many metals, such as Ir, Cu, Os, Pd, can be used, allowing for pin-point customization of the redox-potentials. This project will therefore focus on developing new catalyst/reductant pairs for ECL detection that are triggered at non-overlapping electric potentials. We will employ the high throughput microwell platform developed in task 3 of Example 1 for this screening process in which the catalytic activity of analogs of Ru(bpy)$_3$ will be investigated for oxidizing a variety of amines in which the electronics around the nitrogen and α-amino radical is perturbed from that in tripropylamine. In addition, we will also investigate alternative sources of reducing radicals such as amino acids, as well as alkyl thiols and pyridinium-amines.

The proposed research is transformative because it presents a novel and powerful approach to enhancing the sensitivity of immunoassays through rapid capture of analyte molecules using a lateral electric field. Alternatively, this electric field may be utilized to tune the dynamic range of an immunoassay or minimize the incubation period for the sample/detection antibody solution involved in the process.

We will also render our EFARAC immunoassays more accessible to biological researchers through the development of a microwell based platform for it that can be directly quantitated using a commercial microplate reader. Besides improving the figures-of-merit for an immunoassay, the proposed research will generate new fundamental knowledge on the mechanism for the electric field assisted analyte capture process outlined in this work. Moreover, ECL detection methods will be integrated to the proposed EFARAC immunoassay for the first time in an effort to further enhance its sensitivity and broaden its dynamic range. This integration will be further advanced through the rational design and synthesis of novel peptide based catalyst oligomers and their specific attachment to the Fc region of an antibody using cysteine conjugation chemistry. It is anticipated that such a strategy will help reduce the variability in the catalyst to antibody ratio from batch to batch without compromising, if not improve, the average magnitude for this quantity. This would in turn increase the signal-to-noise ratio for the assays further lowering their analyte detection limit. In addition, we will develop at least 3 new ECL catalyst/reductant pairs activated at non-overlapping electric potentials and integrate them to our EFARAC immunoassays to broaden their multiplexing capabilities based on voltage-dependent ECL activation.

Multiplexing allows for imaging and quantitation of multiple analytes in a single experiment, thus dramatically increasing analysis throughput. Traditionally, ECL immunoassays have been multiplexed by quantitating different analytes in physically separated regions using the same detection antibody/catalyst system. Alternatively, Sojic and Walt have coupled ECL with fluorescence via beads labeled with differing fluorophores to correlate ECL with differently fluorescing beads. Han et al. was able to couple luminol chemiluminescence with Ru(bpy)3 ECL for the simultaneous assaying of MCF 7 and PC 3 cells. A major challenge in ECL multiplexing stems from a lack of chemiluminescence redox systems that function under immunoassay conditions. Remarkably, the Ru(bpy)3/TPA electrochemiluminescence remains the industry standard, over 40 years after its initial discovery. During this time, the utility of redox-active catalysts related to Ru(bpy)3 has exponentially expanded, and a diverse of array of redox-active catalysts have been developed. A particularly appealing allure of ECL is the potential to perform multiplexed immunoassays based on voltage-dependent ECL activation. A partial proof-of-concept for this multiplexing strategy was reported by Wang et al., who devised an ECL assay wherein Ru(bpy)3/TPA was coupled with carbon nanodots/S2O82-, to allow for voltage-mediated ECL assay of tumor markers in human serum samples. While an elegant demonstration, the use of wide voltage window and harsh/corrosive oxidants/oxidizing radicals that can denature proteins (S2O82-/SO4-Eox=1.85 eV, 2.36 eV, respectively) inherently limits applications with chemically sensitive analytes. Metallophotoredox catalysts of the given generic formula M(L)3 are ideally suited for voltage-dependent ECL as the ligand scaffolds are modular in nature and can be easily tuned to change the electronics of the complex, and many metals can be used besides Ru, allowing for pin-point customization of the redox-potentials and luminescent properties. Hogan and Francis elegantly demonstrated this premise was indeed possible, by coupling Ru(bpy)3 analogs, with Ir(ppy)3 and [Ir(dfpy(ppy)2] and tripropylamine (TPA) as the reductant. However, these results were accrued under conditions incompatible with immunoassay requirements (organic solvent). Moreover, in each of these instances, TPA-radical was used as the terminal reductant. Whilst chemiluminescence was observed, each catalyst possesses differing electronic structures; suggesting that TPA radical may not necessarily be the optimal reductant for these catalysts. In order to enhance chemiluminescence signal for a given catalyst/reductant system, we will develop catalyst/reductant pairs which 1) function in immunoassay conditions 2) both match the reactivity of the catalyst/reductant pair, and 3) expand the viable voltage operating windows for ECL immunoassays.

Task 1: Optimization of the screening approach by reinvestigation of the Ru(bpy)3/TPA system. To facilitate the discovery of viable systems other than Ru(bpy)3/TPA for ECL under relevant conditions (aqueous buffered), we will adapt the microwell plate developed in task 3 of Specific Aim 1 to provide a robust platform that will allow for us to interrogate alternative catalyst/reductant pairs in a timely fashion. The premise is simple: instead of carrying out an immunoassay in the microwells, we will introduce about 2 μL of a solution containing the terminal reductant and the redox catalyst. The solution can then be subjected to varying voltages in search of a luminescent signal. Luminescence intensity can be recorded using a synchronized video microscope to quantify results. The top hits discovered will be taken and further optimized using the same system. Whilst the $Ru(bpy)_3$/TPA system is a proven technology in ECL, issues have been raised with its limitations. For example, ECL is criticized for the high concentration of TPA required (usually 100 mM). Moreover, the requirement for TPA also limits the pH window in which ECL can be performed (TPA pKa=10.4). Given that the mechanism of chemiluminescence (see FIG. 11(a)) requires free amine for oxidation, at physiological pH only a small amount of TPA is available for oxidation, thus requiring assay conditions of pH 8 or greater. While a large number of amines have been shown to participate in ECL with Ru(bpy)3, a truly systematic study of amine/$Ru(bpy)_3$ pairs that account for factors such as amine pKa, α-amino radical stability, reducing power, and even the source of α-amino radical is generally lacking. Given the sheer number of commercially available α-amino radical sources (amines, amino-acids, etc.), use of the rapid throughput platform will greatly facilitate optimization of an improved system. This optimization study will be conducted in a pH 7.4 (10-100 mM sodium phosphate) buffer, thus mimicking conditions relevant to immunoassays. We will broadly divide amines into classes based on steric or electronic perturbations from the parent TPA system. A representative group of amines is depicted in FIG. 11(b). Briefly, we expect electronic perturbations to significantly alter the pKb, and thus the [free amine] available for ECL, as well as the oxidation potential of the starting amine. We will investigate amines that alter the electronics at nitrogen, as well as others that perturb electronics at the α-amino radical. We expect perturbations of steric bulk of the amine alkyl chains to effect catalyst-reductant interactions as well as effect radical stability. We will also investigate the use of α-amino acids as a source of α-amino radical. Deprotonated α-amino acids undergo a single electron oxidation/decarboxylation sequence to yield an a amino radical. A particular advantage to this strategy stems from the lower pKa of carboxylic acids, which will greatly enhance the effective [reductant] under assay conditions, and also greatly expand the operation pH window.

Task 2: Optimization of alternate catalyst systems. Having optimized the ECL screening platform, we will next turn our attention towards optimization of alternative catalyst/co-reactant pairs. Typical Ru(bpy)3/TPA based assays yield peak luminescence at 1.2 eV [18]; thus, mandating that we develop systems that luminesce at different voltage windows. Different catalysts display large differences in the electronic structure, as exemplified by Ru(bpy)3 and Ir(ppy)3 whose estimated 3MLCT energies are 16.8×103 cm-1 and 19.6×103 cm-1, respectively [65]. Given these differences, it is logical to assume that different reductants will transfer electrons to different catalysts with varying levels of efficiency. Using, our rapid throughput approach, we can screen a variety of different amines, such as those depicted in FIG. 11(b), against a plethora of redox catalysts (see FIG. 12(a)). We will focus our efforts on catalyst systems with redox-couples that complement Ru(bpy)3. Specifically, we will develop assays that function in the following voltage regions 0.2-0.4 eV, 1.3-1.6 eV and 0–(−0.3) eV. A selection of potential candidates for screening is depicted in FIG. 12, all of which have redox couples distinct from those of the Ru(bpy)3 Ru(III)/(II) redox couple exploited in ECL (E1/2=1.23 eV) [53,66,67]. Using our screening platform, we intend to match reductants and catalysts based on both observed luminescence and redox potential. FIG. 12(b) illustrates some representative examples of reductants that have redox potentials matched with our desired redox windows, such as dihydropyridines (0.2-0.4 eV) [68], thiols (0.5-1.1 eV) [69,70], and secondary amides (1.6 eV) [71]. Accessing ECL under negative voltage potentials (reduction/oxidation ECL) offers differing challenges than oxidation/reduction. Strongly reducing potentials can denature biomolecules, and reduction/oxidation ECL using harsh oxidants could have the same effect [58, 72]. To address this challenge, we will develop a reduction/reduction ECL system that utilizes pyridinium-amine 9 and a strongly reducing Ir-based redox catalyst such as Ir(4-MeO-ppy)3 or Ir(btp)2acac (see FIG. 12(c)). 9 can be reduced under weakly negative potentials (E0=0.45–0.5 eV) [73] to generate an oxidizing N-centered radical which in turn will generate strongly reducing radical 10 via 1,5-hydrogen abstraction [74]. 10 can then proceed to produce luminescence via reduction of the redox-catalyst. Importantly, the strongly reducing nature of these catalysts will allow for the prerequisite Ir(IV) species for ECL via oxidation by 9a, by sacrificial oxidant 9b.

Task 3: Evaluation of voltage-dependent multiplexed ECL immunoassays. Having completed the screening process, we will proceed to take the top two hits achieved during the screening process, and apply them to an ECL multiplexing assay. Given the modular approach to synthesis of RACCs delineated in Specific Aim 2, we will rapidly be able to adapt the synthesis to incorporate the new catalytic moieties.

Potential challenges and alternative approaches: Potential challenges in the tasks described above may arise from the possibility of the catalysts/reductants having poor solubility in water. If solubility issues are encountered, we can easily incorporate water-solubilizing groups into the catalyst/reductant structures [75,76]. Additional concerns could be raised about cross-reactivity of different co-reactants with themselves interfering with the assay. We anticipate that this will not be a major issue as 1) chemiluminescence depends on redox changes of a given catalyst, thus cross-reactivity of reactants is irrelevant as long as it is not in totality, as evidenced by current ECL/co-reactant systems [6,35,36].

FIG. 13 illustrates a further exemplary device embodiment in which the bottom substrates and cover plates were made from borosilicate glass, which were purchased from Telic (Valencia, Calif., USA). This embodiment is shown in U.S. Pat. No. 8,507,208, which is incorporated by reference herein in its entirety. The bottom substrates were pre-coated with a thin layer of chromium followed by photoresist (protective layers). The channel design used for this study was patterned on a photomask, which was obtained from Fineline Imaging (Colorado Springs, Colo., USA). Standard photolithographic patterning was performed to transfer the channel design of the photomask onto the bottom substrates. Then, the photoresist layer was developed using MF-319 (Rohm and Haas) followed by etching the chromium layer using chromium etchant (Transene). All channel segments were initially etched to 2 μm using a solution of buffered oxide etchant purchased from Transene. In order to prevent further etching at the section of the membrane in the embodiment illustrated in FIG. 13, the portion was manually covered with a layer of photoresist. After the photoresist was dried out, the remaining channels were etched to 30 μm. Following this step, access holes were punched at the end of each channel segment using a micro-abrasive power blasting system (Vaniman). Then, the protective layers were removed using acetone followed by chromium etchant. The channels created on the bottom substrate were sealed with the cover plate using a sodium silicate solution (2.7% SiO2, 1.4% NaOH by weight) as an adhesive layer. After applying pressure to these two plates, the excess sodium silicate solution in the channels was removed using a vacuum pump purchased from Thermo Fisher Scientific Inc. During this process, however, the solution still remained within the shallow region (2 μm) due to the larger capillary forces. Finally, the device was heated at 80° C. in a conventional oven at atmospheric pressure for 15 min. As a result, the sodium silicate solution in the shallow region formed a porous silica gel, which was used as a membrane that could trap resorufin. In order to enhance the plate bonding strength, the device was placed in the oven at 80° C. overnight.

Channel Coatings. First, sample reservoirs were attached to the end of each channel segment. Then, the channels were filled with 1 N NaOH for 60 min followed by rinsing with de-ionized water and acetone. The device was dried in the oven at 80° C. for 10 min. In this assay, reduction of the electroosmotic flow (EOF) in segment 2 of the embodiment shown in FIG. 1 was necessary, and this was done as follows: while a vacuum was applied at reservoir 2, solutions of N-(3-triethoxysilylpropyl) formamide and 3-aminopropyl triethoxysilane were introduced from reservoirs 4 and 1, respectively. The N-(3-ethoxysilylpropyl0) formamide solution was prepared by mixing 1.8 mL of ethyl formate and 5.0 mL of 3-aminopropyl triethoxysilane followed by letting the mixture stand for 48 hours. Then, vacuum was removed and both solutions were allowed to flow by gravity for 45 min.

After rinsing the channels with methanol, segment 1 was ready for the ELISA coatings. To begin with, while vacuum was applied at reservoir 2, de-ionized water and 5% (w/v) glutaraldehyde were introduced from reservoirs 4 and 1, respectively. Vacuum was removed and these solutions allowed to flow by gravity for 45 min. Following this step, the solution in reservoir 1 was replaced with de-ionized water and vacuum was applied at reservoir 2 for a few seconds to rinse segment 1. The rest of the coatings shown in the following list were performed in the following manner: 100 mM (pH 7.4) phosphate buffer was used as the washing buffer in each of these steps unless otherwise stated.

1. 1% (w/v) bovin serum albumin (BSA) prepared with 100 mM (pH 9.4) carbonate buffer (60 min).
2. Wash the channel. Appropriate dilution of mouse anti-BSA solution prepared with 100 mM (pH 7.4) phosphate buffer (30 min). The mouse anti-BSA is the analyte in this assay.
3. Wash the channel. 40× dilution of biotinylated goat anti-mouse immunoglobulin (BioGenex, San Diego, Calif., USA) prepared with 100 mM (pH 7.4) phosphate buffer (10 min).
4. Wash the channel. 25× dilution of peroxidase conjugated streptavidin (BioGenex)/0.05% (v/v) Tween20 (10 min).
5. Wash the channel.

Device Operation. Initially, all channel segments were filled with 100 mM (pH 7.4) phosphate buffer. Then, the buffer in reservoir 1 of FIG. 1 was replaced with Amplex Red (10 µM)/H2O2 (5 µM) solution prepared with 10 mM (pH 7.4) phosphate buffer. Amplex Red was purchased from Invitrogen (Eugene, Oreg., USA). Reservoir 2 was filled with 100 mM sodium tetraborate. Vacuum was applied at reservoir 4 for a few seconds to obtain the initial flow profile of these two solutions. By removing the solution in reservoir 4, continuous pressure driven flow of Amplex Red/H2O2 and sodium tetraborate buffer was observed. After setting up the initial flow profile, the device was operated by applying voltages (e.g., 100 V-1000 V) at reservoir 3 and electrically grounding at reservoir 4 using an EMCO octo-channel high voltage system. In the ELISA region (segment 1), Amplex Red, which is a non-fluorescent dye, was converted to resorufin, which is a mixture of neutral resorufin and negatively charged resorufin anion at pH 7.4. The anionic form of resorufin is significantly more fluorescent than the neutral form. Introduction of the sodium tetraborate buffer from reservoir 2 converts all the resorufin to its fluorescent state, while at the same time enhancing its electrophoretic mobility. The dye molecules were visualized using a fluorescence microscope (Nikon, Japan). Due to the applied electric field, resorufin molecules were accumulated in front of the membrane, and the fluorescence signal around this region was collected using a CCD camera connected to the microscope. Finally, the fluorescence intensity was measured using Photoshop (Adobe Systems Incorporated) to quantitate the ELISA assay.

The device described in this example comprises, at a minimum, two microfluidic channels. In FIG. 14A, one of the two channels (the channel) includes regions A, optional region J, and region F, while the second of the two channels (the "trapping channel", also referred to herein as the "microfluidic trapping region") is labeled as B; as noted below, the two channels may be arranged in other geometries than that shown here. In the example given here, region A comprises what will be termed here an "ELISA region," but may be more broadly described as a binding region. In an assay, this region is formed by using methods known in the art to attach antibodies to the surface of the channel in region A, followed by a wash and subsequent exposure to a sample containing the target analyte of interest (delivered from reservoir H), wherein the analyte will bind to at least some of the antibodies. After a suitable incubation period, the channel is washed again (from reservoir H) to remove excess sample matrix, and then a second antibody, conjugated to an enzyme or other catalyst, is introduced so as to form a sandwich complex between the first antibody, the antigen/target analyte, and the antibody-enzyme conjugate. A final wash to remove excess antibody-enzyme conjugate will provide the ELISA region, A, in which there is bound analyte, and approximately one enzyme/catalyst for each analyte. Of course, this description is of a particular embodiment; implementation of different variants of the ELISA reaction known in the art would lead to different means of forming the ELISA surface.

A microfluidic side channel, B (the trapping channel), comprises a semipermeable membrane, C, that allows the passage of small ions such as inorganic buffer components, but that traps larger molecules such as the detectable ELISA reaction product (−)P* in a detection zone that includes the face of the semipermeable membrane and extends out some small distance, though typically not as far as the microfluidic channel. On the side of this membrane opposite to the microfluidic channel (the rear, or back side) there is an electrode, D, the polarity of which is chosen to be opposite to that of the detectable ELISA reaction product. In the example given here, the detectable ELISA reaction has been arbitrarily assigned a negative charge, and thus the electrode D is set to a positive potential (high voltage). The potential at electrode D is sufficiently high that it can strongly attract the detectable ELISA reaction product (−)P* even in opposition to a pressure driven flow passing from reservoir H through the waste channel F. In the example provided here, this is a ground. Microfluidic channel B is also provided with a detection system E that is placed so as to detect species at or near the surface of semi-permeable membrane C. The electrode complimentary to D is electrode G, shown in FIG. 3A at the end of waste channel F. A general purpose reservoir/entry portal is provided at H, which is used to supply the various components of the assay (e.g., the analyte containing sample, the antibody-enzyme conjugate, the various wash solutions, and the ELISA reaction substrate, etc.). Components J and K (a downstream channel and an auxiliary microfluidic channel) are not essential for the operation of all embodiments, but as will be discussed in detail below, will typically be included since they may be useful for the purpose of establishing the ELISA region, as well as for implementation of a variety of other useful embodiments. The choice of substrate, S, and ELISA reaction provides advantages of the methods and devices described herein, since separation from and concentration of the detectable ELISA reaction product (−)P* is accomplished by a difference in net charge between the substrate and product of the catalyzed reaction.

Following establishment of the ELISA region as described above and washing to remove excess antibody-enzyme conjugate, a substrate for the enzyme is introduced by pumping or by simple hydrostatic pressure as a solution in an appropriate buffer for the reaction. The enzyme present will then convert some small fraction of the substrate to a detectable product having a different net charge. In the example given here, the substrate is neutral, while the product has a single negative charge. Both substrate and product will be carried through the microfluidic channel by pressure driven flow, but the negatively charged detectable ELISA reaction product will also experience an attractive force from electrode D that is at a positive potential and will thus be drawn towards semipermeable membrane C, where it will collect at, or near the membrane surface and be measured by detection device E. Since the substrate, S, is not charged, it will not be attracted to electrode D and instead will be carried with the bulk solution towards waste. Thus, through this process, the detectable ELISA reaction product is concentrated in a small volume (increasing the signal in the signal-to-noise ratio, S/N), while at the same time other assay components (most particularly the substrate S) are carried away from the detection region at the face of the semipermeable membrane (decreasing the noise in the signal-to-noise ratio, S/N). The combination of signal increase through concentration, with noise decrease through separation from the other assay components, leads to an enormous increase in S/N and a consequent dramatic improvement in the limit of detection for the analyte. Compared with a conventional ELISA method without this simultaneous separation and concentration, this method provides more sensitive detection and/or more rapid detection.

A specific example of one embodiment is the use of the commercially available ELISA substrate Amplex Red® for an ELISA reaction using horseradish peroxidase as the enzyme. Thus, the mouse antibody to BSA can be detected as follows. An ELISA surface is established in a microfluidic device of the form described in FIG. 3A, in which the regions J and F have been coated with N-(3-(triethoxysilyl)propyl)formamide to reduce electroosmotic flow. The semipermeable membrane C is comprised of silica, and the detection device used is a fluorescence microscope with a high-pressure mercury lamp as the excitation source (spectral range 184 nm to 577 nm). The fluorescence signal is collected in this set-up by exciting the analyte molecules with a light beam from the mercury lamp after passing it through a low pass optical filter (transmitted wavelengths <540 nm) and then collecting the fluorescence signal with a CCD camera that has a high pass optical filter (transmitted wavelengths >600 nm) placed in front of it. Solutions are provided to the device using a well, and flow is a result of simple hydrostatic pressure. The ELISA surface comprises a coating of BSA that has been bound to the glass surface by first reacting the cleaned glass surface with aminopropyltriethoxysilane, followed by aqueous glutaraldehyde (and a wash step), followed by BSA (and a wash step), followed by a basic solution of sodium borohydride (and a subsequent wash), to provide a surface in which the BSA is covalently bound to the surface. The thus formed BSA surface is exposed to a solution containing some amount of mouse anti-BSA antibody, the mixture allowed to incubate, after which it is washed with buffer to remove excess substrate solution. A solution of biotinylated goat anti-mouse antibody in buffer is then introduced, and after about thirty minutes of incubation, the channel washed with buffer. A solution of streptavidin-horseradish peroxidase in buffer is then introduced, the mixture allowed to incubate, and the channel then washed with buffer, thereby providing the ELISA surface of this embodiment, comprising a quaternary complex of (glass-linker-BSA)-(anti-BSA antibody analyte)-(goat anti-mouse/biotin conjugate)-(horseradish peroxidase/streptavidin conjugate). A solution having 10 μM Amplex Red® and 5 μM hydrogen peroxide in 0.1 M pH 7.4 phosphate buffer is then introduced while applying a positive potential at electrode D. As is known in the literature, horseradish peroxidase converts Amplex Red® to the fluorescent and readily detectable anion of the dye resorufin under these conditions, as illustrated in the below scheme:

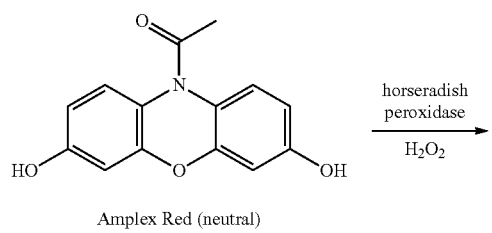

Amplex Red (neutral)

-continued

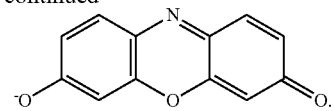

resorufin (anionic)

The anionic dye is selectively drawn towards the cathode D, where it is trapped and concentrated at membrane C; unreacted Amplex Red®, being uncharged, is not influenced by the electric field, and continues with the bulk of the solvent through regions J and F to waste. Signal is then detected at varying intervals at the face of the semi-permeable membrane. The signal so-produced by the separation/concentration effects is improved by >10-fold relative to that produced in control experiments in which the detectable ELISA reaction product is formed without the product separating/concentrating effect of the electric field and membrane present. In the context of a pH change embodiment, described below, dramatic signal enhancements of greater than 1000 fold are achievable.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups and classes that can be formed using the substituents are disclosed separately. When a Markush group or other grouping is used herein, all individual members of the group and all combinations and subcombinations possible of the group are intended to be individually included in the disclosure. As used herein, "and/or" means that one, all, or any combination of items in a list separated by "and/or" are included in the list; for example "1, 2 and/or 3" is equivalent to "'1' or '2' or '3' or 1 and 2' or 1 and 3' or '2 and 3' or '1, 2 and 3'".

Every formulation or combination of components described or exemplified can be used to practice the invention, unless otherwise stated. Specific names of materials are intended to be exemplary, as it is known that one of ordinary skill in the art can name the same material differently. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method to detect a target analyte in a sample, the method comprising the steps of:
   (a) providing a microfluidic device comprising a binding surface in at least one microfluidic channel, wherein at least a portion of the binding surface has channel walls comprising electrodes comprising a first electrode and a second electrode, wherein the binding surface comprises binding molecules capable of selectively binding to the target analyte;
   (b) introducing to the binding surface a first solution comprising target analyte molecules, wherein at least a portion of the target analyte molecules can selectively bind to the binding molecules of the binding surface to provide a binding surface having bound target analyte molecules;
   (c) binding the target analyte to the binding surface by applying an electrical potential between the first and second electrodes during at least a portion of the binding step, thereby enhancing a rate of binding of the target analyte molecules to the binding molecules;
   (d) providing to the binding surface having the bound target analyte molecules a second solution comprising reporter molecules, wherein at least a portion of the reporter molecules further bind directly or indirectly to the target analyte molecules bound to the binding surface; wherein the reporter molecules can generate a detectable signal;
   (e) providing to the binding surface having a bound target analyte molecules and the bound reporter molecules a solution comprising substrate molecules, wherein at least a portion of the substrate molecules undergo a catalytic chemical reaction imitated by the reporter molecules, thereby producing reaction product molecules having an ionic charge different from an ionic charge of the substrate molecules;
   (f) transporting at least some of the reaction product molecules into a microfluidic trapping region in fluid communication with the microfluidic binding region,
      wherein a transporting comprises applying an electric potential between a third electrode positioned in a first microfluidic side channel and a fourth electrode positioned in the microfluidic channel or in a second microfluidic side channel;
      wherein the semipermeable membrane is positioned in a first microfluidic side channel between the third electrode and the microfluidic channel and having a surface oriented towards the microfluidic channel; and
      wherein the electrical potential provides a force attracting the reaction production molecules towards the microfluidic trapping region;
   (g) concentrating the reaction product molecules in the microfluidic trapping region in front of, at the surface of an/or within a semipermable membrane; wherein the signal is measured from the reaction product molecules in front of, at the surface of and/or within the semipermable membrane; and
   (h) detecting the signal indicating an amount of the originally present target analyte molecules in the sample.

2. The method of claim 1, wherein steps (b) and (c) are performed with additional solutions comprising the target analyte solution at least five times prior to performing step (d).

3. The method of claim 2, wherein at least 10 times more target analyte molecule is bound to the binding surface compared with binding the target analyte molecule in the absence of an applied electric field between the first and second electrodes.

4. The method of claim 1, wherein an amount of time required to bind a specified amount of target analyte molecules applied to the binding surface is reduced by approximately ten fold compared with binding the target analyte molecules in the absence of an applied electric field between the first and second electrodes.

5. The method of claim 1, wherein the binding surface is a derivatized glass with a silane compound and an aldehyde compound.

6. The method of claim 5, wherein the silane compound is 3-aminopropyltriethoxysilane and the aldehyde compound is glutaraldehyde.

7. The method of claim 1, wherein the binding molecules capable of selectively binding to the target analyte are an antibody with specificity for binding the target analyte.

8. The method of claim 7, wherein the method further comprises blocking nonspecific binding sites on the binding surface by applying a solution comprising a peptide, a polypeptide, or a combination thereof following step (a).

9. The method of claim 7, wherein the method further comprises removing unbound and nonspecifically bound target analyte following step (c).

10. The method of claim 7, wherein the method further comprises removing unbound and nonspecifically bound reporter molecules following step (d).

11. The method of claim 1, wherein the reporter molecules comprise an enzyme.

12. The method of claim 11, wherein the enzyme comprises alkaline phosphatase, acid phosphatase, horseradish peroxidase, beta-galactosidase, glucose oxidase, carboxypeptidase B, porcine liver esterase, rabbit esterase, lipase, butyryl cholinesterase, arginase, a catalyst for a bond cleavage reaction, a catalyst for a bond forming reaction, a catalyst for an oxidation reaction, a catalyst for a reduction reaction or any combination of these.

13. The method of claim 12, wherein the reporter molecules comprise a catalyst capable of electrochemiluminescence reactions.

14. The method of claim 13, wherein the catalyst is tris(bipyridine) ruthenium (II) chloride (Ru(bpy)3).

15. The method of claim 13, wherein the method further comprises applying an electrical potential between the first and second electrodes after the reporter molecule binding step (d) and wherein the detecting step (h) comprises detecting an electrochemiluminescence reaction.

16. The method of claim 11, wherein the reporter molecules comprise a catalyst capable of creating a colored or fluorescent ionized product from precursor colored or fluorescent product.

17. The method of claim 16, wherein the binding molecules on the binding surface comprise antigens of antibodies, antibodies, biotin, streptavidin, aptamers, nucleic acids, peptide nucleic acids, conjugates between antigens of antibodies, antibodies, biotin, streptavidin, aptamers, nucleic acids, peptide nucleic acids, or any combination of these.

18. The method of claim 1, wherein step (g) is performed after one or more time intervals.

* * * * *

UNITED STATES PATENT AND TRADEMARK OFFICE
CERTIFICATE OF CORRECTION

PATENT NO. : 11,402,376 B2
APPLICATION NO. : 16/360611
DATED : August 2, 2022
INVENTOR(S) : Debashis Dutta et al.

Page 1 of 1

It is certified that error appears in the above-identified patent and that said Letters Patent is hereby corrected as shown below:

In the Claims

In Column 46, in Claim 1, Line 20, please delete the word "the" and replace with --a--.

In Column 46, in Claim 1, Line 21, please delete the word "a" and replace with --the--.

In Column 46, in Claim 1, Line 30, please delete the word "a" and replace with --the--.

Signed and Sealed this
Fourteenth Day of November, 2023

Katherine Kelly Vidal
*Director of the United States Patent and Trademark Office*